US007118757B1

(12) United States Patent
Seid, Jr. et al.

(10) Patent No.: US 7,118,757 B1
(45) Date of Patent: Oct. 10, 2006

(54) MENINGOCOCCAL CLASS 1 OUTER-MEMBRANE PROTEIN VACCINE

(75) Inventors: Robert C. Seid, Jr., San Francisco, CA (US); Peter R. Paradiso, Pittsford, NY (US); Jan T. Poolman, Broek in Waterland (NL); Peter Hoogerhout, Bilthoven (NL); Emmanuel J. H. J. Wiertz, Utrecht (NL); Peter van der Ley, Utrecht (NL); John Edward Heckels, Romsey (GB); Ian Nicholas Clarke, Southampton (GB)

(73) Assignees: Wyeth Holdings Corporation, Madison, NJ (US); De Staat der Nederlanden Vertegenwoordigd Door de Minister Van Welzijn, Volksgezondheid en Cultuur, Bilthoven (NL)

( * ) Notice: Subject to any disclaimer, the term of this patent is extended or adjusted under 35 U.S.C. 154(b) by 0 days.

(21) Appl. No.: 08/204,808

(22) Filed: Feb. 15, 1994

Related U.S. Application Data

(63) Continuation of application No. 07/691,005, filed as application No. PCT/US89/05678 on Dec. 19, 1989, now abandoned.

(30) Foreign Application Priority Data

| | | |
|---|---|---|
| Dec. 19, 1988 | (NL) | 88.03111 |
| Jan. 6, 1989 | (NL) | 89.00036 |
| Jun. 26, 1989 | (NL) | 89.01612 |

(51) Int. Cl.

| | |
|---|---|
| ***A61K 39/095*** | (2006.01) |
| ***A61K 39/02*** | (2006.01) |
| ***A61K 39/385*** | (2006.01) |
| ***A61K 39/38*** | (2006.01) |
| ***C07K 1/00*** | (2006.01) |

(52) U.S. Cl. .............................. 424/250.1; 424/234.1; 424/190.1; 424/184.1; 424/197.11; 424/194.1; 530/350; 530/300; 530/825; 530/807; 530/806

(58) Field of Classification Search ................. 424/88, 424/92, 184.1, 43 A, 185.1, 192.1, 249.1, 424/184, 185, 250.1, 234.1, 190.1, 197.11; 435/69.1, 171.3; 530/300, 350, 825, 806, 530/807; 514/2

See application file for complete search history.

(56) References Cited

U.S. PATENT DOCUMENTS

| | | | | |
|---|---|---|---|---|
| 4,271,147 | A * | 6/1981 | Helting | 424/92 |
| 4,356,170 | A * | 10/1982 | Jennings et al. | 424/92 |
| 4,459,286 | A * | 7/1984 | Hilleman et al. | 424/87 |
| 4,601,903 | A | 7/1986 | Frasch | 424/92 |
| 4,603,112 | A | 7/1986 | Paoletti et al. | 435/235 |
| 4,673,574 | A | 6/1987 | Anderson | 424/92 |
| 4,695,624 | A * | 9/1987 | Marburg et al. | 530/395 |
| 4,707,543 | A | 11/1987 | Zollinger et al. | 530/402 |
| 4,711,779 | A * | 12/1987 | Porro et al. | 424/92 |
| 4,761,283 | A * | 8/1988 | Anderson | 424/92 |
| 4,762,713 | A | 8/1988 | Anderson | 424/92 |
| 4,830,852 | A * | 5/1989 | Marburg et al. | 424/85.8 |
| 4,882,317 | A * | 11/1989 | Marburg et al. | 514/54 |
| 5,034,519 | A * | 7/1991 | Beuvery et al. | 536/117 |
| 5,182,109 | A * | 1/1993 | Tamura et al. | 424/92 |
| 5,312,620 | A * | 5/1994 | Ribi | 424/78.31 |
| 5,356,778 | A * | 10/1994 | Hansen et al. | 435/7.2 |
| 5,736,361 | A | 4/1998 | Carbonetti et al. | 435/69.3 |
| 5,747,287 | A * | 5/1998 | Blake et al. | 435/69.1 |
| 5,766,914 | A * | 6/1998 | Deits | 435/207 |
| 6,348,332 | B1 * | 2/2002 | Carbonetti et al. | 435/69.3 |

FOREIGN PATENT DOCUMENTS

| | | | |
|---|---|---|---|
| CN | 1030443 A | * | 1/1989 |
| EP | 048023 | * | 3/1982 |
| EP | 0090660 | | 10/1983 |
| EP | 0145359 | | 6/1985 |
| EP | 0182401 | | 5/1986 |
| EP | 0 208 375 | * | 1/1987 |
| EP | 0301992 | | 2/1989 |
| JP | 64029321 | * | 1/1989 |
| WO | WO 89/04873 | * | 6/1989 |
| WO | WO 89/10967 | | 11/1989 |

OTHER PUBLICATIONS

Bessler et al Immunobiol 170: 239-244, 1985 Specific Antibodies Elicited by Antigen Covalently Linked to a Synthetic Adjuvant.*

Lerner Nature 299: 592-596, Tapping the Immunological Repertoire to Produce Antibodies of Predetermined Specificity.*

Teerink et al. J. Exp. Med. 166: 63-76, 1987.*

Wetzler et al. Trans. Assoc. Am. Physicians CII: 78-90, 1989.*

Runeberg-Nyman et al. In: Keystone Symposium on Protein Folding, Structure and Function, CO, USA, Apr., 8-14, 1991, abstract.*

Chattopadhyay et al. In: Proc. European Congr. Biotechnol. 5 Meeting, Copenhagen, Jul. 8-13, 1990, abstract.*

Laitinen K. NPHI, A1/1988, Helsinki, 57-62 (relevant pages), 1988.*

Poolman et al. Dev. Biol. Stand. 63: 147-152, S. Karger, Basel, 1986.*

Wahlstrom et al. In: Neisseriae 1990 (Ed) Achtman et al. Walter de Gruyter & Co., Berlin, pp. 307-312, 1991.*

Sigma 1987 Catalog of Biochemical and Organic Compounds for research and Diagnsotic Clinical Reagents. pp. 196-200, 1987.*

Abdillahi et al. Microb. Pathogen. 4: 27-32, 1988.*

(Continued)

*Primary Examiner*—S. Devi
(74) *Attorney, Agent, or Firm*—Hamilton, Brook, Smith & Reynolds, P.C.

(57) ABSTRACT

Outer-membrane vesicles, Class 1 outer membrane proteins of *Neisseria meningitidis*, fragments or oligopeptides containing epitopes of the Class I OMP can be used to immunize against meningococcal disease.

9 Claims, 21 Drawing Sheets

OTHER PUBLICATIONS

Palker et al. PNAS 85: 1932-1936, Mar. 1988.*
Barlow et al. In: Proceedings of the Symposium, 110th Meeting of the Society for General Microbiology, University of Southampton (UK), Jan. 6-8, 1988.*
Lowell et al Journal of Exper. Med 167:658-663, 1988.*
Makela et al (Seminars in Inf. Dis., vol. IV: Bacterial Vaccines, 1982, p. 360-365.*
Newton et al Science 244: 70-72 Apr. 1989.*
Poolman et al I & I 40:398-406 1983.*
Frasch et al vol. IV: Bacterial Vaccines, 1982 pp. 263-267.*
Wiertz et al Cell Biochem Suppl 326 Jan. 1984.*
Lynch et al J. Biophysical Soc. 104-107, 1984.*
Porro M. In: Towards Better Carbohydrate Vaccines. (Ed) Bell et al. John Wiley & Sons, New York, pp. 279-306, 1987.*
Gotschlich et al. PNAS 84: 8135-8139, 1987.*
Carbonetti et al. PNAS 85: 6841-6845, 1987.*
McGuinness et al. Lancet 337: 514-517, 1991.*
Frasch et al. Clin. Invest. Med. 9: 101-107, 1986.*
Beuvery et al. Medecine Tropicale 43: 123-127, 1983.*
Frasch CE. Clin. Microbiol. Rev. 2: S134-S138, Apr. 1989.*
Bernatowitz et al. Anal. Biochem. 155: 95-102, 1986.*
IM Kramer et al. In: The Pathogenic Neisseriae, Proceedings of the Fourth International Symposium, Asilomar, California, Oct. 21-25, American Society for Microbiology, Washington, D.C., pp. 611-615, 1985.*
Sukkonen et al Microbial Pathogenesis 3:261-267, 1987.*
Mandrell et al Infect. & Immunity 57: 1590-1598, 1989.*
Hirama Immunological Method vol. III, Chapter 3, p. 52.*
Beuvery, E.C. et al., Infect. Immun. 40:369-390 (1983).
Jiskoot, W. et al., Infect. Immun. 54:333-338 (1986).
Wang, L.Y. and Frasche, C.E., Infect. Immun. 46:408-414 (1984).
Teerlink, T. et al., Vaccine 5:307-314 (1987).
Gregoriadis, G. et al., Vaccine, 5:145-151 (1987).
Tsai, C.M. and Frasch, C.E., J. Bacteriol. 141:169-176 (1980).
Tsai, C.M. et al., Chem. Abstr. 94:, abstract 2051112.
Barlow, A.K. et al., Infect. Immun. 55:2735-2740 (1987).
Wedege, E. et al., J. Immunol. Methods, 113:51-59 (1988).
Barlow, A.K. et al., Molecular Microbiology, 3(2): 131-139 (1989).
International Search Report from PCT Application No. 89/05678 (Publication No. WO90/06696), which was filed Dec. 19, 1989.
European Patent No. 0,351,604 (Jan. 24, 1990).
European Patent No. 0,109,688 (May 30, 1984).
European Patent No. 0,372,501 (Jun. 13, 1990), considered only to extent of Applicants ZDS Document not translated.
European Patent No. 0,011,243 (May. 28, 1980).
Abdillahi and Poolman, Biological Abstracts 87:115445 (1989).
Poolman, J.T. et al., Infect. Immun. 57:1005-1007 (1989).
Wedege, E. and L. Oddvar Frohølm, "Human Antibody Response to a Group B Serotype 2a Meningococcal Vaccine Determined by Immunoblotting," *Infection and Immunity*, 51 (2) :571-578 (1986).
Frasch, C.E., et al., "Immune Responses of Adults and Children to Group B *Neisseria meningitidis* Outer Membrane Protein Vaccines," *Bacterial Vaccines*, 262-272 (1988).
Beuvery, E.C., et al., "Characteristics of an Alternative Meningococcal Type 15 (P1. 16) Outer Membrane Protein Vaccine," *J. Microbiology*, 52:232-235 (1986).
Poolman, J.T., et al., "Comparison of Meningococcal Outer Membrane Protein Vaccines Solubilized with Detergent or C Polysaccharide," *Antonie van Leeuwenhoek*, 53:413-419 (1987).
Wiertz, E.J.H.J., et al., "Human T-Cell Epitope Mapping of the Meningococcal Class 1 Outer Membrane Protein," *J. Cell Biochem Suppl. 0* (13 Part A) (1989); Abstract C 722.
Abdillahi, Hussein et al., "Definition of Meningococcal Class 1 OMP Subtyping Antigens by Monoclonal Antibodies," *FEMS Microbiology Immunology*, vol. 47:139-144 (1988).
West., Susan E.H. et al., "Genetic Loci and Linkage Associations in *Neisseria gonorrhoeae* and *Neisseria meningitidis,*" *Clinical Microbiology Reviews*, vol. 2, Suppl.:S92-S103 (1989).
Barlow, Ann K. et al., "Molecular Cloning and Expression of *Neisseria meningitidis* Class 1 Outer-Membrane Protein in *Escherichia coli* K-12," *J. Med. Microbiol.* vol. 26:180-183 (C) (1988).
Stein, Daniel C., "Introduction of Cloned Genes into *Neisseria gonorrhoeae,*" *Clinical Microbology Reviews*, vol. 2, Suppl.:S146-S149 (1989).
Shinners, Elizabeth N. et al., "*Neisseria gonorrhoeae* Recombinant Strains Expressing Hybrid Serological Reactivities of Outer Membrane Proteins IA and IB," *J. Infectious Diseases* vol. 158:529-536 (1988).
Tarkka, Eveliina et al., "Antibody Production to a Meningococcal Outer Membrane Protein Cloned into Live *Salmonella typhimurium* aroA Vaccine Strain," *Microbial Pathogenesis*, vol. 6:327-335 (1989).
Tarkka, Eveliina et al., "Cloning of an Outer Membrane Protein of *Neisseria meningitidis* in *Escherichia coli,*" *Microbial Pathogenesis*, vol. 3:445-453 (1987).

* cited by examiner

FIG. 2

```
         SEQ ID
          NO:
                                        20                                          30
H4476    61         Gly Arg Asn Tyr Gln Leu Gln Leu Thr Glu Ala     Gln Ala Ala Asn Gly Gly Ala
         62         GGC AGG AAC TAC CAG CTG CAA TTG ACT GAA GCA     CAA GCC GCT AAC GGT GGA GCG AG

M1080    193, 63                Ile *** Ala                     Gln Pro Gln Ala Thr Asn Gly Val Gln Gly
         64         ... ... ... AT. T.. GC. ... ... ..C ..G CAG CCC ... ..A A.. ... ... .TG CAA G..

H355     65                     Phe                             Pro Pro Ser Lys Ser Gln Pro
         66         ... ... ... .T. ... ... ..G ... ..C ... C.G CCC TC. AAG AG. C.A CC.

6940     67             Asn     Ile                             Pro Pro Ser Lys Gly Gln Thr Gly
         68         ... .AC ... ATT ... ... ... ... ..C ... C.A CCC TC. AAA .GT C.G ACG ..C

6557     69                     Tyr                             Gln Pro Ser Arg Thr Gln Gly Gln Thr
         70         ... ... ... ... ... ... ... ... ... ... CA. CCC TC. AGA A.. C.A ... CA. A.. ...

870227   71                     Ile                             Pro Leu Pro Asn Ile Gln Pro Gln
         72         ... ... ... AT. ... ... ..G ... ..C ... C.G CTC .C. AAT AT. C.A CC. CAG

B40      73                     Ile                             Pro Leu Pro Asn Ile Gln Pro Gln
         74         ... ... ... AT. ... ... ..G ... ..C ... C.G CTC .C. AAT AT. C.A CC. CAG

                                                        40                                      50
H4476    61         Gly Gln Val Lys Val     Thr Lys Val Thr Lys Ala Lys Ser Arg Ile Arg Thr Lys Ile Ser
         62         GGT CAG GTA AAA GTT     ACT AAA GTT ACT AAG GCC AAA AGC CGC ATC AGG ACG AAA ATC AGT

M1080    63             Arg Gln Gly Asn Gln Val Thr             Val                         Glu
         64         ... .G. CA. GGC AA. CAG GTA .C. ... ... ... .T. ... ... ... ... ... ... G.. ... ..C

H355     65                             Gln Val                 Ala                         Lys
         66                             CAG GTA ... ... ... ... ... ... ... ... ... ... ... ... ... ...

6940     67                                 Asn                 Ala                         Lys
         68                                 .A. ... ... ... ... ... ... ... ... ... ... ... ... ... ...

6557     69                         Asn Gln Val                 Ala                         Lys
         70                         AA. CAG GTA ... ... ... ... ... ... ... ... ... ... ... ... ... ...

870227   71                                                     Arg                         Lys
         72                                         ... ... ... CG. ... ... ... ... ... ... ... ... ..C

B40      73                                                     Arg                         Lys
         74                                         ... ... ... CG. ... ... ... ... ... ... ... ... ..C
```

FIG. 3A

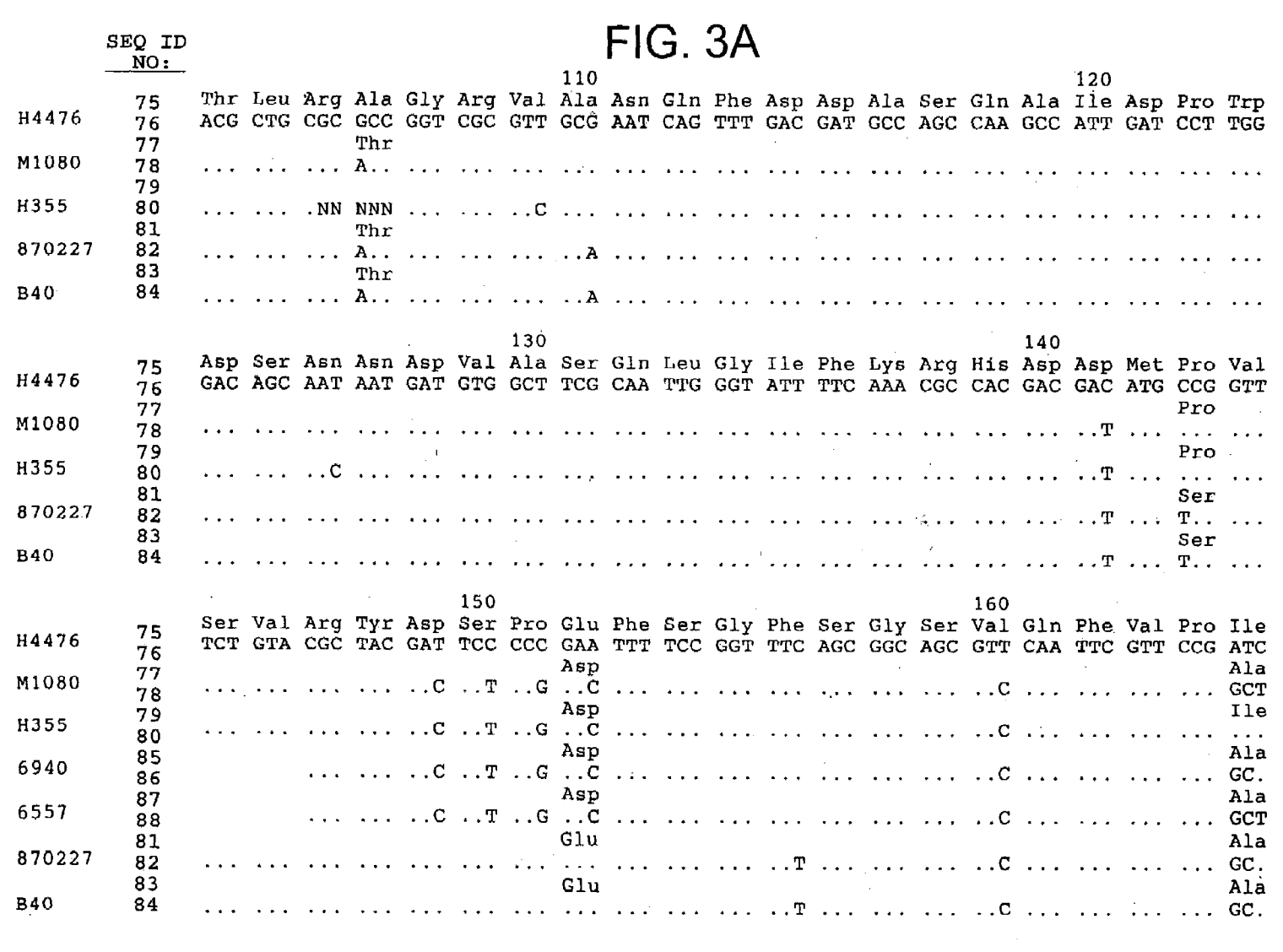

```
          SEQ ID
           NO:
                                                   110                                       120
           75   Thr Leu Arg Ala Gly Arg Val Ala Asn Gln Phe Asp Asp Ala Ser Gln Ala Ile Asp Pro Trp
H4476      76   ACG CTG CGC GCC GGT CGC GTT GCG AAT CAG TTT GAC GAT GCC AGC CAA GCC ATT GAT CCT TGG
           77               Thr
M1080      78   ... ... ... A.. ... ... ... ... ... ... ... ... ... ... ... ... ... ... ... ... ...
           79
H355       80   ... ... .NN NNN ... ... ..C ... ... ... ... ... ... ... ... ... ... ... ... ... ...
           81               Thr
870227     82   ... ... ... A.. ... ... ... ..A ... ... ... ... ... ... ... ... ... ... ... ... ...
           83               Thr
B40        84   ... ... ... A.. ... ... ... ..A ... ... ... ... ... ... ... ... ... ... ... ... ...

                                        130                                 140
           75   Asp Ser Asn Asn Asp Val Ala Ser Gln Leu Gly Ile Phe Lys Arg His Asp Asp Met Pro Val
H4476      76   GAC AGC AAT AAT GAT GTG GCT TCG CAA TTG GGT ATT TTC AAA CGC CAC GAC GAC ATG CCG GTT
           77                                                                               Pro
M1080      78   ... ... ... ... ... ... ... ... ... ... ... ... ... ... ... ... ... ..T ... ... ...
           79                                                                               Pro
H355       80   ... ... ..C ... ... ... ... ... ... ... ... ... ... ... ... ... ... ..T ... ... ...
           81                                                                               Ser
870227     82   ... ... ... ... ... ... ... ... ... ... ... ... ... ... ... ... ... ..T ... T.. ...
           83                                                                               Ser
B40        84   ... ... ... ... ... ... ... ... ... ... ... ... ... ... ... ... ... ..T ... T.. ...

                                    150                                     160
           75   Ser Val Arg Tyr Asp Ser Pro Glu Phe Ser Gly Phe Ser Gly Ser Val Gln Phe Val Pro Ile
H4476      76   TCT GTA CGC TAC GAT TCC CCC GAA TTT TCC GGT TTC AGC GGC AGC GTT CAA TTC GTT CCG ATC
           77                               Asp                                                 Ala
M1080      78   ... ... ... ... ..C ..T ..G ..C ... ... ... ... ... ... ... ..C ... ... ... ... GCT
           79                               Asp                                                 Ile
H355       80   ... ... ... ... ..C ..T ..G ..C ... ... ... ... ... ... ... ..C ... ... ... ... ...
           85                               Asp                                                 Ala
6940       86           ... ... ..C ..T ..G ..C ... ... ... ... ... ... ... ..C ... ... ... ... GC.
           87                               Asp                                                 Ala
6557       88           ... ... ..C ..T ..G ..C ... ... ... ... ... ... ... ..C ... ... ... ... GCT
           81                               Glu                                                 Ala
870227     82   ... ... ... ... ... ... ... ... ... ... ... ..T ... ... ... ..C ... ... ... ... GC.
           83                               Glu                                                 Ala
B40        84   ... ... ... ... ... ... ... ... ... ... ... ..T ... ... ... ..C ... ... ... ... GC.
```

FIG. 3B

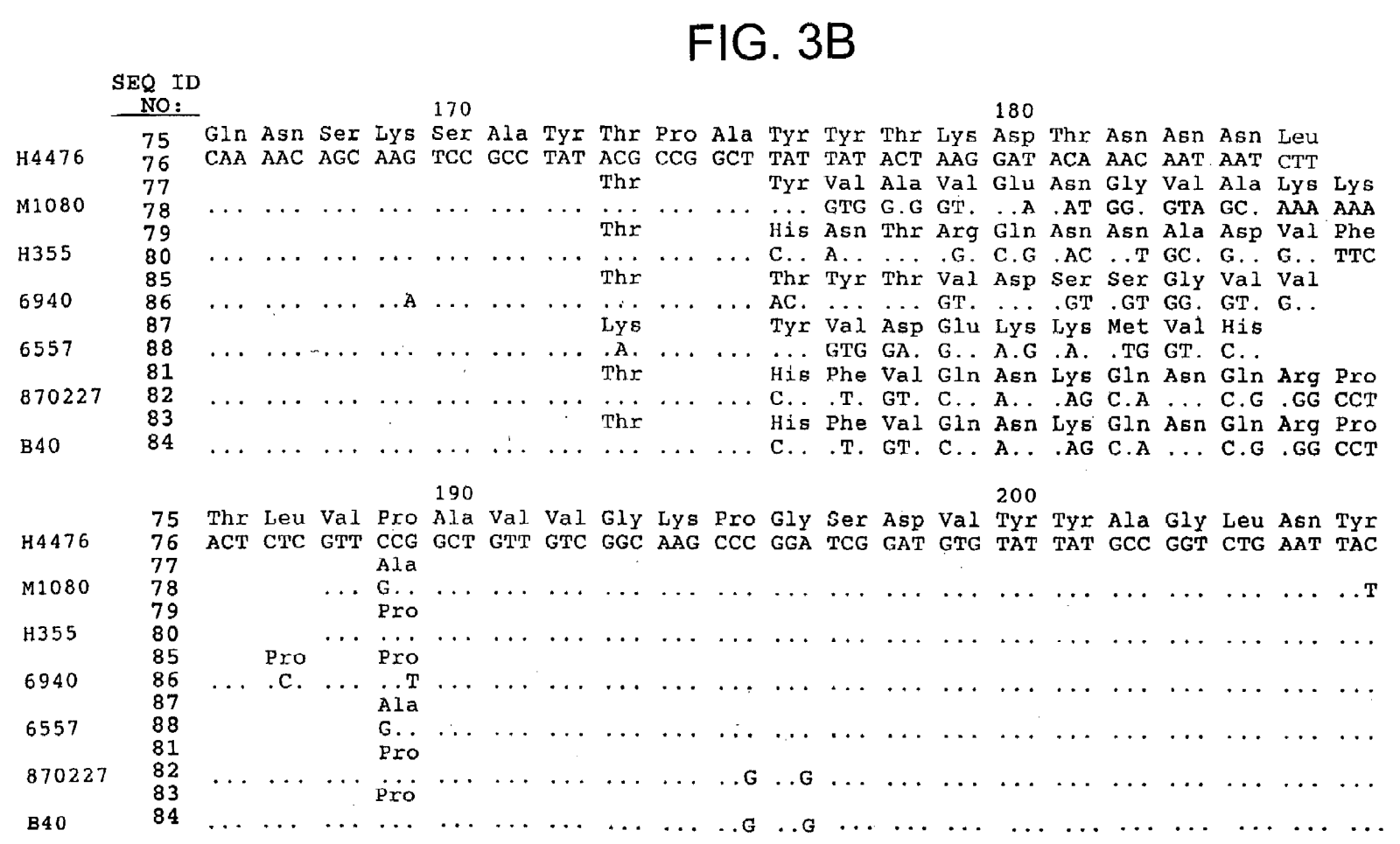

```
         SEQ ID
          NO:                        170                                                  180
           75   Gln Asn Ser Lys Ser Ala Tyr Thr Pro Ala Tyr Tyr Thr Lys Asp Thr Asn Asn Asn Leu
H4476      76   CAA AAC AGC AAG TCC GCC TAT ACG CCG GCT TAT TAT ACT AAG GAT ACA AAC AAT AAT CTT
           77                               Thr         Tyr Val Ala Val Glu Asn Gly Val Ala Lys Lys
M1080      78   ... ... ... ... ... ... ... ... ... ... ... GTG G.G GT. ..A .AT GG. GTA GC. AAA AAA
           79                               Thr         His Asn Thr Arg Gln Asn Asn Ala Asp Val Phe
H355       80   ... ... ... ... ... ... ... ... ... ... C.. A.. ... .G. C.G .AC ..T GC. G.. G.. TTC
           85                               Thr         Thr Tyr Thr Val Asp Ser Ser Gly Val Val
6940       86   ... ... ... ..A ... ... ... ... ... ... AC. ... ... GT. ... .GT .GT GG. GT. G..
           87                               Lys         Tyr Val Asp Glu Lys Lys Met Val His
6557       88   ... ... ... ... ... ... ... .A. ... ... ... GTG GA. G.. A.G .A. .TG GT. C..
           81                               Thr         His Phe Val Gln Asn Lys Gln Asn Gln Arg Pro
870227     82   ... ... ... ... ... ... ... ... ... ... C.. .T. GT. C.. A.. .AG C.A ... C.G .GG CCT
           83                               Thr         His Phe Val Gln Asn Lys Gln Asn Gln Arg Pro
B40        84   ... ... ... ... ... ... ... ... ... ... C.. .T. GT. C.. A.. .AG C.A ... C.G .GG CCT

                                     190                                                  200
           75   Thr Leu Val Pro Ala Val Val Gly Lys Pro Gly Ser Asp Val Tyr Tyr Ala Gly Leu Asn Tyr
H4476      76   ACT CTC GTT CCG GCT GTT GTC GGC AAG CCC GGA TCG GAT GTG TAT TAT GCC GGT CTG AAT TAC
           77               Ala
M1080      78           ... G.. ... ... ... ... ... ... ... ... ... ... ... ... ... ... ... ... ..T
           79               Pro
H355       80           ... ... ... ... ... ... ... ... ... ... ... ... ... ... ... ... ... ... ...
           85       Pro     Pro
6940       86   ... .C. ... ..T ... ... ... ... ... ... ... ... ... ... ... ... ... ... ... ... ...
           87               Ala
6557       88               G.. ... ... ... ... ... ... ... ... ... ... ... ... ... ... ... ... ...
           81               Pro
870227     82   ... ... ... ... ... ... ... ... ... ..G ..G ... ... ... ... ... ... ... ... ... ...
           83               Pro
B40        84   ... ... ... ... ... ... ... ... ... ..G ..G ... ... ... ... ... ... ... ... ... ...
```

FIG. 3C

```
        SEQ ID
         NO:           210                                          220
         75   Lys Asn Gly Gly Phe Ala Gly Asn Tyr Ala Phe Lys Tyr Ala Arg His Ala Asn Val Gly Arg
H4476    76   AAA AAT GGC GGT TTT GCC GGG AAC TAT GCC TTT AAA TAT GCG AGA CAC GCC AAT GTC GGA CGT
         77                               Asn                         Lys
M1080    78   ..G ... ... ... ... ... ... ... ... ... ... ... ... ... .A. ... ... ... ... ... ...
         79                               Arg                         Arg
H355     80   ... ... ... ... ... ... ... CGC ... ... ... ... ... ... ... ... ... ... ... ... ...
         85                               Asn                         Lys
6940     86   ... ... ... ... ... ... ... ... ... ... ... ... ..C ... .A. ... ... ... ..G ..C ...
         87                               Asn                         Lys
6557     88   ... ... ... ... ... ... ... ... ... ... ... ... ... ... .A. ... ... ... ..G ..C ...
         81                               Asn                         Lys
870227   82   ... ... ... ... ... ... ... ... ... ... ... ... ..C ... .A. ... ... ... ..G ..C ...
         83                               Asn                         Lys
B40      84   ... ... ... ... ... ... ... ... ... ... ... ... ..C ... .A. ... ... ... ..G ..C ...

                      230
         75   Asn Ala Phe Glu Leu Phe
H4476    76   AAT GCT TTT GAG TTG TTC
         77   Asp         Glu
M1080    78   G.. ... ... ... ... ...
         79   Asp         Glu
H355     80   G.. ... ... ... ... ...
         85   Asp         Asn
6940     86   G.. ... ... A.T ... ...
         87   Asp         Asn
6557     88   G.. ... ... A.T ... ...
         81   Asp         Glu
870227   82   G.. ... ... ... ... ...
         83   Asp         Glu
B40      84   G.. ... ... ... ... ...
```

EcoRV Cla1 BamH1

GAT ATC ATC GAT GGA TTC (SEQ ID NO: 182)

D I I D G S (SEQ ID NO: 192)

pPX 1647 (VECTOR FLAGELLIN)

ligate in presence of VR-1 oligonucleotide:

BamH1

```
5´  GA TCA GCT GCT AAC GGT GGT GCT TCA GGT CAG GTT G       3´ (SEQ ID NO: 183)
3´        T CGA CGA TTG CCA CCA CGA AGT CCA GTC CAA C CTAG 5´ (SEQ ID NO: 184)

    (G) (S) A A N G G A S G Q V (G) (S) (SEQ ID NO: 185)
```

or ligate in presence of VR-2 oligonucleotide:

```
5´  GA TCA ACC AAA GAC ACC AAT AAC AAC CTC ACC CTA G       3´ (SEQ ID NO: 186)
3´        T TGG TTT CTG TGG TTA TTG TTG GAG TGG GAT C CTAG 5´ (SEQ ID NO: 187)

    (G) (S) T K D T N N N L T L (G) (S) (SEQ ID NO: 188)
```

FIG. 6

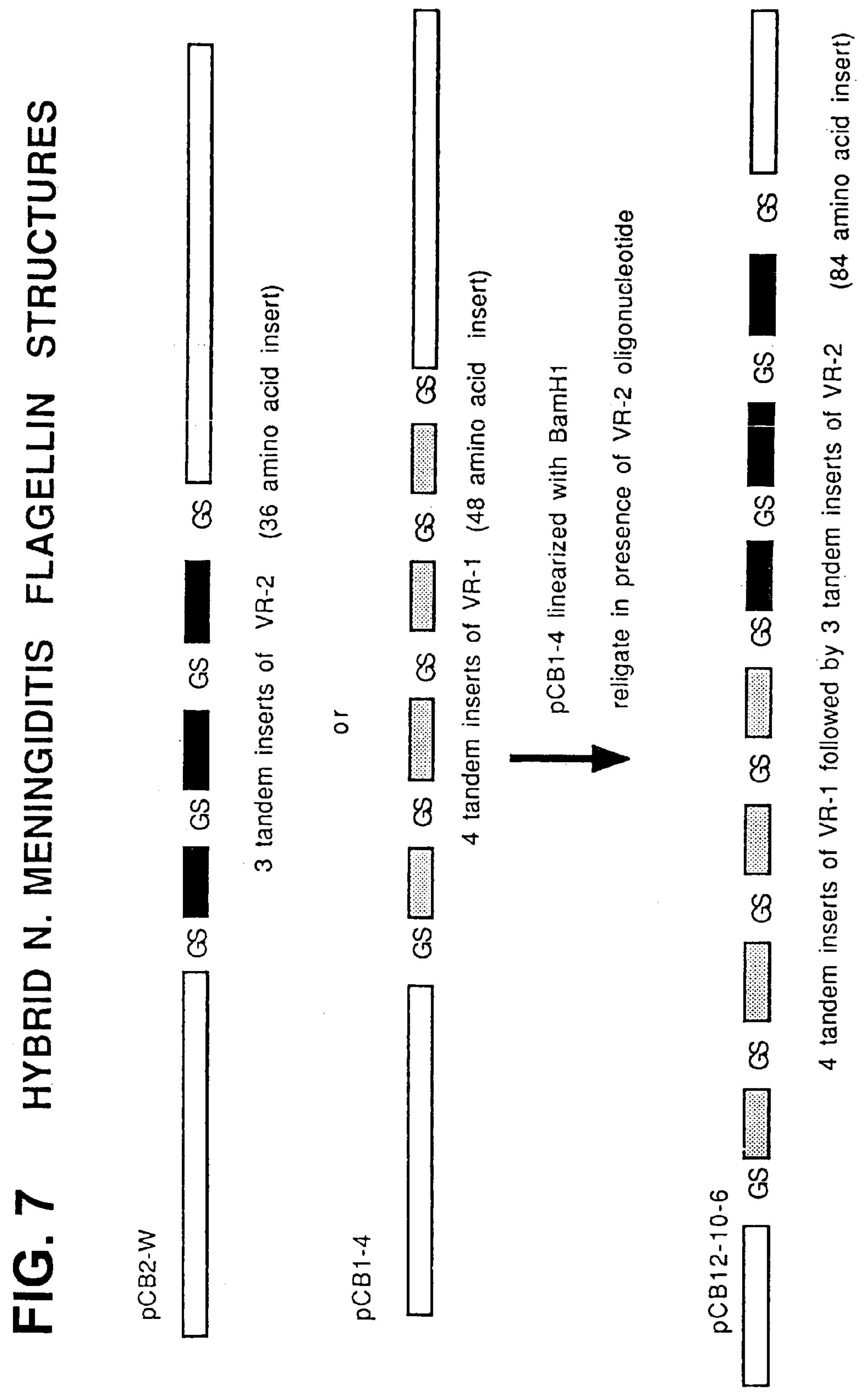
FIG. 7 HYBRID N. MENINGIDITIS FLAGELLIN STRUCTURES
pCB2-W
GS
GS
GS
3 tandem inserts of VR-2 (36 amino acid insert)
or
pCB1-4
GS
GS
GS
GS
GS
4 tandem inserts of VR-1 (48 amino acid insert)
pCB1-4 linearized with BamH1
religate in presence of VR-2 oligonucleotide
pCB12-10-6
GS
GS
GS
GS
GS
GS
GS
GS
4 tandem inserts of VR-1 followed by 3 tandem inserts of VR-2 (84 amino acid insert)

FIG. 8. A representative HPLC of purified pCBI2-10-6 showing a single major peak
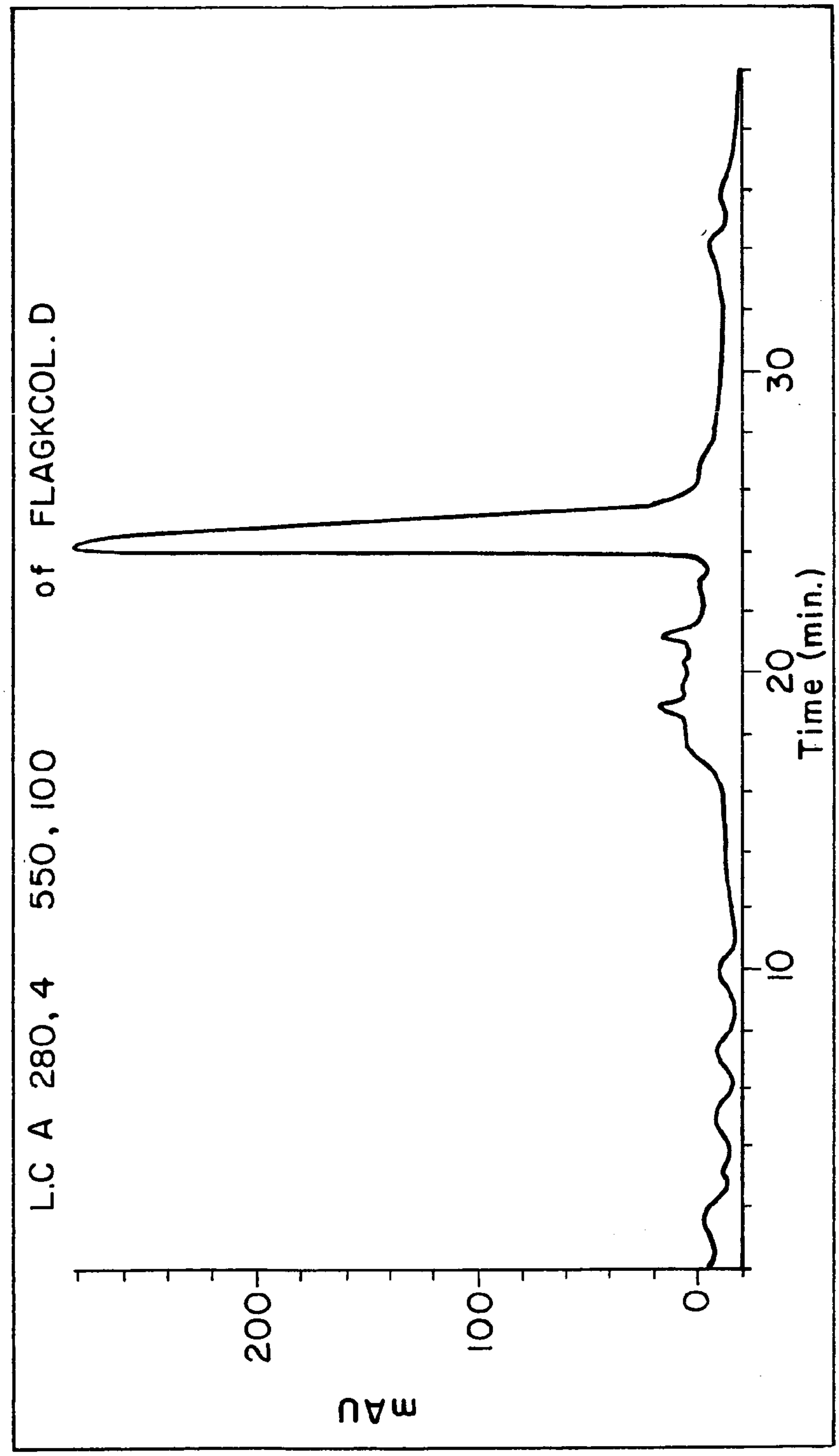

A representative SDS-Page of pCB12-10-6.

| Lane# | Sample |
|---|---|
| 1 | Blank |
| 2 | High Molecular Weight Standard |
| 3 | Dialyzed pCB12-10-6, Step 2 |
| 4 | Fractions off peak pCB12-10-6 |
| 5 | Purified pCB12-10-6 from HPLC,dialyzed in PBS, 20 μg |
| 6 | Purified pCB12-10-6 from HPLC,dialyzed in PBS, 1 μg |
| 7 | LPS - 5828 |
| 8 | Blank |
| 9 | High Molecular Weight Standard |
| 10 | Blank |

Photographs of representative western blot analysis of CB1 and CB2 CRM197 conjugates.

| Lane# | Sample |
|---|---|
| 1 | Molecular Weight Standard |
| 2 | M20-CRM, 10 μg |
| 3 | M20-CRM, 20 μg |
| 4 | Molecular Weight Standard |
| 5 | M21-CRM, 1 μg |

PUTATIVE CONFORMATION MENINGOCOCCAL CLASS I OUTER-MEMBRANE PROTEIN PL.16

(SEQ ID NO:5)

MENINGOCOCCAL CLASS 1 OUTER-MEMBRANE PROTEIN VACCINE

This application is a file wrapper continuation of application Ser. No. 07/691,005, filed Aug. 22, 1991, now abandoned, which is a national stage 371 application of PCT/US89/05678, filed Dec. 19, 1989 and claims foreign priority to the Netherlands applications 89.01612 filed Jun. 26, 1989, 89.00036 filed Jan. 6, 1989, and 88.03111 filed Dec. 19, 1988

BACKGROUND OF THE INVENTION

Bacterial meningitis is an inflammatory disease of the central nervous system caused by the growth of bacteria in and adjacent to the leptomeninges. Meningitis is an acute infectious disease which affects children and young adults and is caused by the *Neisseria meningitidis*, amongst other agents including other bacterial and viral pathogens.

Meningococci are subdivided into serological groups depending on the presence of either capsular or cell wall antigens. Currently recognized sero-groups include A, B, C, D, W-135, X, Y, Z, and 29E as segregated by seroagglutination. The polysaccharides responsible for the serogroup specificity of the group A, B, C, X, W-135 and Y have been purified.

The carrier rate for meningococci is much higher than the incidence of the disease. Some persons are temporary carriers, while others are chronic carriers, discharging meningococci either more or less continuously or in a sporadic fashion. The meningococcal carrier state is an immunizing process, and within two weeks of colonization, production of antibodies to meningococci can be identified. It appears that bactericidal antibodies are directed against both the capsular polysaccharide and other cell wall antigens.

Studies have shown that meningococcal outer membranes have three to five major proteins, with the predominant 41,000 Mr or 38,000 Mr proteins carrying the serotype specific determinants. There is a considerable degree of interstrain heterogeneity in the profiles of the outer membrane proteins on sodium dodecyl sulfate-polyacrylamide electrophoretic gels (SDS-PAGE). As defined by peptide mapping studies, the proteins comprise five classes, designated 1 through 5, based upon common peptide structures. Bactericidal monoclonal antibodies have been produced against the 46,000 Mr Class 1 proteins which are shared to some extent among strains of different serotypes. (Frasch, C. E. et al., (1985) pg. 633, "New Developments in Meningococcal Vaccines", in G. K. Schoolnik et al. (ed.) *The Pathogenic Nisseriae*, American Society for Microbiology, Washington, D.C.).

The capsular polysaccharide of groups A, C, W-135 and Y meningococci have been used to develop vaccines against the organism. Although these vaccines have been effective in the short term, they do not induce immunological memory and subjects must be revaccinated within approximately 3 years to maintain their resistance. The group B polysaccharide is poorly immunogenic and successful vaccines have not been produced. A possible explanation for the low activity may be due to tolerance to the group B polysaccharide induced by crossreactive antigens found in human tissues such as the brain. Furthermore, studies show that most of the bactericidal antibodies in the convelescent sera of patients who have had group B meningococcal disease are directed against outer membrane proteins.

Vaccines for protecting against group B meningococcal disease have been developed in which noncovalent complexes of outer membrane proteins (OMP) and group B polysaccharide were administered. Beuvery, et al. (1983) *Infect. Immun.* 40:369–380. However, the B polysaccharide is known to induce a transient IgM antibody response, which does not confer immunoprotection. Furthermore, there is great antigenic diversity and variability in the meningococci outer membrane proteins from strain to strain. Additionally, lipopolysaccharides are present in the OMP and exhibit antigenic variability as well.

There is a need for safe and effective vaccines against meningococcal disease which provide immunity from infection, particularly in infants and the elderly.

SUMMARY OF THE INVENTION

This invention pertains to isolated outer membrane vesicles (OMV's), to substantially purified Class 1 outer membrane protein (OMP) of *Neisseria meningitidis*, to fragments of the Class 1 OMP and to oligopeptides derived from the Class 1 OMP which contain continuous or discontinuous, immunogenic and protective B cell epitopes reactive with bactericidal antibodies against *N. meningitidis* and to the use of isolated OMV'S, the meningococcal Class 1 OMP, fragments or oligopeptides for vaccination against *N. meningitidis*.

The isolated OMV's, meningococcal Class 1 OMP, fragments or oligopeptides derived therefrom can be used in univalent or multivalent subunit vaccines alone, in mixtures, or as chemical conjugates or genetic fusions. In preferred vaccines, epitopes from different epidemiologically relevant meningococcal strains are used. In addition, isolated OMV's, the Class 1 OMP, fragments or oligopeptides can be used in conjunction (as mixtures, fusion or conjugates) with other antigens of *N. meningitidis*. For example, they can be used in conjunction with capsular polymers or oligomers (or fragments thereof) of *N. meningitidis* or with Class outer membrane proteins (or epitopes thereof) of different subtypes. In addition, they can be used with antigens of other infectious bacteria, viruses, fungi or parasites. Class 1 OMP T cell epitopes also are defined and these can be used in conjunction with other vaccine components to enhance the protective immune response to the vaccines.

This invention also pertains to the methods of producing isolated OMV's, the Class 1 OMP, fragments and oligopeptides and to various vaccine formulations containing them. The isolated OKV's Class 1 OMP can be produced by mutant meningococcal strains which do not express the Class 2/3 outer membrane protein. Fragments can be produced by cyanogen bromide cleavage and subsequent purification. Isolated OMV's, the Class I OMP, fragments or oligopeptides can be produced by recombinant DNA techniques, chemical synthesis or chemical or enzymatic cleavage. These materials, in turn, can be conjugated or fused to carrier peptides or proteins, to other antigens of *N. meningitidis* or to antigens of other microorganisms by chemical or genetic coupling techniques to produce multivalent antigenic conjugates and fusion peptides or proteins. They can be modified for conjugation such as by the addition of amino acids or other coupling groups. For vaccination, isolated OMV's, the Class 1 OMP, fragments or oligopeptides, in any of the forms described, can be formulated in pharmaceutically acceptable vehicles with optional additives such as adjuvants.

This invention also pertains to isolated nucleic acids which encode Class 1 OMP, fragments or oligopeptides. The nucleic acids can be incorporated into appropriate expression systems for production of isolated OMV's, Class 1

OMP, fragments or any oligopeptides derived therefrom. These nucleic acids can be modified as genetic fusions to contain sequences encoding additional polypeptides useful in enhancing the immune response to the vaccine formulation containing the expressed fusion polypeptides. In addition, Class 1 OMP of *N. meningitidis* is homologous in amino acid sequence and structure to porin proteins of other gram negative pathogens and thus the Class 1 OMP, fragments and oligopeptides of this invention allow for the development of vaccines for other gram negative pathogens.

BRIEF DESCRIPTION OF THE FIGURES

FIG. 2 (see also SEQ ID NOS 61–74). 5' gene sequences encoding VR1 (first variable region) of Class 1 outer membrane proteins of several *N. meningitidis* subtypes.

FIGS. 3A–3C (see also SEQ ID NOS 75–84). 3' gene sequences encoding VR2 (second variable region) of Class 1 outer membrane proteins of several *N. meningitidis* subtypes.

FIG. 6 (see also SEQ ID NOS 182–188). Construction of recombinant flagellins expressing variable region epitopes of *N. meningitidis* Class 1 OMP subtype P1.6, 16.

FIG. 7. Structure of recombinant flagellins expressing variabvle region epitopes of *N. meningitidis* Class 1 OMP subtype P1.6, 16.

FIG. 8. Representative chromotogram of high performance liquid chromatography of a recombinant flagellin.

DETAILED DESCRIPTION OF THE INVENTION

Figure 1:
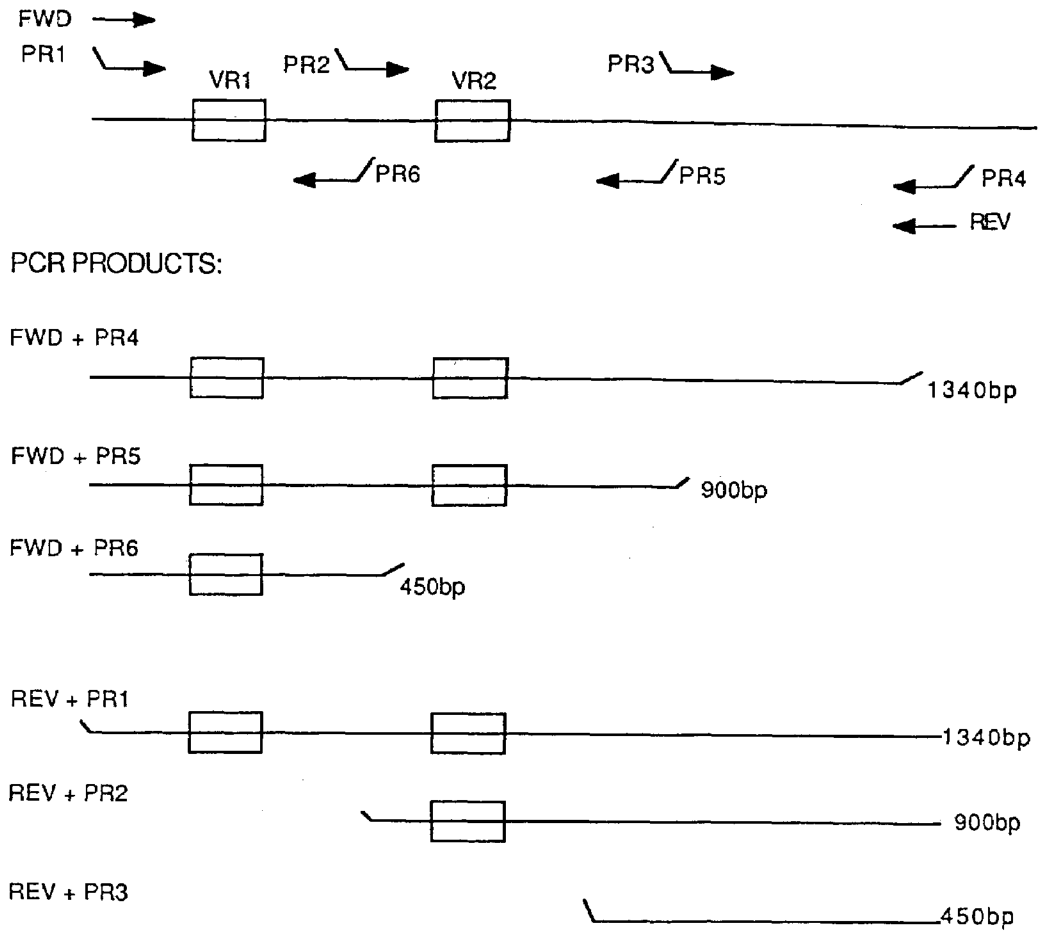
FIG. 1. Scheme for amplification of genes encoding meningococcal Class 1 outer membrane protein by PCR (Polymerase Chain Reaction).
Figures 4A, 4B, 4C, 4D:
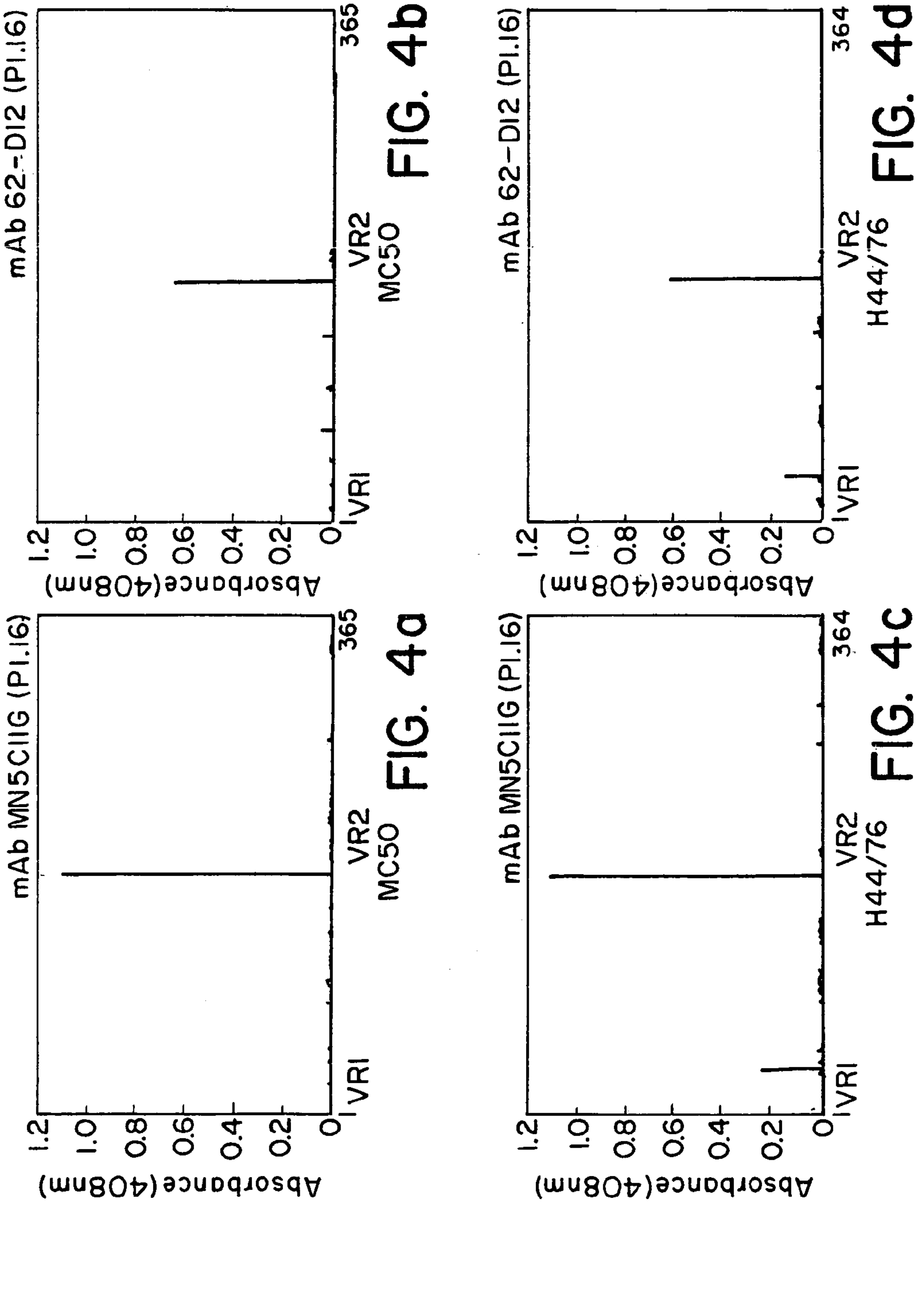
FIGS. 4*a*, 4*b*, 4*c*, 4*d*, 4*e*, 4*f*, 4*g* and 4*h*. Epitope scanning by reaction of monoclonal antibodies with solid phase decapeptides spanning the predicted amino acid sequences of Class 1 proteins from strains P1.7,16, P1.16 and P1.15. Adjacent decapeptides differ by five amino residues. Annotations show the strain from which the sequence was derived, the mAb used and its subtype specificity.
Figure 4E:
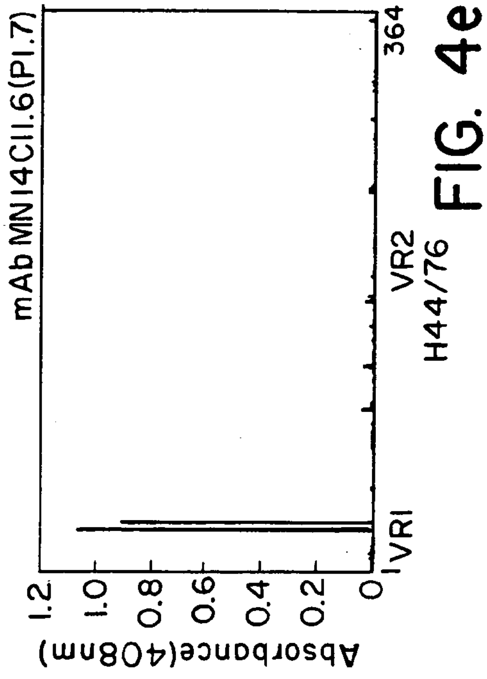
Figure 4F:
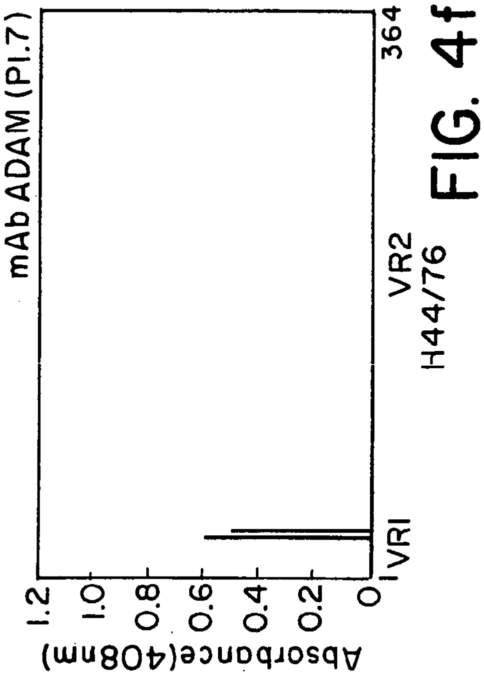
Figure 4G:
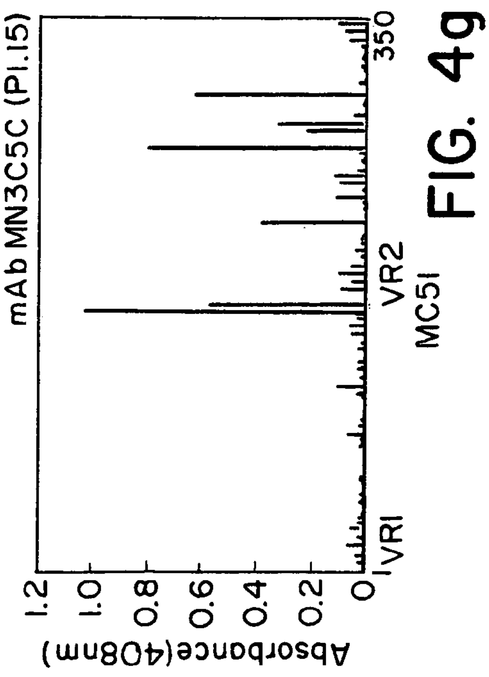
Figure 4H:
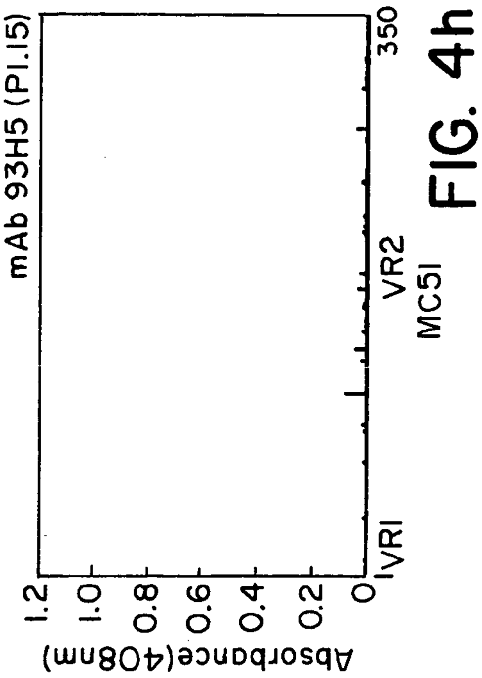
Figure 5A:
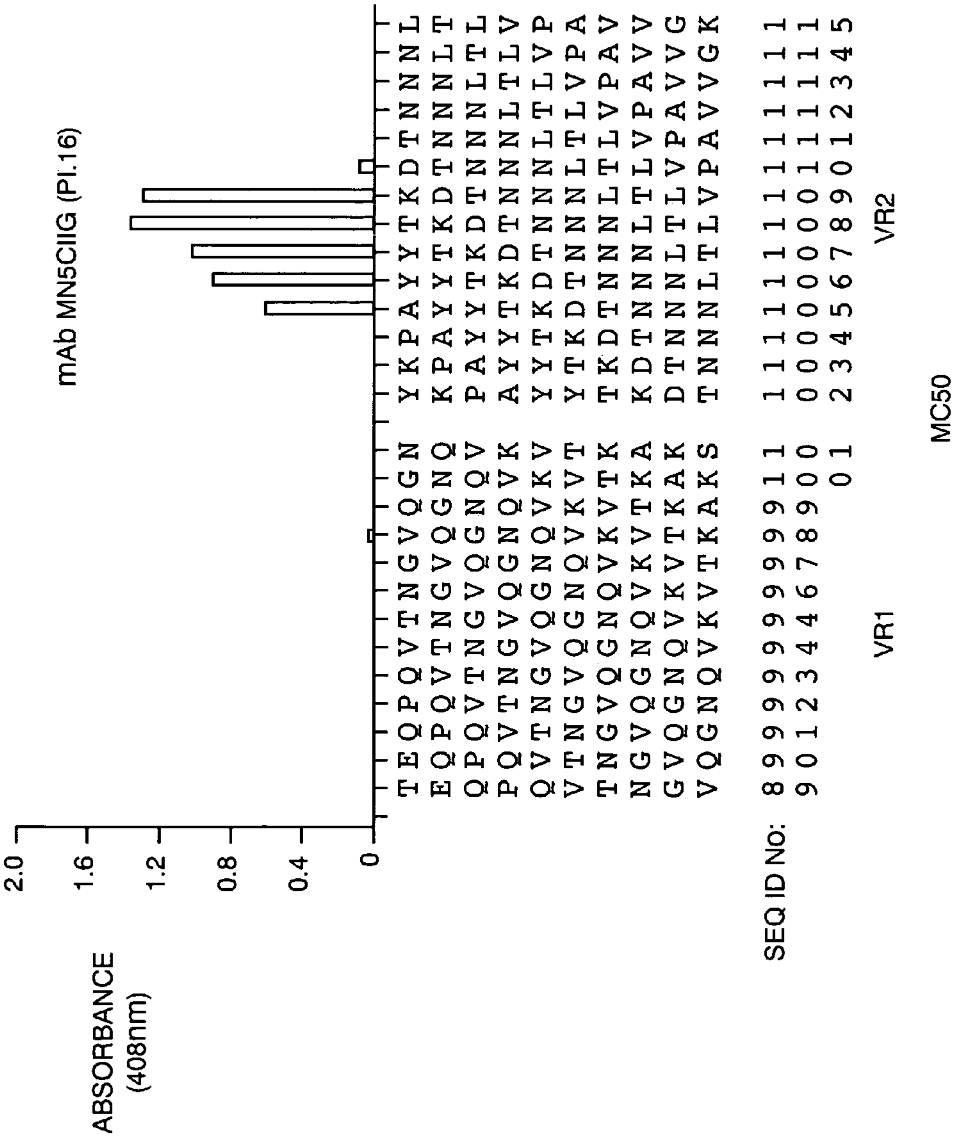
FIGS. 5*a*, 5*b*, 5*c*, 5*d*, 5*e*, 5*f*, 5*g* and 5*h* (see also SEQ ID NOS 89–181). Reaction of the monoclonal antibodies with series of overlapping decapeptides corresponding to variable regions VR1 and VR2, with adjacent peptides differing by a single amino acid residue. Annotations show the strain from which the sequence was derived, the mAb used and its subtype specificity.
Figure 5B:
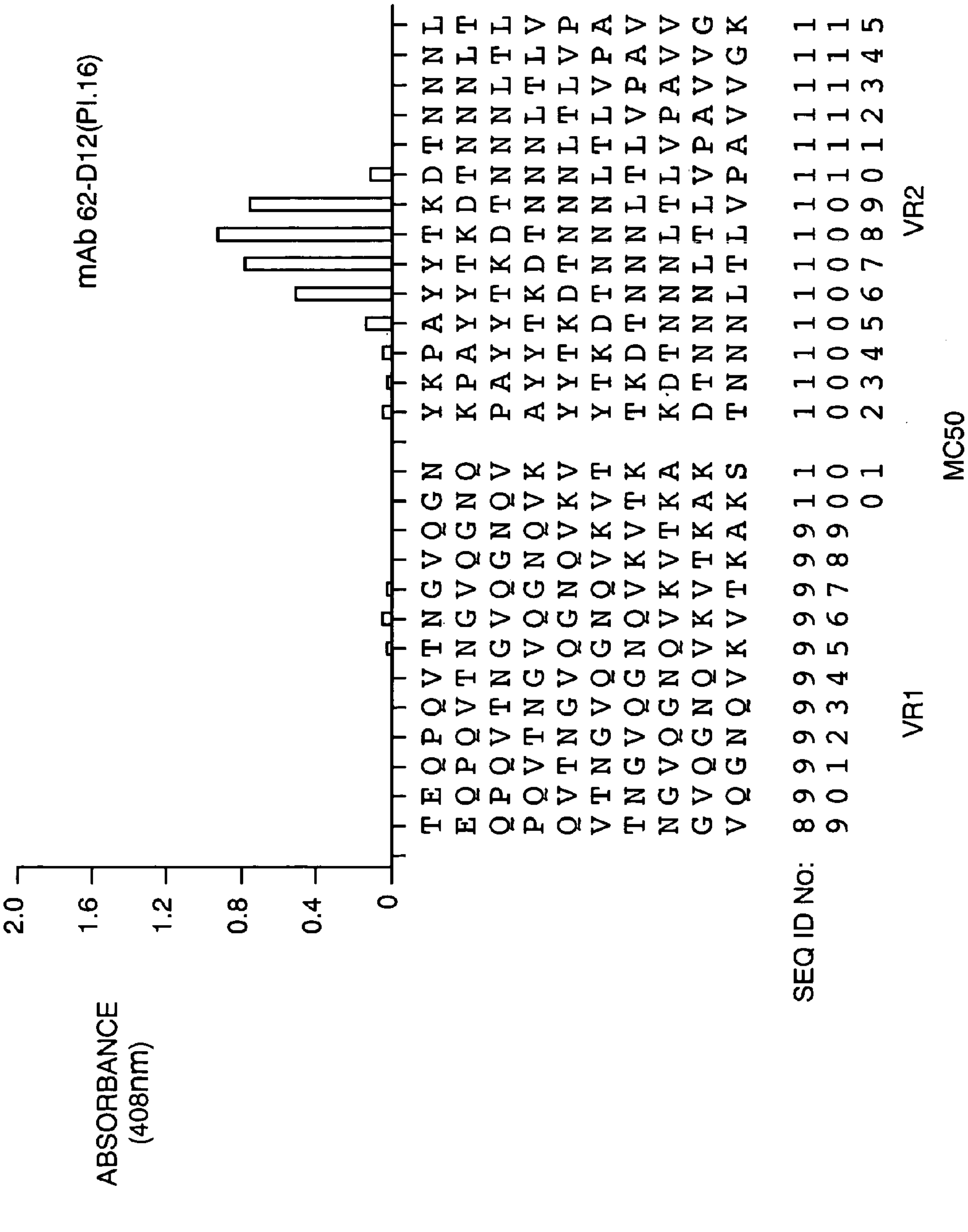
Figure 5C:
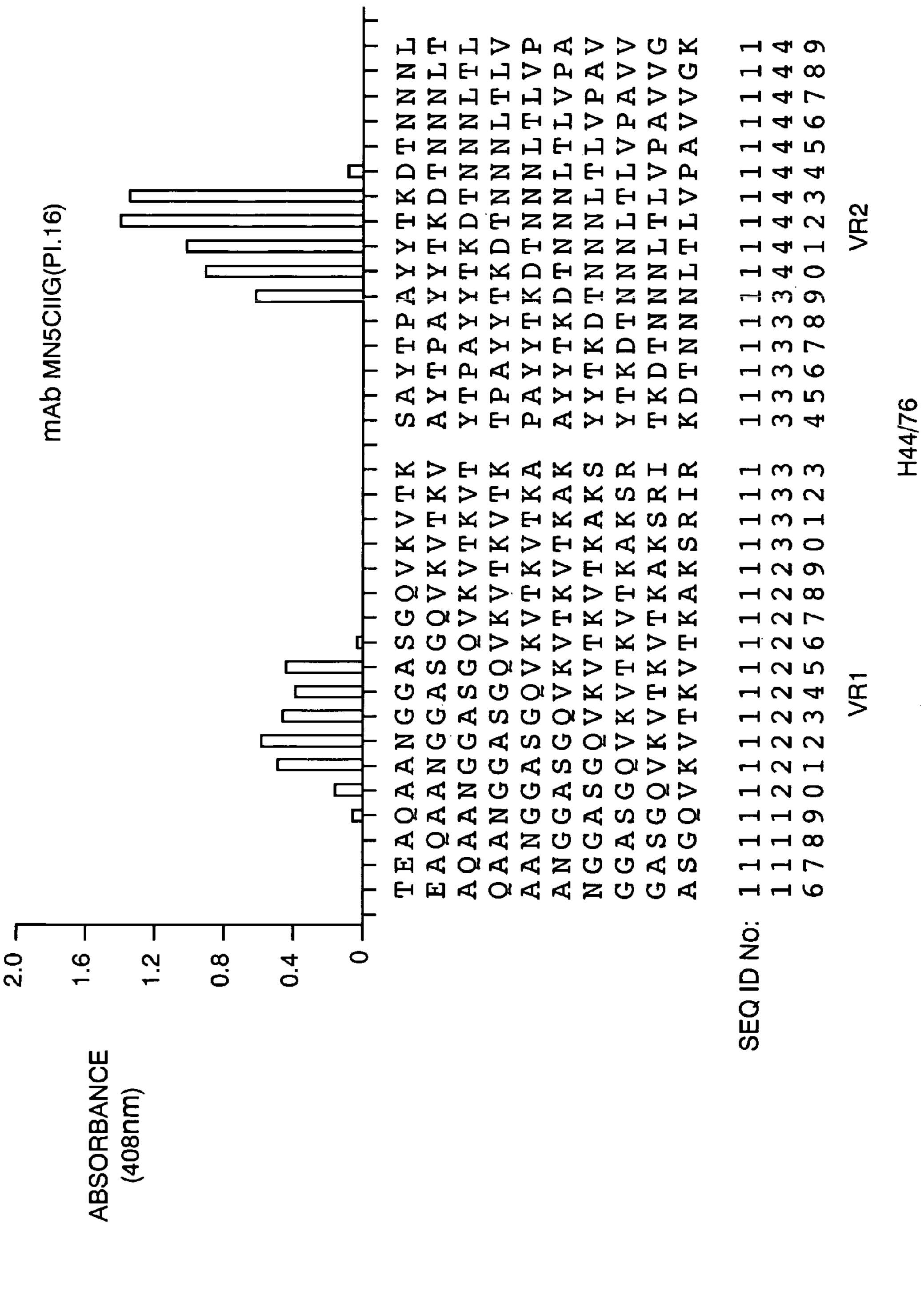
Figure 5D:
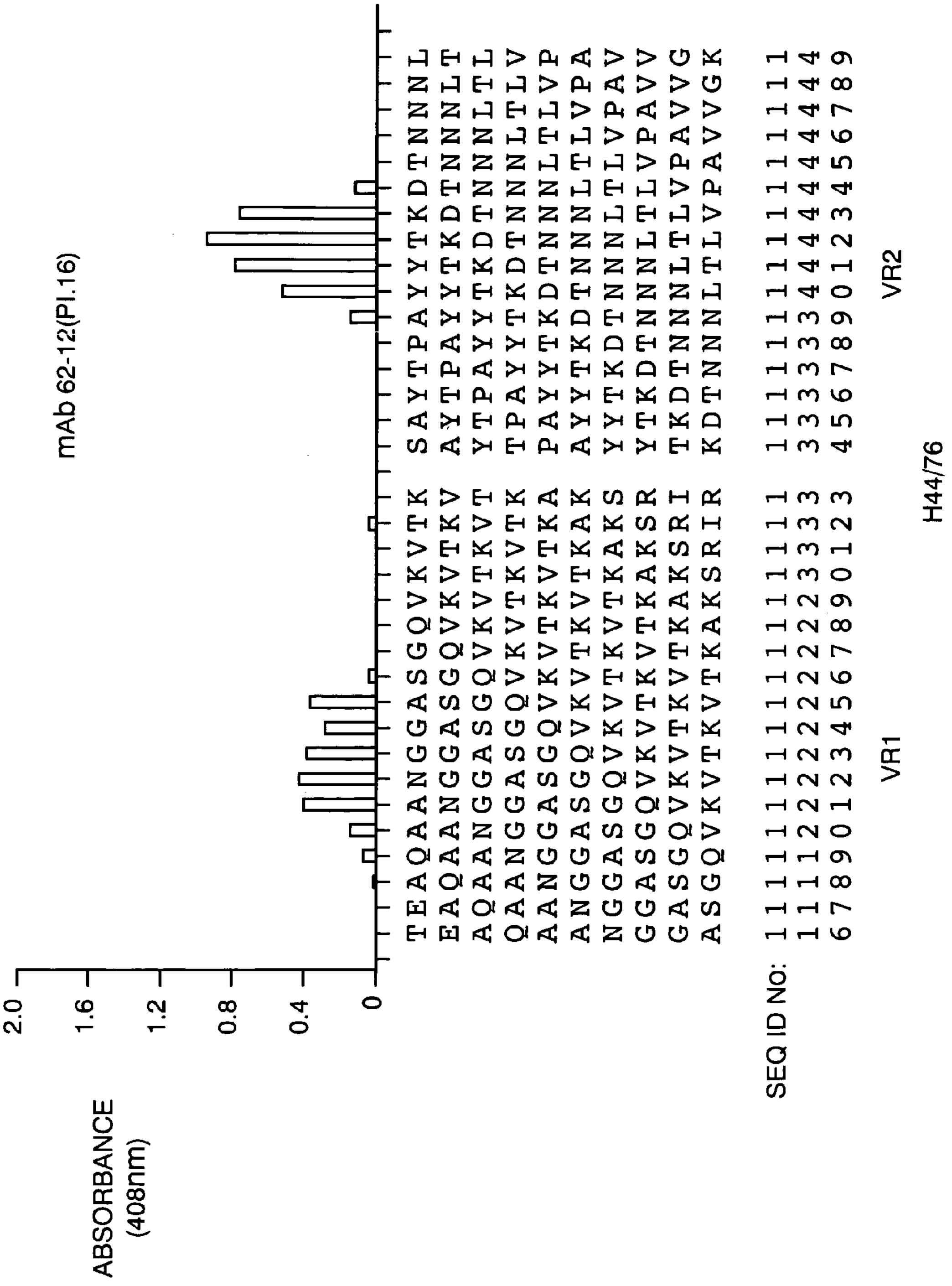
Figure 5E:
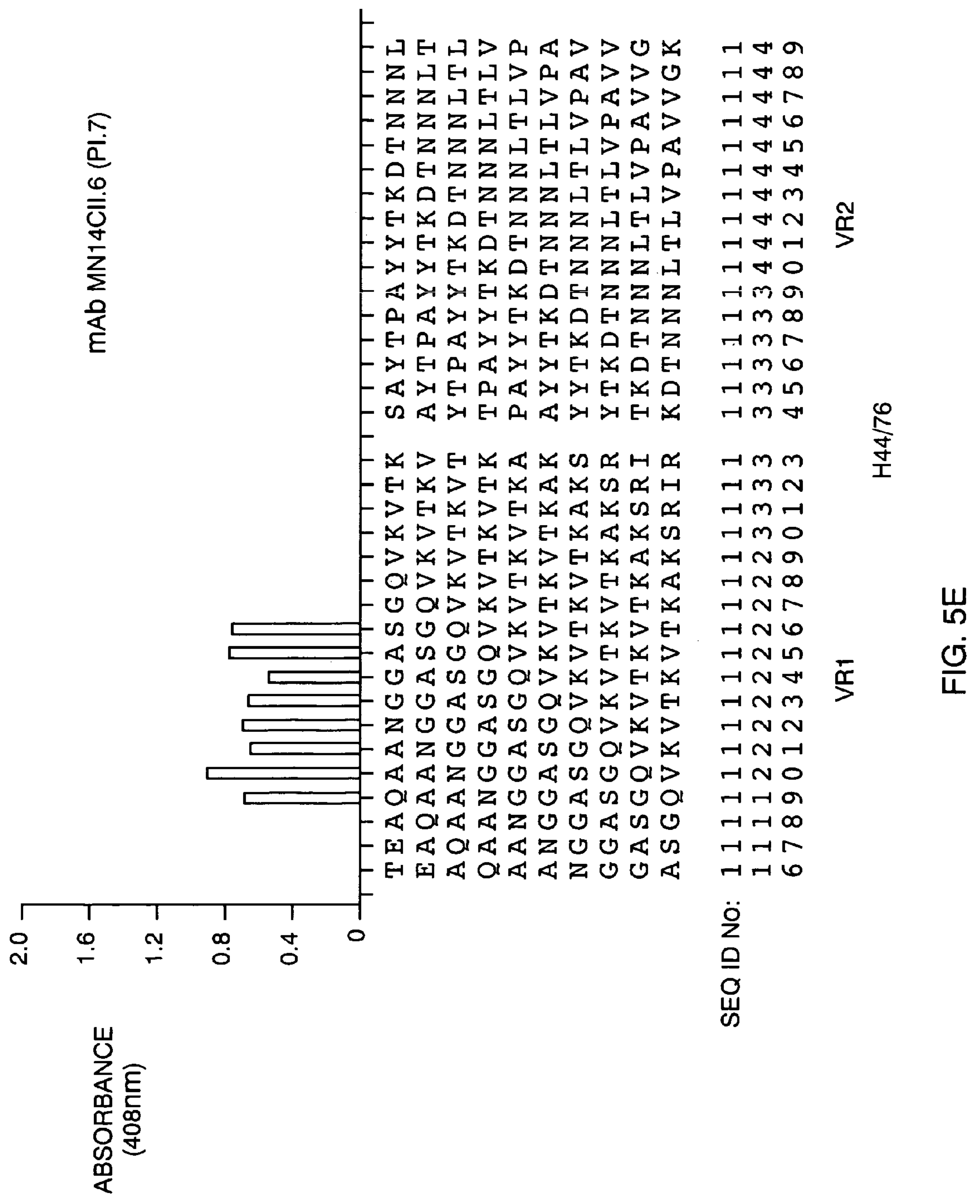
Figure 5F:
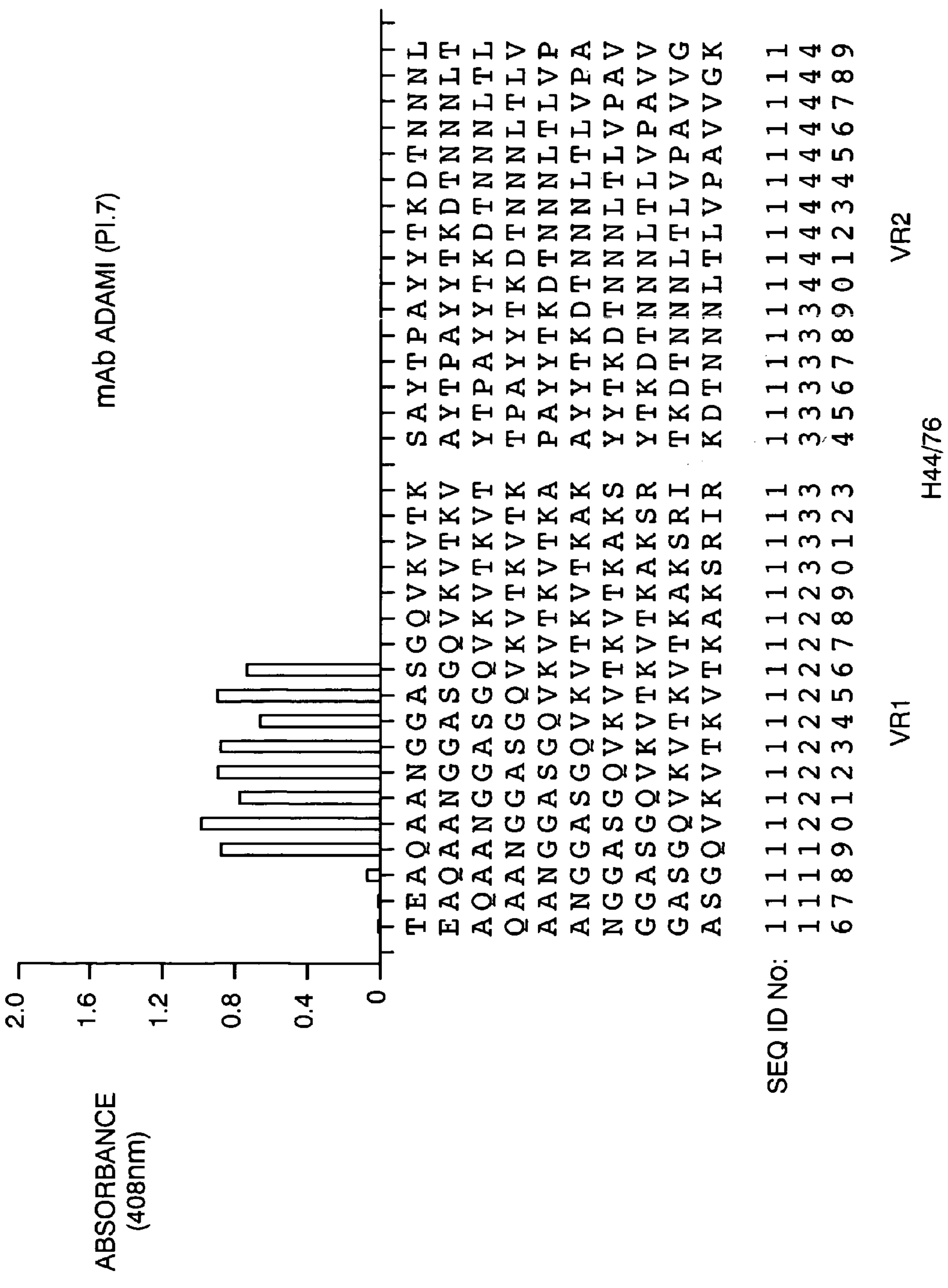
Figure 5G:
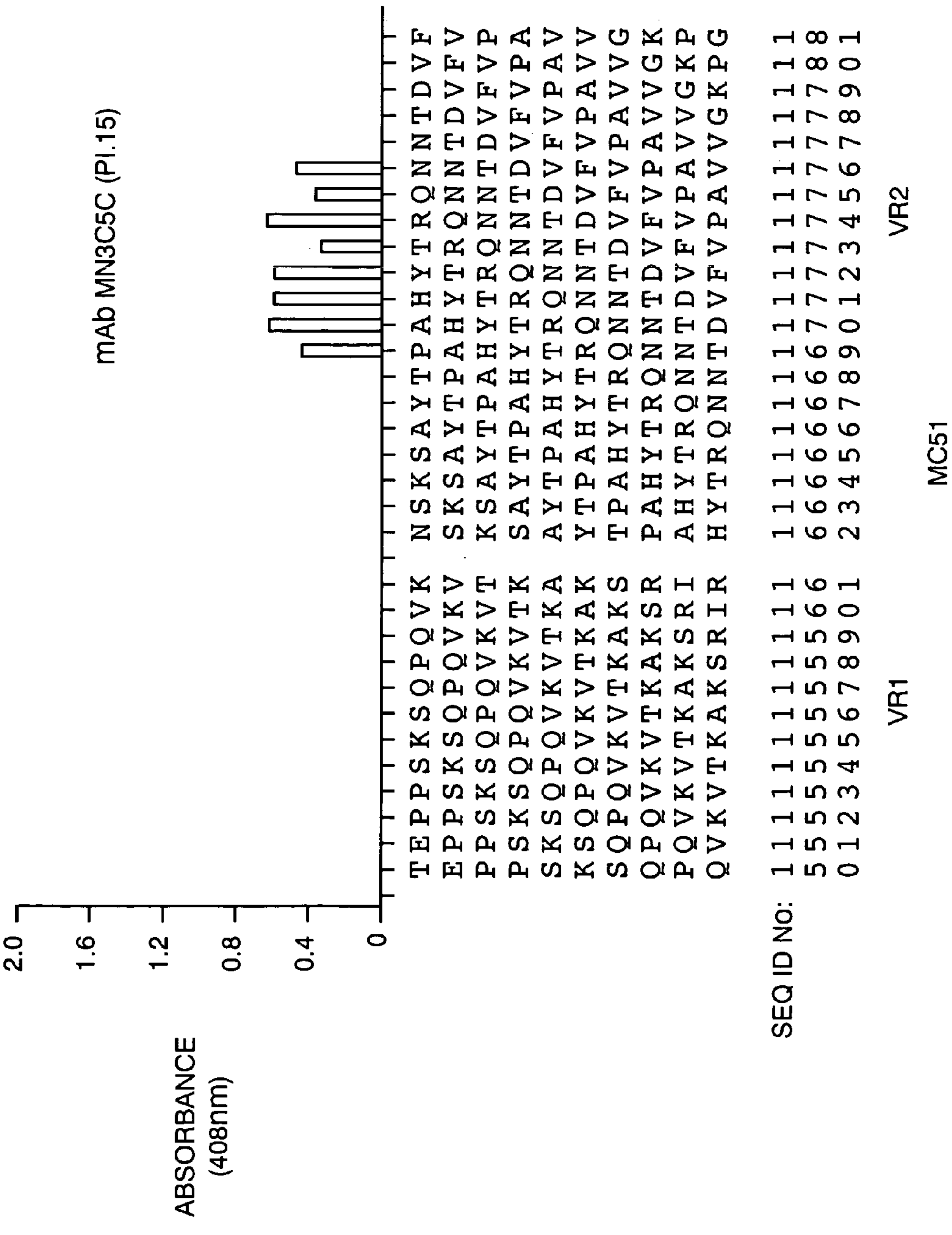
Figure 5H:
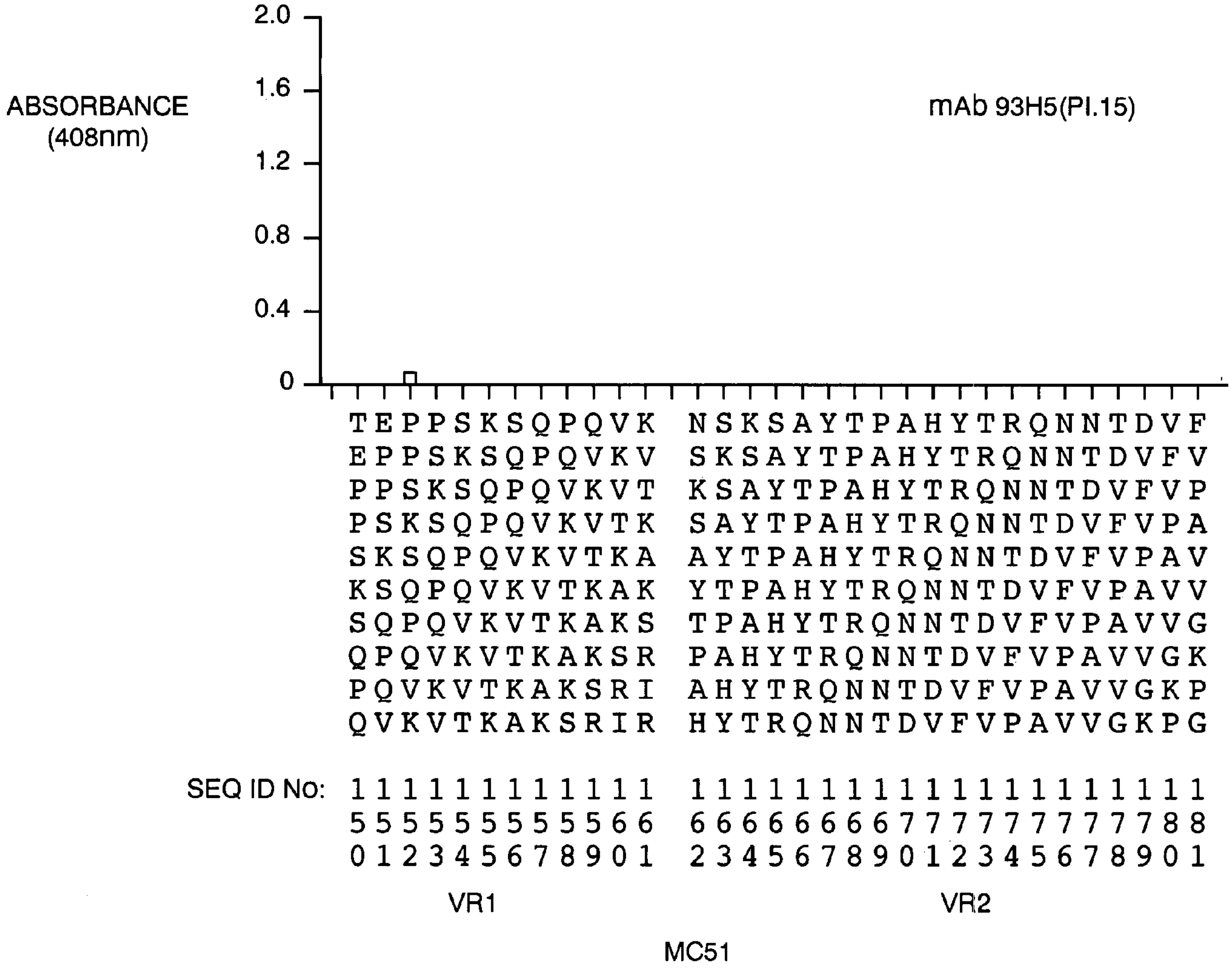

This invention pertains to vaccines comprising isolated OMV's, meningococcal Class 1 OMP, fragments of the OMP (e.g., prepared by the application of cyanogen bromide) and oligopeptides bearing epitopes of the OMP; the preparation of isolated OMV's, pure Class 1 outer-membrane proteins, using mutant strains which do not express the Class 2/3 outer-membrane protein; the preparation of isolated OMV's pure Class 1 outer-membrane proteins with the aid of cloned DNA in recombinant DNA expression vectors. This invention also comprises the application of genetic engineering with the object of producing isolated OMV's Class 1 OMP or portions thereof, genetic fusions of Class 1 OMP, portions or epitopes therof; and the preparation of multivalent Class 1 outer-membrane vaccine through peptide synthesis, as the epitopes with a short peptide chain can be synthetically prepared.

It has emerged that meningococcal Class 1 outer-membrane proteins induce a strong bactericidal immune response to the strains containing the appropriate subtype epitopes, irrespective of whether these are from group A, B, C, W-135, and Y strains. The polysaccharide vaccine can be enhanced or replaced by a vaccine according to the invention as a vaccine with broad, extensive action again most serotypes. The protective bactericidal monoclonal antibodies specific for the Class 1 outer-membrane protein react strongly with fragments that have been split off and short synthetic peptides which have been prepared using the amino acid sequence of Class 1 outer-membrane proteins. Since meningococcal disease is currently caused chiefly by group B meningococci and because the Class 1 outer-membrane proteins occurring in group B meningococci also occur in group A, C, W-135, and Y meningococci, vaccines of this invention which comprise one or more Class 1 OMP epitopes derived from *N. meningitidis* group B should be effective in preventing disease caused by group A, C, W-135 and Y. Preferably, the preparation of such a vaccine starts from at least two different immunogenic and protective epitopes which have been selected on epidemiological grounds. Vaccines according to the invention comprise, for example, at least one protein which is obtained either in OMV formulation or by purification from mutant strains producing one or more Class 1 OMP or at least two fragments prepared through a cyanogen bromide fragmentation or at least two synthetic peptides, chosen from about 10 major epitopes, or products obtained by gene expression via recombinant DNA technology, which contain the desired epitopes. To maximize efficacy to a broad range of meningococcal strains, the greater number of different protective epitopes in the vaccine the better. In addition, the vaccines according to the invention may advantageously contain meningococci A and C or optionally W-135 and Y polysaccharides and/or detergents. Preferably, the A and C polysaccharides are covalently coupled to a protein or polypeptide carrier. These carriers include, for example, isolated OMV, the Class 1 OMP protein, T-helper epitopes, bacterial toxins, toxoids, nontoxic mutants (CRM's), recombinant *Salmonella* flagellin and viral particles such as rotavirus VP6 protein, Hepatitis B surface antigen or parvovirus VP 1 and VP2 proteins. Both zwitterionogenic, cationogenic, anionogenic and nonionogenic detergents can be used. Examples of such detergents are ZWITTERGENT 3-10, ZWITTERGENT 3-14 (N-tetradecyl-N,N-dimethyl-3-ammonia-1-propane sulphonate), TWEEN 20, sodium deoxycholate, sodium cholate and octylglucoside. The vaccines according to the invention may also contain an adsorbent such as aluminium hydroxide, calcium phosphate; or advantageously, aluminium phosphate. The fragments, proteins, and peptides can also be processed in immuno-stimulating complexes (ISCOMS), liposomes or microspheres for delivering and/or use as an adjuvant or in connection with other adjuvants so that greater immunogenicity is obtained.

This invention encompasses isolated OMV, substantially pure meningococcal Class 1 outer membrane proteins (of any subtype) and fragments of the proteins containing epitopes thereof. The fragments can be any portions of the molecular weight of 25 kD or less which contain epitopes which are bound by protective bactericidal antibodies against *N. meningitidis*. These include proteolytic fragments and synthetic oligopeptides which are comprised of amino acid sequences which correspond, at least in part, to epitopes of a Class 1 OMP.

The isolated OMV's, Class 1 OMP, fragments or epitope-containing oligopeptides derived therefrom can be comprised of amino acid sequences which are different, but essentially biologically equivalent to the natural sequences. These sequences can include sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar-(hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The charged (basic) amino acids include arginine, lysine and histidine. The negatively charged (acidic) amino acids include aspartic and glutamic acids.

Additionally, isolated OMV's, the Class 1 OMP, fragments or the oligopeptides can be modified for conjugation to other molecules (e.g., by the attachment of coupling groups such as the amino acids cysteine and/or lysine or other linking groups and/or spacer groups) including other Class 1 OMP of a different subtype, T cell epitopes, B cell epitopes, carrier peptides or proteins or adjuvanting molecules.

As described in detail below, the Class 1 OMP. fragments or oligopeptides can be used in many different forms (e.g., alone, in mixtures, or as conjugates and genetic fusions produced from recombinant DNA vectors) in vaccines. For these purposes, the materials can be produced by isolation from *N. meningitidis*, by proteolytic digestion, by chemical synthesis, or by expression as recombinant molecules. The methods of production and use of the isolated OMV's, the Class 1 OMP and the fragments and the oligopeptides of Class 1 OMP are described below.

Protein modeling and structure analysis of the Class 1 OMPs were performed using the principles for several *E. coli* outer membrane proteins. (Vogel, H. et al., *J. Mol. Bio.,* 190:191 (1986); Ference, T. et al., *J. Mol. Bio.,* 201:493 (1988) and Tommassen, J. in "Membrane Biogenesis", *NATO ASI Series H*16, pp351, Springer-Verlag, NY (1988)). The derived amino acid sequence of the Class 1 OMPs were used for the modeling studies and comparison. The amino acid sequence homology was compared to other gram negative bacterial porin proteins and similarity was established for the protein structure. Exposed surface loops and transmembrane structure were very similar for these porin proteins. With the information revealed concerning variable and constant region protective epitopes of *N. meningitidis* and their structure, one can predict based upon the amino acid sequence where protective epitopes may reside for other pathogenic gram negative bacteria to be evaluated and included in vaccines for the same.

Production of Isolated OMV's

OMV's can be produced either from the culture supernatant or from the bacterial cells after fragmentation as described by Beuvery et al. (1983) loc. cit. OMV's carrying proteins from more than one meningococcus can be isolated from strains manipulated to express heterologous proteins.

Production and Purification of Class 1 OMP and CNBr Fragments Thereof

Class 1 and Class 3 outer membrane proteins can be isolated as described by Beuvery, E. C. et al., *Antonie wan Leeuvenhoek J. Microbiol.* 52:232 (1986). The production of substantially pure Class 1 OMP free of Class 2 or 3 OMP's is achieved by this method using mutant meningococcal strains which do not express Class 2/3 OMP. A preferred strain for production of Class 1 OMP is the HIII5 strain, deposited as CBS 636.89.

Fragments can be produced by cyanogen bromide cleavage as described by Teerlink T. et al., *J. Exp. Med.* 166:63 (1987) for a gonococcal protein. The N-terminal fragment is referred to as CB-1 and the C-terminal fragment is referred to as CB-2. These CNBr fragments can be purified via reverse phase HPLC on a Vydax™ C4 or an Aquapor™ R-300 column using a water/acetonitrile gradient. Alternatively, the fragment can be purified by multiple cold trichloroacetic acid precipitations. These procedures remove greater than 95% of interferring contaminants (e.g., buffer salts, detergents and fragment contaminants).

Preparation of Fragments and Oligopeptides Containing Epitopes of Class 1 OMP

A. Preparation by Proteolytic Digestion

Oligopeptides containing epitopes reactive with bactericidal antibodies against *N. meningitidis* can be produced by digestion of the Class 1 OMP, CB-1 or CB-2 fragments with proteinases such as endoLys-C, endoArg-C, endoGlu-C and staphylococcins V8-protease. The digested fragments can be purified by, for example, high performance liquid chromatographic (HPLC) techniques.

B. Preparation by Chemical Synthesis

Oligopeptides of this invention can be synthesized by standard solid peptide synthesis (Barany, G. and Merrifield, R. B., *The Peptides* 2:1–284, Gross, E. and Meienhofer, J., Eds., Academic Press, New York) using tert-butyloxycarbonyl amino acids and phenylacetamidomethyl resins (Mitchell, A. R. et al., *J. Org. Chem.* 43:2845–2852 (1978)) or 9-fluorenylmethyloxycarbonyl amino acids on a polyamide support (Dryland, A. and Sheppard, R. C., *J. Chem. So. Perkin Trans. I,* 125–137 (1986)). Alternatively, synthetic peptides can be prepared by pepscan synthesis (Geysen, H. M. et al., *J. Immunol. Methods* 03:259 (1987); *Proc. Natl. Acad. Sci. USA* 81:3998 (1984)), Cambridge Research Biochemicals, Cambridge, U.K. or by standard liquid phase peptide synthesis. The deletion or substitution of amino acids (and including extensions and additions to amino acids) in other ways which do not substantially detract from the immunological properties of the oligopeptide.

C. Preparation by Recombinant DNA Techniques

The Class 1 OMP, fragments and oligopeptides which exhibit epitopes of the Class 1 OMP can be produced by recombinant DNA techniques. In general, these entail obtaining DNA sequences which encode the desired OMP, (Barlow et al., (1989) *Mol. Micro.,* 3:131) fragment or oligopeptide sequences and introducing into an appropriate vector/host expression system one or more similar or different DNA sequences of Class 1 OMP's where it is expressed. The DNA can consist of the gene encoding the Class 1 OMP or any segment of the gene which encodes a functional epitope of the OMP. The DNA can be fused to DNA encoding other antigens of *N. meningitidis* (such as other outer membrane proteins either of the same or different class) or antigens of other bacteria, viruses, parasites or fungi to create genetically fused (sharing a common peptide backbone), multi-valent antigens. For example, Class 1 OMP fragments can be fused to another Class 1 outer membrane protein of a different subtype (or fragments or epitopes thereof) of *N. meningitidis* to yield fusion proteins comprising multiple Class 1 outer membrane protein subtype determinants.

Genetic engineering techniques can also be used to characterize, modify and/or adapt the encoded peptides or proteins. For example, site directed mutagenesis to modify an OMP fragment in regions outside the protective domains, for example, to increase the solubility of the subfragment to allow easier-purification. DNA can also be manipulated to effect superproduction of OMP fragments or combinations thereof in various organisms.

DNA encoding a Class 1 OMP, fragments or oligopeptides can be synthesized or isolated and sequenced as described by Barlow, A. K. et al. *Infect. Immune* 55:2734–40 (1987) and Barlow, A. K. et al., *Mol. Micro.* 3:131 (1989). Class 1 OMP genes can be amplified from bacterial DNA by the methods of Mullis and Faloona, (1987) Method. Enzym. 155:335–350, using the primer sequences disclosed herein. Related DNA sequences for Class 1 OMP of different subtypes can be obtained by the procedures described and the amino acid sequences deduced.

A variety of host-vector systems can be used to express the oligopeptides of this invention. Primarily the vector system must be compatible with the host cell used. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

In order to obtain efficient expression of the cloned DNA, a promoter must be present in the expression vector. RNA polymerase normally binds to the promoter and initiates transcription of a gene or a group of linked genes and regulatory elements (called an operon). Promoters vary in their "strength", i.e., their ability to promote transcription. It is desirable to use strong promoters in order to obtain a high level of transcription and, hence, a high level of DNA expression. Depending upon the host cell system any one of a number of suitable promoters can be used. For instance, for *E. coli*, its bacteriophages or plasmids, promoters such as the lac promoter, trp promoter, recA promoter, ribosomal RNA promoter, and $P_R$ or $P_L$ promoters of coliphage lambda and others including but not limited to lacUV5, ompF, bla, lpp and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted DNA.

Bacterial host cells and expression vectors may be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, etc., are under different controls. The trp operon is induced when tryptophan is absent in the growth media; and the $P_L$ promoter of lambda can be induced by an increase in temperature in host cells containing a temperature sensitive lambda repressor, e.g., cI857. In this way, greater than 95% of the promoter-directed transcription may be inhibited in uninduced cells. Thus, expression of the recombinant peptide or protein can be controlled. This is important if the expression product of the DNA is lethal or detrimental to the host cells. In such cases, transformants may be cultured under conditions such that the promoter is not induced; then, when the cells reach a suitable density in the growth medium, the promoter can be induced for production of the protein.

One such promoter/operator system is the "tac" or trp-lac promoter/operator system (Russell and Bennett, 1982, Gene 20:2312–243; DeBoer, European Patent Application, 67, 540 filed May 18, 1982). This hybrid promoter is constructed by combining the −35 b.p. (−35 region) of the trp promoter and the −10 b.p. (−10 region or Pribnow box) of the lac promoter (the sequences of DNA which are the RNA polymerase binding site). In addition to maintaining the strong promoter characteristics of the tryptophan promoter, tac is also controlled by the lac repressor.

When cloning in a eukaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted DNA is less critical.

Specific initiation signals are also required for efficient gene transcription and translation in procaryotic cells. These transcription and translation initiation signals may vary in "strength" as measured by the quantitiy of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Any of the methods described for the insertion of DNA into an expression vector can be used to ligate a promoter and other genetic control elements into specific sites within the vector. *N. meningitidis* sequences for expression can be ligated into an expression vector at a specific site in relation to the vector promoter and control elements so that when the recombinant DNA molecule is introduced into a host cell the foreign genetic sequence can be expressed (i.e., transcribed and translated) by the host cell.

The recombinant DNA vector can be introduced into appropriate host cells (bacteria, virus, yeast, mammalian cells or the like) by transformation, transduction or transfection (depending upon the vector/host cell system). Host cells containing the vector are selected based upon the expression of one or more appropriate gene markers normally present in the vector, such as ampicillin resistance or tetracycline resistance in pBR322, or thymidine kinase activity in eucaryotic host systems. Expression vectors may be derived from cloning vectors, which usually contain a marker function. Such cloning vectors may include, but are not limited to the following: SV40 and adenovirus, vaccinia virus vectors, insect viruses such as baculoviruses, yeast vector, bacteriphage vectors such as lambda gt-WES-lambda B, Charon 28, Charon 4A, lambda gt-1-lambda BC, lambda gt-1-lambda B, M13 mp7, M13 mp8, M13 mp9, or plasmid DNA vectors such as pBR322, pAC105, pVA51, pACYC177, pKH47, pACYC184, pUB110, pMB9, pBR325, Col E1, pSCO101, pBR313, pML21, RSF2124, pCR1, RP4, pBR328 and the like.

Expression vectors containing the DNA inserts can be identified by three general approaches: (1) DNA-DNA hybridization using probes comprising sequences that are homologous to the inserted gene; (2) presence or absence of "marker" gene functions (e.g., resistance to antibiotics, transformation phenotype, thymidine kinase activity, etc.); and (3) expression of inserted sequences based on the physical immunological or functional properties of the gene product.

Once a putative recombinant clone which expresses a desired Class 1 OMP amino acid sequence is identified, the gene product can be analyzed as follows. Immunological analysis is especially important because the ultimate goal is to use the gene products in vaccine formulations and/or as antigens in diagnostic immunoassays. The expressed peptide or protein should be immunoreactive with bactericidal antibodies against *N. meningitidis*. This reactivity may be demonstrated by standard immunological techniques, such as radioimmuno-precipitation, radioimmune competition, ELISA or immunoblots.

Once the gene product is identified as a Class 1 OMP fragment or an oligopeptide containing a functional epitope thereof, it can be isolated and purified by standard methods including chromatography (e.g., ion exchange, affinity, and sizing column chromatography), centrifugation, differential solubility, or by any other standard techniques for the purification or proteins. Several techniques exist for purification of heterologous protein from prokaryotic cells. See e.g., Olson, U.S. Pat. No. 4,518,526, Wetzel, U.S. Pat. No. 4,599,197 and Hung et al., U.S. Pat. No. 4,734,362. The purified preparation however produced should be substantially free of host toxins which might be harmful to humans. In particular, when expressed in gram negative bacterial host cells such as *E. coli* or *Salmonella*, the purified peptide or protein should be substantially free of endotoxin contamination.

Class 1 OMP, fragments and oligopeptides of this invention can be formulated as univalent and multivalent vaccines. These materials can be used as produced or isolated by the methods described above. They can be mixed, conjugated or fused with other antigens, including B or T cell epitopes of other antigens. In addition, they can be conjugated to a carrier protein as described below for oligopeptides.

When a haptenic oligopeptide is used (i.e., a peptide which reacts with cognate antibodies, but cannot itself elicit an immune response), it can be conjugated to an immunogenic carrier molecule. Conjugation to an immunogenic carrier can render the oligopeptide immunogenic. The conjugation can be performed by standard procedures. Preferred carrier proteins for the haptenic oligopeptides are toxins, toxoids or any mutant crossreactive material (CRM) of the toxin from tetanus, diphtheria, pertussis, *Pseudomonas, E. coli, Staphylococcus*, and *Streptococcus*. A particularly preferred carrier is $CRM_{197}$ of diphtheria toxin, derived from *P. diphtheriae* strain C7 (β 197) which produces $CRM_{197}$ protein. This strain has ATCC accession no. 53281. Alternatively, a fragment or epitope of the carrier protein or other immunogenic protein can be used. For example, the hapten can be coupled to a T cell epitope of a bacterial toxin, toxoid or CRM. See U.S. patent application Ser. No. 150,688, filed Feb. 1, 1988, entitled "Synthetic Peptides Representing a T-Cell Epitope as a Carrier Molecule For Conjugate Vaccines", the teachings of which are incorporated herein. Other carriers include viral particles composed of Rotavirus VP6, Hepatitis B surface antigen or parvovirus VP1 and VP2. In a particular embodiment, an antigenic conjugate can comprise an oligopeptide selected from the group consisting of QPQVTNGVQGN (SEQ ID NO:22), PPSKSQP (SEQ ID NO:23), AQAANGGASG (SEQ ID NO:20), YYTKDTNNNLTL (SEQ ID NO:189), YYTKNTNNNLTL (SEQ ID NO:190), YYTKDTNNNL (SEQ ID NO:17), YYTKNTNNNL (SEQ ID NO:18), HFVQQTPQSQP (SEQ ID NO:21) and HYTRQNNTDVF (SEQ ID NO:19), and the carrier protein can be a bacterial toxin.

The peptides or proteins of this invention can be administered as multivalent subunit vaccines in combination with antigens of *N. meningitidis* or antigens of other organisms. Some of the other organisms include the pathogenic bacteria *H. influenzae, N. meningitidis, B. catarrhalis, N. gonorrheae, E. coli, S. pneumoniae*, etc. For example, they may be administered in conjunction with oligo- or polysaccharide capsular components of *N. meningitidis*. The capsular components can be derived from any of the serological groups, including A, B, C, D, X, Y, Z, 29E and W135.

Class 1 outer membrane proteins of different subtypes can be used. These may be used in combination to evoke bactericidal antibodies against *N. meningitis*. For example, a fragment derived from Class 1 outer membrane protein of the P1.7.16, subtype can be used together with outer membrane proteins or fragments of outer membrane proteins of other subtypes, such as P1.1, P1.1,16; P1.2; P1.6; P1.9; P1.15; P1.16; or P1.4 (Abdillahi, H. et al. 1988 *Micro. Pathog.* 4:27) or with meningococcal polysaccharides in mixtures or as chemical conjugates. For combined administration with epitopes of other outer membrane proteins, they can be administered separately, as a mixture or as a conjugate or genetic fusion peptide or protein. The conjugates can be formed by standard techniques for coupling proteinaceous materials or techniques for coupling saccharide polymers to proteins. Fusions can be expressed from fused gene constructs prepared by recombinant DNA techniques as described.

As mentioned, Class 1 OMP, fragment or any oligopeptides derived therefrom can be used in conjunction with antigens (e.g., polymer capsules or saccharide units, envelope or surface proteins) of other pathogenic organisms (e.g. bacteria (encapsulated or nonencapsulated), viruses, fungi and parasites). Additional examples of other organisms include respiratory syncytial virus, rotavirus, malaria parasites, and *Cryptococcus neoformans.*

In formulating the vaccine compositions with the peptide or protein, alone or in the various combinations described, the immunogen is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide), methoxyhexadecylgylcerol, and pluronic polyols; polyamines, e.g., pyran, dextransulfate, poly IC, carbopol; peptides, e.g., muramyl dipeptide and derivatives, dimethylglycine, tuftsin; oil emulsions; and mineral gels, e.g., aluminum hydroxide, aluminum phosphate, etc., lymphokines and immune stimulating complexes (ISCOMS). The immunogen may also be incorporated into liposomes, microspheres, or conjugated to polysaccharides and/or other polymers for use in a vaccine formulation.

The vaccines can be administered to a human or animal in a variety of ways. These include intradermal, intramuscular, intraperitoneal, intravenous, subcutaneous, oral and intranasal routes of administration.

Live Vaccines

The peptide and proteins of this invention can be administered as live vaccines. To this end, recombinant microorganisms are prepared that express the peptides or proteins. The vaccine recipient is inoculated with the recombinant microorganism which multiplies in the recipient, expresses the Class 1 OMP, fragment or oligopeptide thereof and evokes a immune response to *N. meningitidis*. Live vaccine vectors include: adenovirus, cytomegalovirus and preferably, pox viruses such as vaccinia (Paoletti and Panicali, U.S. Pat. No. 4,603,112) and attenuated *Salmonella* strains (Stocker, U.S. Pat. No. 4,550,081 and Curtiss et al., *Vaccine* 6:155–160 (1988)). In addition, Class 1 OMP epitopes can be incorporated into the flagella of attenuated bacterial strains.

Live vaccines are particularly advantageous because they lead to a prolonged stimulus which can confer substantially long-lasting immunity. When the immune response is protective against subsequent *N. meningitidis* infection, the live vaccine itself may be used in a preventative vaccine against *N. meningitidis*.

Multivalent live vaccines can be prepared from a single or a few recombinant microorganisms that express different epitopes of *N. meningitidis* (e.g., other outer membrane proteins from other subtypes or epitopes thereof). In addition, epitopes of other pathogenic microorganisms can be incorporated into the vaccine. For example, a vaccinia virus can be engineered to contain coding sequences for other epitopes in addition to those of *N. meningitidis*. Such a recombinant virus itself can be used as the immunogen in a mulivalent vaccine. Alternatively, a mixture of vaccinia or other viruses, each expressing a different gene encoding for different epitopes of outer membrane proteins of *N. meningitidis* and/or epitopes of other disease causing organisms can be formulated as a multivalent vaccine.

An inactivated virus vaccine may be prepared. Inactivated vaccines are "killed", i.e., infectivity has been destroyed, usually by chemical treatment (e.g., formaldehyde treatment). Ideally, the infectivity of the virus is destroyed without affecting the proteins which carry the immunogenicity of the virus. In order to prepare inactivated vaccines, large quanitites of the recombinant virus expressing the desired epitopes are grown in culture to provide the necessary quantity of relevant antigens. A mixture of inactivated viruses express different epitopes may be used for the formulation of "multivalent" vaccines. In certain instances, these "multivalent" inactivated vaccines may be preferable to live vaccine formulation because of potential difficulties arising from mutual interference of live viruses administered together. In either case, the inactivated virus or mixture of viruses may be formulated in a suitable adjuvant in order to enhance the immunological response to the antigens. Suitable adjuvants include: surface active substances, e.g., hexadecylamine, octadecyl amino acid esters, octadecylamine, lysolecithin, dimethyl-dioctadecylammonium bromide, N,N-dicoctadecyl-N', N'bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide and derivatives thereof, dimethylglycine, tuftsin; oil emulsions; and mineral gels, e.g., aluminum hydroxide, aluminum phopshate, and lymphokines.

EXEMPLIFICATION

Example 1

Monoclonal Antibodies Against Class 1 OMP's and Their Biological Activity

Type specific monoclonal antibodies were prepared against various meningococci Class 1 outer-membrane proteins. These monoclonal antibodies recognize the following subtypes: P1,1; P1,2; P1,6; P1,7; P1,9; P1,10; P1,15; P1,16; and P1,17 (now called P1,14). The monoclonal antibodies are available as "Monoclonal Kit Serotyping Meningococci" from the RIVM, Bilthoven, The Netherlands. All these monoclonal antibodies react with the SDS (sodium dodecyl sulphate) denatured protein when tested by Western blotting. It also emerged that a number of these monoclonal antibodies reacted with a 25 Kd. CNBr fragment of the 42 Kd Class 1 outer-membrane protein (see below). This result implied that the Class 1 outer-membrane protein epitopes are mainly of linear type and can therefore be copied with synthetic peptides. The epidemiological results of tests carried out by the Applicants show that the described monoclonal antibodies can subtype most of the group A, B, C meningococci which suggests a limited heterogenity. Each Class 1 outer membrane protein also appears to contain two individual type specific epitopes (Abdillahi and Poolman, Microb. Pathogen, 1988, 4': pages 27–32; idem FEMS Microbiol. Immunol. 47: pages 139–144).

The purified Class 1 outer-membrane protein (see below), subtype P1,7.16, originating from the culture of the Class 2/3 free mutant (HII15) appeared to induce a bactericidal antibody response of 1:64 serum dilution in a dose of 2.5 μg in mice. The monoclonal antibodies against meningococci Class 1 outer-membrane proteins, Class 2/3 outer-membrane proteins and lipopolysaccharides were compared as to bacteridical effect. The monoclonal antibodies against the Class 1 outer-membrane proteins appeared to possess the strongest bactericidal activity (see Table 1). The bactericidal response was determined as per Poolman, J. T. (1985), in Schoolnick, G. K. et al. Eds. 'The Pathogenic Neisseriae' ASM Publications, Washington, D.C., page 562.

TABLE 1

Bactericidal activity of a collection of monoclonal antibodies, directed against the Class 1 (cl 1), Class ⅔ (cl ⅔) and lipopolysaccharide (LPS) of meningococci. (ND - not determined).

| Test strain strain (Gp: serotype: subtype:LPS type) | Bactericidal activity of antibody pool (titre) C1 2/3 pool | C1 1 pool | LPS pool |
|---|---|---|---|
| 3006 (B:26:P1.2:L2) | 1000 | 8000 | ND |
| M981 (B:4P1.-:L5) | 10 | ND | 2000 |
| M990 (B:6:P1.6:L/) | 10 | 2000 | ND |
| M978 (B:8:P1.1:L1.8) | ND | 8000 | 1000 |
| M982 (B:9:P1.9:L3.7) | 500 | 2000 | 1000 |

TABLE 1-continued

Bactericidal activity of a collection of monoclonal antibodies, directed against the Class 1 (cl 1), Class 2/3 (cl 2/3) and lipopolysaccharide (LPS) of meningococci. (ND - not determined).

| Test strain strain (Gp: serotype: subtype:LPS type) | Bactericidal activity of antibody pool (titre) | | |
|---|---|---|---|
| | C1 2/3 pool | C1 1 pool | LPS pool |
| H355 (B:15:P1.15:L1.8) | 1000 | 8000 | 1000 |
| H44/76 (B:15:P1.7.16:L3.7) | 1000 | 8000 | 4000 |

The bactericidal activity of these monoclonal antibodies appears to correlate well with the in vivo protective activity as measured in the rat meningitis model of Saukkonen et al., 1987, *Microbial Pathogen* 3:261.

Example 1A

Construction of Meningococcal Strains Carrying Multiple Class 1 Genes

Replacement of chromosomal genes by clones, slightly different versions has been described for *Neisseria gonorrhoea*. (Stein, D. C., *Clin. Microbiol. Rev.* 2 (Suppl.), S146–S149 (1989).) We have found that this method can be applied to the Class 1 gene in *Heisseria meningitidis*. This was done in the following way:

(i) The Class 1 gene of strain 2996 (subtype P1.2) was cloned into the vector pTZ19R. (Mead, D. A. et al., *Protein Engineering* 1, 67 (1986).) The complete gene is located on a 2.2 kb XbaI fragment that was ligated to XbaI digested vector DNA.

(ii) The resulting plasmid was used for transformation of strain H44/76 (subtype P1.7,16). Cells of the acceptor strain were incubated with plasmid DNA in the presence of $Mg^{2+}$ and normal meningoccal medium; they were subsequently diluted and plated, and the resulting colonies were tested for their ability to bind P1.2-specific monoclonal antibody. Such transformants were found with a frequency of approximately $10^{-3}$. Further characterization showed that replacement of the H44/76 Class 1 gene had indeed occurred. An essential feature of the method is the presence of the donor gene on a circular plasmid DNA molecule that is not able to replicate in *N. meningitidis*, since the use of linearized DNA yielded no transformants at all.

Construction of a strain with two Class 1 genes was done by a modification of the method described above. For this purpose, the P1.2 Class 1 gene was inserted into a clones Class 5 gene. The Class 5 gene family has two features which make it particularly suitable for this construction. (Meyer, T. F. and Van Putten, J. P. M., *Clin. Microbiol. Rev.,* 2 (Suppl.) S139–S145 (1989): (i) there are four or five Class 5 genes present in the meningococcal genome, and (ii) expression of these genes is not necessary for growth under laboratory conditions. A Class 5 gene was cloned from strain H44/76 and the P1.2 gene was inserted into an SphI site located in or very close to the Class 5 gene. The resulting hybrid plasmid, pMC22, was used for transformation of strain HIII5, a Class 3-deficient mutant of H44.76. Colonies reacting with the P1.2-specific monoclonal antibody were isolated and characterized. Out of 10 such transformants, nine were found to have lost the P1.16 epitope of the acceptor strain. This indicates that in all these cases recombination has only occurred between the Class 1 genes, resulting in subtype replacement. However, one transformant was found which made both Class 1 subtypes, i.e., P1.7,16 and P1.2, suggesting that recombination between the Class 5 gene sequences on plasmid and chromosome must have occurred. This was confirmed by Western blotting, which revealed the presence of both types of Class 1 protein and by Southern blotting, which demonstrated the acquisition of a second Class 1 gene.

By continuing this construction with other Class 1 subtypes, it is possible to make a strain with four or five different Class 1 genes. The same Class 5 gene can be used in each subsequent transformation step, the different Class 5 genes can be clones and used separately. These recombinant strains can be used to prepare mixtures of different purified Class 1 OMPs.

Example 1B

Purification of Isolated OMV's from Bacteriological Culture

The purification is carried out according to Beuvery et al. (1983) loc. cit.

This culture can be done with the desired wild type strains, mutant meningococci strains without Class 2/3 outer-membrane proteins and/or homologeous and heterologeous recombinant microorganisms which express one or more of the desired meningococci Class 1 outer-membrane protein and/or epitopes by overproducing vectors either through or not through existing open reading frames and/or manipulated reading frames so that fusion proteins or proteins with exchanged epitopes can be prepared.

Readily available of wild strains are:

H44/76 (B:15:P1,7.16) (Holten E., Norway, deposited as CBS 635–89); 187 (B:4:P1,7) (Etienne J., France); M1080 (B:1:P1,1.7) (Frasch C., USA); Swiss4 (B:4:P1,15) (Hirschel B., Switzerland); B2106I (B:4:P1,2) (Berger U., West-Germany); 395 (B:NT:P1,9) (Jonsdottir K., Iceland): M990 (B:6:P1,6) (Frasch C., USA); 2996 (B:2b:P1,2) RIVM, The Netherlands; M982 (B:9:P1,9) (Frasch C., USA); S3446 (B:14:P1,6) (Frasch C., USA); H355 (B:15:P1,15) (Holten E., Norway); 6557 (B:17:P1,17) (Zollinger W., USA) and B40 (A:4:P1,10) (Achtman M., West-Germany). An example of a Class 3 negative mutant is HIII5 (B:-:P1.16) deposit # CBS 636.89.

These strains were inoculated from precultures at −70° C. into shake flasks and transferred from these into 40, 150 or 350 liter fermenter cultures. The semisynthetic medium had the following composition: L-glutamic acid 1.3 g/l, L-cysteine. HCl 0.02 g/l, $Na_2HPO_4$. $2H_2O$ 10 g/l, KCl 0.09 g/l, NaCl 6 g/l, $NH_4Cl$ 1.25 g/l, $MgSO_4.7H_2O$ 0.6 g/l, glucose 5 g/l, $Fe(NO_3)_3$ 100 μM, yeast dialysate.

During culturing in the fermenter, the pH and $PO_2$ were monitored and automatically regulated to a pH of 7.0–7.2 and an air saturation of 10%. The cells were grown to early stationary phase harvested by means of centrifuging and washing with sterile 0.1 M NaCl and stored at −20° C. or freeze-dried.

Example 2

Purification of Class 1 Outer-Membrane Proteins from Bacteriological Culture

This culture can be done with the desired wild type strains, mutant meningococci strains without Class 2/3 outer-membrane proteins and/or homologeous and heterologeous recombinant microorganisms which express one or more of the desired meningococci Class 1 outer-membrane protein and/or epitopes by overproducing vectors either through or not through existing open reading frames and/or manipulated reading frames so that fusion proteins or proteins with exchanged epitopes can be prepared.

Readily available of wild strains are:

H44/76 (B:15:P1,7.16) (Holten E., Norway, deposited as CBS 635–89); 187 (B:4:P1,7) (Etienne J., France); M1080 (B:1:P1,1.7) (Frasch C., USA); Swiss4 (B:4:P1,15) (Hirschel B., Switzerland); B2106I (B:4:P1,2) (Berger U., West-Germany); 395 (B:NT:P1,9) (Jonsdottir K., Iceland): M990 (B:6:P1,6) (Frasch C., USA); 2996 (B:2b:P1,2) RIVM, The Netherlands; M982 (B:9:P1,9) (Frasch C., USA); S3446 (B:14:P1,6) (Frasch C., USA); H355 (B:15:P1,15) (Holten E., Norway); 6557 (B:17:P1,17) (Zollinger W., USA) and B40 (A:4:P1,10) (Achtman M., West-Germany). An example of a Class 3 negative mutant is HIII5 (B:-:P1.16) deposit # CBS 636.89.

These strains were inoculated from precultures at −70° C. into shake flasks and transferred from these into 40, 150 or 350 liter fermenter cultures. The semisynthetic medium had the following composition: L-glutamic acid 1.3 g/l, L-cysteine. HCl 0.02 g/l, $Na_2HPO_4.2H_2O$ 10 g/l, KCl 0.09 g/l, NaCl 6 g/l, $NH_4Cl$ 1.25 g/l, $MgSO_4.7H_2O$ 0.6 g/l, glucose 5 g/l, $Fe(NO_3)_3$ 100 μM, yeast dialysate.

During culturing in the fermenter, the pH and $PO_2$ were monitored and automatically regulated to a pH of 7.0–7.2 and an air saturation of 10%. The cells were grown to early stationary phase harvested by means of centrifuging and washing with sterile 0.1 M NaCl and stored at −20° C. or freeze-dried.

The bacterial mass was for example extracted with the aid of 0.5 M $CaCl_2$, 1% (w/v) ZWITTERGENT 3-14 (Zw 3-14) and 0.14 M NaCl, pH 4.0, using 100 ml per gram of freeze-dried bacterial mass. The suspension was stirred for 1 hour at room temperature and then centrifuged (1 hour, 3000×g), after which the supernatant was collected in a sterile manner. 20% ethanol (v/v) was added to the supernatant and after stirring for 30 min. the product was centrifuged (30 min., 10,000×g), after which the supernatant was collected aseptically. The supernatant was then concentrated by means of diafiltration in an Amicon Hollow Fiber System (HID×50, cut off 50,000) and $CaCl_2$ and ethanol were removed. The concentrate was diluted with 0.1 M sodium acetate, 25 mM EDTA, 0.05% Zw 3-14 having a pH of 6.0 to the original volume and then concentrated again by means of diafiltration. This procedure was repeated five times. The pH of the final concentrate was adjusted to a value of 4.0.20% (v/v) ethanol was added to the concentrate and, after stirring for 30 min., the product was centrifuged (30 min., 10,000×g). The whole proteins are purified with the aid of column chromatography in the presence of detergent, for example Zw 3-14. Often gel filtration over SEPHACRYL S-300 as well as the ion exchange over DEAE SEPHAROSE is applied (Beuvery et al., (1986) supra). The used extraction method, detergents, column chromotography are not the only applicable method yet only serve as examples and must not be regarded as restrictive.

Example 3

Preparation and Characterization of Class 1 OMP Peptide Fragments

Cyanogen bromide was used to prepare fragments of meningococcal Class 1 outer-membrane proteins. The purified Class 1 or mixtures of Class 1 or 3 outer-membrane proteins were taken up in 70% (v/v) formic acid and treated with a 10-fold excess of CNBr for 16 hours at room temperature. The CNBr and the formic acid were removed by means of evaporation and replaced by 0.2 M Tris-HCl, 6 M urea solution, pH 7.2. The supernatant was prepurified by means of gel filtration over SEPHACRYL S-200 and subsequently purified with the aid of TSK-2000 gel filtration via HPLC. Beuvery et al., (1986) supra.

Enzymatic Digestion of CB2 Fragments

To further delineate the epitopes, the meningococcal CB2 fragment was subjected to digestion with EndoArg-C, EndoGlu-C or V-8 and the resulting fragments isolated by HPLC. Briefly, 20 nMoles of CB2 fragment in 1 ml of 25 mM phosphate/0.1 mM tris buffer (pH 8.0) containing 3M urea was digested at 37° C. with 0.2 nMoles of EndoArg-C (1 mg/ml in distilled water) or 0.22 nMoles of EndoGlu-C or V-8 (1 mg/ml in distilled water) for 14–18 hours. The resulting digested fragments were separated by reverse phase HPLC using a VYDAC C4 column and a trifluoroacetic acid-acetonitrile gradient. The main peak eluted from the EndoArg-C digestion had an apparent molecular weight of 7–9 Kdal while the main peak observed following EndoGlu-C or V-8 had an apparent molecular weight of 4–6 Kdals. The isolated peaks were subsequently shown by Western blot to react to a pool of monoclonal antibodies (Adam I, 62-D12-8, MN5-C11G and MN14-C 116).

The P1.16 epitope appears to be present on the C-terminal CNBr fragment of the Class 1 outer-membrane protein of strain H44/76 (B:15: P1,7.16). Further characterisation of the P1,16 epitope was carried out through amino acid sequence determination of the 17 Kd (N-terminal) and 25 Kd (C-terminal) CNBr fragments. The C-terminal 25 Kd is further fragmented with V8 protease, endoLysC, endoGlu-C and endoArg-C. Fragments which were positive with the P1,16 monoclonal antibody were sequenced as far as possible. The sequences which were obtained are as follows:

N-terminus of whole protein: DVSLYGEIKAGVEDRNYQLQLTEAQUAAGN . . . (SEQ ID NO:1)

N-terminus of 25 Kd C-terminal CNBr fragment: (M) PVSVRYDSPEFSGFSGSVQFVPIONSKSAYTPAYYTKDTNNN . . . (SEQ ID NO:2)

Fragments which react with P1,16 monoclonal antibodies were isolated using V8 protease and endoArg-C fragmentation with a molecular weight of 7–9 Kd and 4–6 Kd respectively. The N-terminal sequences hereof are as follows:

V8 7–9 Kd fragment: FSGFSGSVQFVPIQNSKSAYTPAYYTKDTN . . . (SEQ ID NO:3)

Arg-C 4–6 Kd fragment: PVSVRYDSPEFSGFSGSVQFVPIQNSKSAYTPAYYTK . . . (SEQ ID NO:4)

Example 4

DNA Sequences of Class 1 OMP Genes

Amino acid sequences of Class 1 OMP were deduced from the nucleotide sequence of the structural genes of four meningococci Class 1 OMP's with various subtypes. Comparison with four amino acid sequences enabled a prediction of the composition and the location of these epitopes. Further, the P1,7 and P1,16 epitopes were confirmed with the aid of peptide synthesis and the demonstration of binding of the respective monoclonal antibodies.

Class 1 OMP genes were cloned into lambda gt11 (as described for P1,16 in Barlow et al., (1987) *Infect. Immun.* 55: 2743–2740) and subcloned in M13 sequencing vectors and the DNA sequence was determined by standard chain termination dideoxynucleotide techniques.

The complete derived amino acid sequence for P1,16; P1,15, P1,7.16; and P1,2 proteins are as follows:

```
                       10        20        30        40        50
P1.16          DVSLYGEIKAGVEGRNIQAQLTEQPQVTNGVQGNQV--KVTKAKSRIRTKIS
(SEQ ID NO:5): **************** * ****                *************

P1.15          DVSLYGEIKAGVEGRNFQLQLTEPP-SKSQP---QV--KVTKAKSRIRTKIS
(SEQ ID NO:6): **************** * ****                *************

P1.7.16        DVSLYGEIKAGVEGRNYQLQLTEAQAANGGASGQVKVTKVTKAKSRIRTKIS
(SEQ ID NO:7): **************** * ****                *************

P1.2           DVSLYGEIKAGVEGRNIQLQLTEPLQNIQQPQ-------VTKAKSRIRTKIS
(SEQ ID NO:8): **************** * ****                *************

        60        70        80        90       100       110
DFGSFIGFKGSEDLGEGLKAVWQLEQDVSVAGGGASQWGNRESFIGLAGEFGTLRAGRVA
*************** *******************  ******* ***************

DFGSFIGFKGSEDLGEGLKAVWQLEQDVSVAGGGATQWGNRESFVGLAGEFGTLRAGRVA
*************** *******************  ******* ***************

DFGSFIGFKGSEDLGDGLKAVWQLEQDVSVAGGGATQWGNRESFIGLAGEFGTLRAGRVA
*************** *******************  ******* ***************

DFGSFIGFKGSEDLGEGLKAVWQLEQDVSVAGGGATRWGNRESFVGLAGEFGTLRAGRVA
*************** *******************  ******* ***************

       120       130       140       150       160       170
NQFDDASQAINPWDSNNDVASQLGIFKRHDDMPVSVRYDSPEFSGFSGSVQFVPAQNSKS
******* ** ****************************** ************ *****

NQFDDASQAIDPWDSNNDVASQLGIFKRHDDMPVSVRYDSPDFSGFSGSVQFVPIQNSKS
******* ** ****************************** ************ *****

NQFDDASQAIDPWDSNNDVASQLGIFKRHDDMPVSVRYDSPEFSGFSGSVQFVPIQNSKS
******* ** ****************************** ************ *****

NQFDDASKAIDPWDSNNVVASQLGIFKRMDDMPVSVRYDSPEFSGFSGSVQFVPAQNSKS
******* ** ****************************** ************ *****

       180       190       200       210       220       230
AYKPAYYTKDTNNNLTLVPAVVGKPGSDVYYAGLNYKNGGFAGNYAFKYARHANVGRNAF
** **            ************************** ************* **

AYTPAHYTRQNNTDV-FVPAVVGKPGSDVYYAGLNYKNGGFAGSYAFKYARHANVGRDAF
** **            ************************** ************* **

AYTPAYYTKNTNNNLTLVPAVVGKPGSDVYYAGLNYKNGGFAGNYAFKYARHANVGRNAF
** **            ************************** ************* **

AYTPAHFVQQTPQQPTLVPAVVGKPGSDVYYAGLNYKNGGFAGNYAFKYAKHANVGRDAF
            S+
** **            ************************** ************* **

       240       250       260       270       280       290
ELFLIGSATSDEAKGTDPLKNHQVHRLTGGYEEGGLNLALAAQLDLSENGDKAKTKNSTT
**** **  ** ************************************* *  *******

ELFLLGS-TSDEAKGTDPLKNHQVHRLTGGYEEGGLNLALAAQLDLSENGDKAKTKNSTT
**** **  ** ************************************* *  *******

ELFLIGS-GSDQAKGTDPLKNHQVHRLTGGYEEGGLNLALAAQLDLSENGD--KTKNSTT
**** **  ** ************************************* *  *******

ELFLLGS-GSDEAKGTDPLKNHQVHRLTGGYEEGGLNLALAAQLDLSENAD--KTKNSTT
**** **  ** ************************************* *  *******

       300       310       320       330       340       350
EIAATASYRFGNAVPRISYAHGFDLIERGKKGENTSYDQIIAGVDYDFSKRTSAIVSGAW
************************* **********************************

EIAATASYRFGNAVPRISYAHGFDLIERGKKGENTSYDQIIAGVDYDFSKRTSAIVSGAW
************************* **********************************

EIAATASYRFGNAVPRISYAHGFDFIERGKKGENTSYDQIIAGVDYDFSKRTSAIVSGAW
************************* **********************************

EIAATASYRFGNAVPRISYAHGFDFIERGKKGENTSYDQIIAGVDYDFSKRTSAIVSGAW
************************* **********************************
```

-continued

```
      360       370
LKRNTGIGNYTQINAASVGLRHKF
************************

LKRNTGIGNYTQINAASVGLRHKF
************************

LKRNTGIGNYTQINAASVGLRHKF
************************

LKRNTGIGNYTQINAASVGLRHKF
************************
```

+Note this amino acid 15 is located between A.A.S.184 and 185 of this sequence

Example 5

DNA Sequencing of Class 1 OMP Genes from Different *N. meningitidis* Serosubtypes The Polymerase Chain Reaction (PCR) technique of Mullis and Faloona (Methods in Enzymol. 155:335–50, 198.7) was used to amplify the entire Class 1 OMP gene and specific fragments according to the scheme shown in FIG. 1.

Primers were synthesized on an Applied Biosystems 380B DNA synthesizer and used in standard PCR 30 cycle amplification reactions using Taq polymerase in a Thermal Cycler (Perkin-Elmer Cetus, Norwalk, Conn.) according to the recommendations of the Supplier. Amplified fragments of about 1300, 900 and 450 bp were generated from each serosubtype genomic DNA preparation from the primer combinations shown in FIG. 1. The primers used had the following sequences:

```
PR1 (SEQ ID NO:9): (41 bases with universal primer extension)
TGT AAA ACG ACG GCC AGT TTG AAG ACG TAT CGG GRG TTT GC

PR2 (SEQ ID NO:10): (42 bases with universal primer extension)
TGT AAA ACG ACG GCC AGT GGC GAA TTC GGT ACG CTG CGC GCC

PR3 (SEQ ID NO:11): (42 bases with universal primer extension)
TGT AAA ACG ACG GCC AGT CAT CAG GTA CAC CGC CTG ACG GGC

PR4 (SEQ ID NO:12): (40 bases with universal primer extension)
TGT AAA ACG ACG GCC AGT GCA GAT TGG CAG TCA GAT TGC A

PR5 (SEQ ID NO:13): (40 bases with universal primer extension)
TGT AAA ACG ACG GCC AGT GGG ATC GGT ACC TTT GGC TTG A

PR6 (SEQ ID NO:14): (40 bases with universal primer extension)
TGT AAA ACG ACG GCC AGT AAC TGA TTC GCA ACG CGA CCG G

FWD (SEQ ID NO:15): (24 bases)
TTG AAG GAC GTA TCG GGT GTT TCG

REV (SEQ ID NO:16): (23 bases)
GCA GAT TGG CAG TCA GAT TGC TT
```

Excess single stranded template for sequencing was synthesized in an 'asymmetric PCR' amplification using 100× excess of primer carrying an 18 base extension at the 5' end corresponding to the universal fluorescent sequencing primers used with an Model 370A Automated DNA Sequencer (Applied Biosystems, Foster City, Calif.). Taq polymerase was used in a Standard dideoxynucleotide chain termination sequencing reaction with the PCR generated single stranded Class 1 gene fragments as templates. Derived sequences for gene segments of strains H44/76 (P1.7,16), M1080 (P1.1,7), H355 (P1.15), 6940 (P1.6)., 6557 (P1.14), 870227 (P1.10) and B40 (P1.10) are shown in FIG. 2 (see also SEQ ID NOS 61–74) and FIG. 3 see also SEQ ID NOS 75–84)

Example 6

Confirmation of Amino Acid Sequences of Class 1 OMP Subtype Epitopes

From these gene sequences confirmed by direct sequencing of Class 1 OMP genes, it was deduced that the sequences corresponding to amino acids 24–34 and 176–187 of P1.16 are markedly variable in the four Class 1 OMP sequences. Three amino acid sequences N-terminal or C-terminal from these positions should also be considered for possible inclusion in these epitopes to allow for maximizing epitope stability presentation and unexpected insertions or deletions in the native protein sequence. Further the DNA and amino acid sequences of other Class 1 OMPs should be compared with the P1.7,16 sequence to allow for maximum allignment and epitope prediction. The first variable region epitope and second variable region epitope are called VR1 and VR2 respectively. These regions encode the subtype epitopes as was confirmed with the aid of peptide synthesis and the reaction of the peptides with P1.2; P1.7; P1.15 and P1.16 specific monoclonal antibodies.

A complete set of overlapping decapeptides staggered by 5 amino acids were prepared using the P1.16 protein sequence. The anti-P1.16 monoclonal antibody reacted with the decapeptide YYTKDTNNNL (SEQ ID NO:17) from P1.16 reacted as expected and no other decapeptide. FIGS. 4*a*, 4*b*, 4*c*, 4*d*, 4*e*, 4*f*, 4*g* and 4*h*.

Of overlapping decapeptides provided with a one (1) amino acid sequence shift in the region 24–34 and 176–187 of the Class 1 OMP of strains H44/76 (P1.7,16), MC50 (P1.16) and MC51 (P1.15) more than one peptide reacted with the subtype specific monoclonal antibody. In most cases one or more of the group of these overlapping peptides reacted with the subtype specific monoclonal antibody more strongly than others FIGS. 5*a*, 5*b*, 5*c*, 5*d*, 5*e*, 5*f*, 5*g* and 5*h*.

These peptides are designated as the VR1 and VR2 epitopes. In the P1.7,16 strain, the sequence YYTKNTNNNL (SEQ ID NO:18) is present, the change D to N at residue 180 does have some effect on reducing antibody binding. The sequence HYTRQNNTDVF (SEQ ID NO:19) in P1.15 in the same relative position in the protein as the P1.16 epitope and is responsible for binding to the anti-P1.15 monoclonal antibody. AQAANGGASG (SEQ ID NO:20) shows some binding and peptides 1–3 amino acids downstream show far greater binding to the P1.7 monoclonal antibody. Sequence HFVQQTPQSQP (SEQ ID NO:21) of VR2 is responsible for binding to the anti-P1.2 monoclonal antibody. It is probable that the sequences QPQVTNGVQGN (SEQ ID NO:22) and PPSKSQP (SEQ ID NO:23) in the P1.16 and P1.15 proteins also represent epitopes.

Example 6B

Class 1 OMP Constant Region Epitope Identification

Peptides forming surface loops were prepared and conjugated to tetanus toxoid. A BIOLYNX 4170 automated peptide synthesizer (Pharmacia/LKB) was used for continuous flow solid-phase synthesis with the following exception. In the last cycle of the synthesis SAMA-OPfp (0.5 mmol) (Drijfhout, J. W. (1989), *Ph.D. Thesis*, Leiden, The Netherlands) was coupled in the presence of 1-hydroxybenzotriazole (0.5 mmol) for 30 min., using a standard protocol with omission of the piperidine-treatment (i.e. the "Fmoc-deblocking step" which in this case would cause undesirable S-deacetylation). These are referred to as SAMA-peptides.

The peptides and their surface region location which were conjugated to TT are as follows:

| Name | Peptide | Region |
|---|---|---|
| LBV 017 | 176 185<br>XGGYYTKDTNNNL | P1.16, loop 4<br>(SEQ ID NO:24) |
| 018 | 24 33<br>XGGAQAANGGASG | P1.7, loop 1<br>(SEQ ID NO:25) |
| 024 | 276 291<br>XGGLSENGDKAKTKNSTTE | P1.16, loop 6<br>(SEQ ID NO:26) |
| 025a | 245<br>XGGNAFELFLIGSATSDEAKG | P1.16, loop 5<br>(SEQ ID NO:27) |
| 025b | 223<br>XANVGRNAFELFLIGSATSDEAKG | P1.16, loop 5<br>(SEQ ID NO:28) |
| 026 | 124 137<br>XGGDSNNDVASQLQIFK | P1.16, loop 3<br>(SEQ ID NO:29) |
| 027 | XADLNTDAERVAVNTANAHPV | Class 2, loop 5<br>(SEQ ID NO:30) |
| 028a | 329<br>XGGGKKGENTSYDQ | Class 1, loop 7<br>(SEQ ID NO:31) |
| 028b | 317<br>XGGERGKKGENTSYDQ | Class 1, loop 7<br>(SEQ ID NO:32) |
| 029 | XGGVKDAGTYKAQGGKSKTATQ | Class 2, loop 1<br>(SEQ ID NO:33) |

-continued

| Name | Peptide | Region |
|---|---|---|
| 030 | 78 90<br>XGGWSVAEGGASQVGN | P1.16, loop 2<br>(SEQ ID NO:34) |
| 031 | 352 366<br>XKRNTGIGNYTQINAA | P1.16, loop 8<br>(SEQ ID NO:35) |
| 032 | 16 34<br>XGGNIQAQLTEQPQVTNGVQGN | P1.16, loop 1<br>(SEQ ID NO:36) |

Conjugation of SAMA-peptides to tetanus toxoid was performed as follows. A solution of N-succinimidyl bromoacetate (4.7 mg, 10 μmol) in DMF (100 μl) was mixed with a solution of tetanus toxoid (TT) (20 mg) in 0.1 M sodium phosphate buffer pH 7.8 (3.5 ml). After 1 h, 1.8 ml of the reaction mixture was subjected to gel filtration using a SEPHADEX PD-10 column (Pharmacia) equilibrated in 0.1 M sodium phosphate, containing 5 mM EDTA (PE buffer) pH 6.1. The bromoacetylated tetanus toxoid was eluted with the same buffer and collected in 3.5 ml. The solution of bromoactylated tetanus toxoid (1.2 ml) was added to the SAMA peptide (4.5 mg. 3 μmol) and deaerated with helium. Next, 150 μl of 0.2 M hydroxylamine (in PE buffer, pH 6.1) was added. After 16 h remaining bromoacetyl groups were blocked by addition of 2-aminoethanethiol hydrochloride (4 μmol) in buffer, pH 6.1 (150 μl). After a further period of 16 h, the peptide-TT conjugate was purified by gel filtration over a PD-10 column using PE buffer, pH 6.1, as the eluant. The appropriate fractions were combined and stored at 4° C.

To determine the immunological activity, 25 μg (total protein) per dose of a peptide-TT conjugate was injected subcutaneously at weeks 0 and 4 into 6–8 week old NIH outbred mice. (Note: Vaccine LBV 017-TT and LBV 018-TT were used at 10 μg total protein/dose.) Sera were collected 6 weeks following the first dose and evaluated for antibody response in an ELISA assay (Beuvery, E. C. et al. (1983) *Infect. and Immun.* 40:369–380). The following antigens were coated into the microtiter wells: outer membrane protein (OMP), purified Class I OMP (Poolman, J. T. et al., (1989) *Infect. and Immun.* 57:1005) and the unconjugated peptides. Bactericidal activity (BC) of sera was also measured (Poolman, J. T. et al., (1985) supra.)

The results are presented in Table 2 below.

TABLE 2

| Vaccine | OMC | Class 1 OMP | Synth.Peptide | Bactericidal Test |
|---|---|---|---|---|
| LBV 018-TT | 1:900 (0.05)* | 1: 2700 | ND | <1:64 |
| LBV 017-TT | 1:900 (1) | 1:900 | ND | <1:64 |
| LBV 024-TT | 1:100 | 1:100 | 1:900 (homol.) | <1:64 |
| LBV 025a-TT | — | 1:100 | 1:2700 (homol.) | <1:64 |
| LBV 025b-TT | 1:2700 (4) | 1:300 | 1:8100 (homol.) | <1:64 |
| LBV 026-TT | — | — | — (homol.) | <1:64 |
| LBV 027-TT | — | 1:300 | 1:300 (homol.) | <1:64 |
| LBV 028a-TT | 1:100 | — | 1:2700 (homol.) | <1:64 |
| LBV 028b-TT | 1:100 | 1:100 | 1:900 (homol.) | <1:64 |
| LBV 029-TT | — | 1:100 | 1:8100 (homol.) | <1:64 |
| LBV 030-TT | — | 1:100 | 1:2700 (homol.) | <1:64 |
| LBV 031-TT | — | 1:100 | — (homol.) | <1:64 |
| LBV 032-TT | — | 1:100 | 1:900 (homol.) | <1:64 |

*numbers in ( ) indicate O.D. level showing this titer

These data suggest that of the constant surface loops tested of Class 1 and 2 OMPs of *N. meningitidis* loop 5 appears to represent at least one region that will produce antibodies which will cross-react with Class 1 and Class 2 OMP of many strains of *N. meningitidis*.

Example 7

Construction of Recombinant Flagellins Expressing Meningococcal Epitopes

To create hybrid flagella containing epitopes from Class 1 meningococcal epitopes, a series of oligonucleotides was designed based on primary protein sequence data and epitope mapping data. Two oligonucleotides based on VR1 or VR2 epitopes of outer membrane P1.7.16 were designed so that they could be cloned in single or multiple copies into a cloning region within the gene for *S. muenchen* flagellin. Translation termination signals were included on the non-coding strand of the oligonucleotide to facilitate screening by expression of the cloned inserts.

The plasmid vector pPX1650 containing the entire coding region and promoter regions for the structural gene for flagellin H1-d of *Salmonella meunchen* (deposited at the ATCC, accession #67685) was modified to contain several unique cloning sites suitable for the insertion of either oligonucleotides or gene fragments in each of the three reading frames of the flagellin gene FIG. 6; see also SEQ ID NOS 182–188. First, pPX1650 was digested with EcoRV, which cleaves pPX1650 twice, 48 base pairs apart, and religated to yield a plasmid, pPX1651, which has a unique EcoRV cloning site and which results in a 16 amino acid deletion in the flagellin protein. pPX1651 was identified by screening *E. coli* recombinants on Western blots probed with polyclonal antibody directed against H1-d flagellin. pPX1651 was identified amongst several candidates having flagellins smaller than wild type flagellin (of 1650) and was verified by sequencing. Second, pPX1651 was restricted with BamH1 and religated after filling out the overhanging ends with Klenow enzyme to remove the unique BamH1 restriction enzyme site in the polylinker region of the vector. As a final step, the resulting vector was digested with EcoRV and the following double-stranded oligonucleotide linker was inserted:

```
5'   ATG ATC GAT GGA TTC    3' (SEQ ID NO:37)
```

Candidates were screened for the newly created BamH sites and several candidates having BamH1 sites were screened for orientation of the linker by double strand DNA sequencing methodology. One candidate having the linker in the above orientation was retained as pPX1647:

```
5' . . . . GAT ATC ATC GAT GGA TTC ATC . . . . (SEQ ID NO:38)
           EcoRV     Cla1   BamH1
```

Plasmid pPX1647 (FIG. 7) was digested with BamH and either oligonucleotides for VR1 or VR2 were cloned into *E. coli* cells. Screening for desired recombinants was accomplished by digesting plasmid minilysate DNA with appropriate diagnostic restriction enzymes and screening for expression by probing hybrid flagella for decreased mobility on SDS-PAGE gels with specific flagellar antiserum (H1-d). A number of the resultant clones showed decreased mobility on SDS-PAGE, indicating proper insertion of one or more of the oligonucleotides for VR1 or VR2. Several of each were retained for analysis by DNA sequencing. Clone CB1-2 results from tandem insertion of two copies of the VR1 oligonucleotide and clone CB1-4 results from insertion of four oligonucleotides. Likewise CB2 P contained a single insert of the VR2 oligonucleotide and CB2 W showed the expected trimeric insert, CB2 P clone contained a single base pair change which resulted in a change from Leu to Phe in the expressed VR2 fusion protein and was not retained for further study. The recombinant flagellin clones in *E. coli* were probed with monoclonal antibodies (Abdillahi and Poolman, Microbiol. Pathogenesis 4:27–32, 1988; RIVM, The Netherlands) known to react with either VR1 or VR2 epitopes. Monoclonals Adam-1 (P1.7) and Mn14-C11-G (P1.7) react with hybrid flagellin containing 2 or 4 tandem inserts of VR1, but do not react with clones containing VR2. The weaker reaction of both monoclonals with CB1-2 than with CB1-4 is likely due to epitope density. By the same token, monoclonals 62 (P1,16) and Mn5-c11-G (P1.16) react with CB2 W clone, but not with the VR1 inserts. The CB2 P clone fails to react with either VR2 antibody, probably due to the Leu to Phe change.

Each of these clones was transformed into an aroA *S. dublin* strain (SL5927), having a Tn10 insertion in the H1-d locus, to examine the functioning of the hybrid flagella. Each of the four clones resulted in motile bacteria; motility of the transformants was inhibited by the corresponding monoclonal antibody, including clone CB2 P, indicating affinity of the VR2 monoclonal for the epitope in intact flagella. This result indicates that epitopes are exposed at the cells surface and are accessible to antibody.

Hybrid flagellin containing both VR1 and VR2 epitopes were created by cleaving either CB1-2, CB1-4, or CB2 W with BamH1 and cloning the heterologous epitope. Clones CB12-7 and CB12-10 result from the in-frame insertion of a single copy of the VR2 oligonucleotide behind either 2 or 4 VR1 tandem inserts, respectively; clone CB21-F arose from the insertion of one copy of the VR1 epitope behind 3 tandem copies of VR2. CB12-7 and CB12-10 are recognized only by VR1 monoclonal antibody and CB21-F is recognized only by VR2 monoclonal. These results, taken together with DNA analysis revealing predicted sequences, indicate epitope density is too low in the combined hybrids. To create a hybrid flagellin with increased density of both VR1 and VR2 epitopes, CB12-10 was digested with BamH1 and VR2 encoding oligonucleotides were inserted. Clone 12-10-6 contains two further tandem inserts of the VR2 epitope, resulting in a hybrid flagellin molecule in which four tandem copies of VR1 are followed by three copies of VR2. As is shown in FIGS. 3*a* and *b*, three of the hybrid flagellin vaccine candidates have the expected molecular properties. The flagellin (pCB1×4) containing 4 copies of VR1 reacts with anti-H1-d (anti-flagellin) and anti-VR1 monoclonal antibodies, but not with anti-VR2 monoclonal antibodies; the flagellin (pCB2-W) containing 3 tandem copies of VR2 reacts with anti-H1-d and anti-VR2 antibodies, but not with anti-VR1; the combined hybrid containing copies of VR1 and 3 copies of VR2 reacts with both anti-VR1 and anti-VR2 monoclonal antibodies. The combined hybrid specified motility when introduced into a non-motile recipient *S. dublin* strain.

As a subunit vaccine, the goal is to obtain suitable initial vaccine candidates in high quantity and high purity. A suitable vaccine candidate can be chosen from the above type constructions based on reactivity to monoclonal antibodies and function of flagella in non-motile *Salmonella* host strains. A subunit flagellin vaccine may not need to retain all functional aspects of a parental flagellin, but should at least retain surface localization for purification purposes. Several subunit flagellin meningococcal vaccine were chosen from the above described hybrid molecules based on reactivity to monoclonal antibodies and implied surface localization based on restoration of bacterial motility. Three flagellin vaccine candidates contained either 4 tandem inserts of VR1, 3 tandem inserts of VR2, or 4 μl inserts followed by 3 VR2 inserts. Because flagellin is a major protein of *Salmonella*, it is possible to easily purify sufficient material for vaccination studies using techniques established for flagella purification (Logan et al., J. Bacteriol. 169: 5072–5077, 1987).

Example 8

Initial Purification of Recombinant Flagellin Molecules

The three hybrid flagellin vaccine candidates and a wild type (derived from pPX1650) were inoculated into four-liter baffled Fernbach flasks containing 1 liter of LB broth. Bacterial cultures were incubated at 37° C. with shaking (200 rpm) for 22–24 hr. Under these conditions of culturing, the bulk of the flagella were sloughed from the bacterial cell surface and were localized in the supernatant culture medium. To obtain suitable material, flagella were isolated from 6–8 liters of culture medium. To obtain purified flagellin preparations for vaccination studies, flagellar filaments were harvested from bacterial culture supernatants by the following procedure: Ammonium sulfate was added to culture supernatant so that final solution was 50% saturated; the solution was stirred gently at 4° C. for several hours and the precipitated material was collected by centrifugation in a GSA rotor at 5000 rpm for 30 minutes. The collected ammonium-sulfate precipitated material was reconstituted in PBS and dialyzed against PBS at 4° C. for 12–15 hrs. The dialyzed material was subjected to high speed centrifugation at 100,000×g for 1 hour in an SW-27 rotor to pellet the flagellar filaments. The pelleted material, which consisted primarily of flagellin, was subjected to further purification by the following method.

Example 9

HPLC Purification of Recombinant Flagellins

Figure 9:
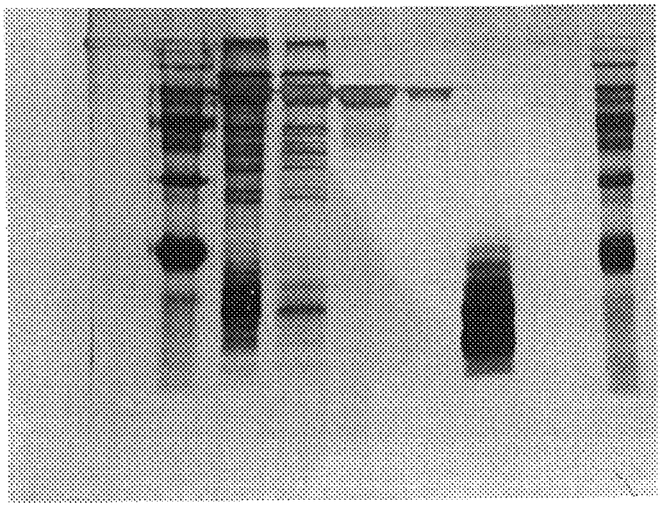
FIG. 9. Representative analysis by SDS-PAGE of recombinant flagellin.

To prepare highly purified flagellins, *Salmonella* expressing the constructions, in particular pCB12-10-6, was grown as described above and the cells pelleted at 10,000 G. The culture supernatant was then precipitated with 50% ammonium sulfate, centrifuged at 10,000 G and resuspended in 30 ml PBS. The resuspended pellet was dialyzed against 10 mM Tris buffer (pH=8.0) containing 6M urea, 1 mM PMSF, 2 mM NEM, and 5 mM EDTA overnight at 4° C. Dialyzed material was then passed over two DEAE SEPHAROSE minicolumns (3.0 ml volume, 4.0 ml eluent over each). The columns were eluted (5×) with 50 mM NaCl in 10 mM tris (pH=8.0) containing 6M urea and then with 1M NaCl in 10 mM tris (pH=8.0) containing 6M urea. The first four elution collections (20 ml) of the 50 mM NaCl were pooled and dialyzed against 1.0 liter 10 mM acetate buffer (pH=4.0) in 6M urea at room temperature. The dialyzed fractions were then loaded onto a TSK SP PW cation exchange HPLC column (75 mm×300 mm). The column was eluted with a mobile phase consisting of 10 mM acetate (pH=4.0) containing 6M urea. A gradient 0–300 mM NaCl was established in 10 mM acetate (pH=4.0) containing 6M urea over the 5–30 min interval. After 30 mins the gradient went from 300 mM to 1 M NaCl in 10 mM acetate in 6M urea over the next 5 min. The flagellin construct was collected at approximately 24 min. which corresponds to about 200 mM NaCl. The fraction was dialyzed against PBS and purity determined on the material was established by Western blots using anti-flagellin antibody. A representative HPLC analysis and SDS-PAGE are shown in FIGS. 8 and 9 respectively.

Example 10

Preparation of Meningococcal-Flagellin Glycoconjugate

Group C meningoccal capsular polysaccharide (GCM CPS: lot # 86 NM 01) was prepared essentially according to Bundle et al. Bundel et al., *J. Biol. Chem.* 249: 4797–801, 1974).

*Neisseria meningitidis* strain C11 was obtained from the Walter Reed Army Institute (Washington, D.C.). The strain was precultured twice on sheep blood agar plates, then used for the inoculation of a liquid seed culture medium *Neisseria* chemically defined medium, NCDM (Kenney et al., Bull. W.H.O. 37 469–73, 1967). Finally, 40 l of liquid medium (NCDM) in a fermentor was inoculated with the liquid preculture. The purity of the strain was checked at each stage. After centrifugation, the supernatant was precipitated by addition of CETAVLON to a final concentration of 0.1%, and the insoluble complex re-dissolved in cold 1 M calcium chloride ($CaCl_2$) (Gotschlich et al., *J. Exp. Med.* 129: 1349–65, 1969). Ethanol (96%) was added to a final concentration of 25% (v/v). After 1 h, the suspension was centrifuged (1 h, 50,000 g), the supernatant was collected, and its ethanol concentration was increased to 80% (v/v). After 1 h, centrifugation (20 min, 5,000 g) yielded a precipitate which was washed successively with absolute ethanol, acetone and diethylether, and then dried in a vacuum dessicator over phosphorus pentoxide ($P_2O_5$) to constant weight. This crude CPS was stored at −20° C.

In order to obtain a purer preparation, the CPS was then dissolved in sodium acetate buffer (1.10 dilution of a saturated solution, pH 7.0) and extracted four times wiht hot phenol (Westphal et al., *Z. Naturforsch.* 7b:148–55, 1952). After dialysis of the combined aqueous phases against 0.1 M $CaC_2$, followed by centrifugation (3–5 h, 100,000 g), a final ethanol precipitation was performed on the clear supernatant, and the resulting precipitate washed with organic solvents and dried, as described above. The pure CPS was then stored at −20° C.

At each stage of the purification process, the CPS was analyzed for carbohydrate N-acetylneuraminic acid, NANA) (Svennerhold, *Biochim. Biophys. Acta* 24:604, 957), O-acetyl (Hestrin, *J. Biol. Chem.* 180:249, 1949), and protein (260 nm detection) content, and its molecular weight checked by gel filtration.

Group C meningococcal capsular polysaccharide (GCM CPS) was simultaneously depolymerized and activated via sodium periodate ($NaIO_4$) oxidation in aqueous buffer (Anderson et al., *J. Immunol.* 137:1181–6, 1986; Eby et al., *Pediat. Res.* 20:308A, 1986, Anderson et al., *J. Pediatr.* 111(5):644–50, 1987; Anderson, U.S. Pat. No. 4,762,713; 1988). The reaction was monitored by high performance gel permeation chromatography (HPGPC) in aqueous eluent, using ultraviolet (UV) and refractive index (RI) detection. The reaction was stopped and the activated oligosaccharides (GCM OS) were desalted by low pressure gel permeation (GPC) in water, and then lyophilized. A solution was then prepared in water and subsequently frozen for temporary storage. GCM OS and flagellin pCB12-10-6 were mixed in aqueous neutral buffer and the conjugation was initiated by addition of sodium cyanoborohydride ($NaBH_3CN$) (Anderson, U.S. Pat. No. 4,762,713, 1988; U.S. Pat. No. 4,673,574, 1987; U.S. Pat. No. 4,761,283, 1988). The reaction was carried out for 5 days, while being monitored by HPGPC. It was finally stopped by dialysis/concentration on centrifugal microconcentrators. The final preparation was stored in the cold, in the presence of thimerosal to prevent bacterial growth. The resulting glycoconjugate not only provides a mechanism to present the expressed VR1 and VR2 meningococcal epitopes to the immune system but also serves a's a carrier molecule for the presentation of a meningococcal oligosaccharide.

In preparation of the conjugate, the following conditions were employed. Purified flagellin pCB12-10-6 was dissolved in 15% sucrose (3.5 mg/ml) and then stored at −20° C. GCM CPS (9.7 mg; final concentration: 5 mg/ml) was oxidized by 100 mM $NaIO_4$ in 0.05 M sodium phosphate buffer (pH 6.2–6.5) at RT, in the dark, with agitation. Aliquots (100 μl) were withdrawn at regular intervals, the reaction stopped by addition of ethylene glycol (10 μl), and analysis was performed by HPGPC on Waters (Milford, Mass.) Ultrahydrogel™ 250+120 (2 columns coupled; 2×300 mm×7.8 mm) in 0.2 M phosphate-saline buffer (PBS; 0.2 M sodium phosphate, 0.9% NaCl, pH 7.8), at a flow rate of 0.8 ml/min, using UV (206 nm) and RI detection. After 2 h 30 min, the reaction was stopped by addition of ethylene glycol (1/10 of the reaction volume), and the GCM OS were desalted by GPC on Bio-Rad (Richmond, Calif.) Bio-Gel® P-2 (200–400 mesh, 30 cm×1.5 cm) in water, at about 18 ml/h. Fractions were collected (1.2 ml) and analyzed for the presence of NANA the carbohydrate N-acetylneuraminic acid (NANA) (Barry et al., *J. Gen. Microbiol.* 29:335–52, 1962) and aldehydes (Porro et al., *Anal. Biochem* 118: 301–306, 1981). Positive fractions were pooled and lyophilized. Desalted GCM OS (4.7 mg) were then dissolved in water (10 mg/ml) and frozen at −20° C.

Both GCM OS and pCB12-10-6 solutions were analyzed by HPGPC (UV at 206 and 280 nm respectively) before being frozen, and prior to the conjugation. No degradation occurred during storage, as ascertained by the exact similarity of the elution profiles.

GCM OS (2 mg; final concentration: 2.6 mg/ml) and flagellin pCB12-10-6 (2.3 mg; final concentration: 3 mg/ml) were mixed in a polypropylene tube in 0.4 M sodium phosphate buffer (pH 7.0), and $NaBH_3CN$ was added (12 μmoles) to initiate the conjugation (Anderson, U.S. Pat. No. 4,762,713, 1988; U.S. Pat. No. 4,673,574; U.S. Pat. No. 4,761,283). The reaction mixture was left one day at RT, then 4 days at 35° C., without agitation. The reaction was monitored by HPGPC (UV at 280 nm) at different stages, and finally stopped by dialysis/concentration on microconcentrators. The final preparation was analyzed for NANA (Barry et al., *J. Gen. Microbiol.* 29:335–353, 1962) (0.09 mg at 0.12 mg/ml) and protein (Lowry et al., *J. Biol. Chem.* 193:265–275, 1951) (1.12 mg; 1.45 mg/ml) content. It was then stored at 4° C. in the presence of thimerosal (0.01%, w/v) to prevent bacterial growth.

The conjugate preparation was also checked by SDS-PAGE (silver nitrate stain) and Western blots analyzes. Several high molecular weight bands appeared on the gel above the pure pCB12-10-6 band and near the stacking well, the latter being an evidence that cross-linking occurred during conjugation. Western blot analyzes showed that each band was reactive with the antisera used (anti-GCM, -VR1, and -VR2), proving covalency of the conjugate bonds.

Example 11

Conjugation of Meningococcal Peptides to CRM and Bovine Serum Albumin

Peptides designated as M20 and M21 were produced on an ABI model-peptide synthesizer by solid phase synthesis using the tBoc chemistry were coupled to $CRM_{197}$ (prepared as described by Andersen, U.S. Pat. No. 4,762,713) using a bifunctional crosslinking agent, sulfosuccinimidyl (4-iodoacetyl) amino benzoate (Sulfo SIAB; purchased from Pierce) following the modification of a published procedure (Weltman, J. K. et al., (1983) Bio Techniques 1, 148–152). Briefly $CRM_{197}$ was activated by sulfo SIAB resulting in the formation of an amide bond between SIAB and amino groups of $CRM_{197}$. After the removal of unreacted crosslinker from the activated $CRM_{197}$ by gel filtration, peptide (M20 or M21) containing linking spacer (represented in underlined letters) with carboxy terminal cysteine residue was mixed with activated CRM and incubated at room temperature for 2–4 hours. Following the reaction, the conjugated material was dialyzed extensively against PBS at 4 C.

The sequence of M20 peptide (VR2 epitope) is as follows:

H-Tyr-Tyr-Thr-Lys-Asp-Thr-Asn-Asn-Asn-Leu-Thr-Leu-Val-Pro-Ala-Gly-Ala-Cys-OH (SEQ ID NO:39)

The sequence of M21(VR1 epitope) peptide is:

H-Ala-Gln-Ala-Ala-Asn-Gly-Gly-Ala-Ser-Gly-Gln-Val-Lys-Ala-Gly-Ala-Cys-OH (SEQ ID NO:40).

Figure 10:
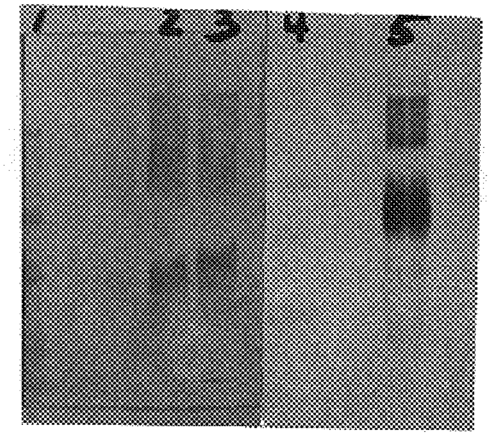
FIG. 10. Regresentative Western blot analyses of a conjugate comprising an epitope of *N. Meningitidis* Class 1 OMP conjugated to $CRM_{197}$.

Conjugated materials were subjected to SDS PAGE, transferred to PVDF membranes (IMMOBILON, Millipore) and reacted with specific monoclonals which recognize VR1 and VR2 epitopes. FIGS. 10*a* and 10*b* show the western blot analysis of M20 and M21 $CRM_{197}$ conjugates, against a pool of VR1 and VR2 specific monoclonals (Adam I, G2-D12-8 (P1.7), MN5-C11-G (P1.16) and MN14-C11-6 (P1.7)).

In order to assay the antibody response to M20 and M21<peptide by enzyme linked immunoassay procedure, BSA conjugates were prepared by using a different bifunctional crosslinking agent, N-Succinimidyl Bromoacetate as described by Bernatowicz and Matsueda (Anal. Biochem. 155, 95–102 (1986)). Covalent coupling of peptide to the protein was confirmed by western blotting of electrophoresed samples as described for $CRM_{197}$ conjugates.

Example 12

Retention of T Cell Activity by M20 and M21-$CRM_{197}$ Conjugates

To determine whether conjugation of the VR1 and VR2 epitopes to CRM adversely affect the T cell recognition of the $CRM_{197}$ protein a T cell proliferative assay was performed as previously described by Bixler and Atassi (Immu nol. Commun. 12:593, 1983). Briefly, SJL/j mice were immunized with 50 μg of native CRM197 emulsified in CFA. Seven days later, lymph nodes were removed, cultured in RPMI and challenged with various concentrations of proteins (0.05–100.0 μg/ml) and peptides. After 3 days incubation, cultures were pulsed with [$^3$H]-thymidine for 16 hours and then harvested for counting.

TABLE 3

T cell responses to meningococcal peptide-CRM197 conjugates.

| In Vitro Challenge | Maximum observed ($^3$—H) Incorporation μg/ml | ΔCPM | SI |
|---|---|---|---|
| Diphtheria toxoid | 5 | 27,510 | 57 |
| CRM197 | 50 | 108,631 | 221 |
| CRM197 - mock conjugate | 100 | 116,326 | 236 |
| M21-CRM197 | 100 | 182,499 | 370 |
| M20-CRM197 | 10 | 89,972 | 183 |
| CON A | 1 | 34,316 | 70 |
| LPS | 50 | 61,579 | 126 |
| Tetanus toxoid | 10 | 515 | 2 |
| Background (cpm) | — | 494 | 1 |

As shown in Table 3, a comparison of $CRM_{197}$ with the $CRM_{197}$-mock conjugate shows that the conjugation procedure by itself did not alter the T cell recognition of the protein. The T cell responses induced by the M20 and M21-$CRM_{197}$ conjugates were essential equivalent to or greater than the response elicited by CRM itself indicating that the recognition of the T cell epitopes on the $CRM_{197}$ is not adversely affected by the peptide conjugation. The responses to the control materials Con A, LPS and Tetanus toxoid were as expected.

Example 13

Immunogenicity of Conjugate and Recombinant Meningococcal B Vaccines

Recombinant flagellin expressing the meningococcal VR1 and/or VR2 epitopes were prepared and purified as described in Examples 7, 8 and 9. In addition, synthetic peptides representing the meningococcal epitopes VR1 and VR2 were synthesized, covalently coupled to the carrier molecule $CRM_{197}$ and purified as in Example 12. Vaccines were formulated with each of these materials at protein concentrations of 10 or 100 μg/ml for each of the components. The vaccine compositions also included aluminum phosphate at 1 mg/ml or except as noted were compounded with Freund's complete adjuvant or without supplemental material.

To evaluate immunogenicity, outbred Swiss Webster mice were immunized intramuscularly at weeks 0 and 2 with 1 or 10 μg protein/dose. Sera were collected at two week intervals, pooled for assay, and screened for antibody activity by ELISA to outer membrane complex (OMC), purified OMP (P1.16), VR1 peptide coupled to Bovine serum albumin (M21-BSA), VR2 peptide coupled to BSA (M20-BSA), wildtype flagellin, and to $CRM_{197}$. The results of the ELISA performed on sera obtained at 6 weeks are shown in Table 4.

TABLE 4

Immunogenicity of recombinant or CRM197 conjugate vaccines containing the meningococcal p1.16 OMP epitopes VR1 and VR2.

| DOSE μg | ELISA TITERS 4 WEEKS AFTER SECONDARY BOOST[1] OMC | P1.16 | M21-BSA | M20-BSA | FLAGELLIN | CRM |
|---|---|---|---|---|---|---|
| pP x 1650 (control wildtype flagellin)[2] | | | | | | |
| 1 | <150 | <100 | 171 | 100 | 427,781 | ND |
| 10 | <150 | 100 | 154 | <100 | 468,385 | ND |
| pCB1-4 | | | | | | |
| 1 | 532 | 4,376 | 4,525 | ND | 787,120 | ND |
| 10 | 2,034 | 12,387 | 17,565 | ND | 887,861 | ND |
| pCB2-W | | | | | | |
| 1 | 150 | 308 | ND | 501 | 263,143 | ND |
| 10 | 1,350 | 12,190 | ND | 5,476 | 1,493,216 | ND |
| pCB12-10-6 | | | | | | |
| 1 | 615 | 3,374 | 4,651 | 824 | 299,889 | ND |
| 10 | 1,423 | 3,666 | 3,882 | 2,253 | 497,622 | ND |
| pCB12-10-6 without aluminum phosphate | | | | | | |
| 1 | 409 | 739 | 505 | 597 | 139,147 | ND |
| 10 | 450 | 1,533 | 817 | 1,611 | 358,033 | ND |
| M20-CRM197 | | | | | | |
| 1 | <150 | <100 | 217 | <100 | ND | 42.27 |
| 10 | 50 | <100 | 150 | <100 | ND | 95.31 |
| M21-CRM197 | | | | | | |
| 1 | 68 | 249 | 10,494 | 100 | ND | 17.41 |
| 10 | 110 | 311 | 26,807 | 191 | ND | 20.92 |

TABLE 4-continued

Immunogenicity of recombinant or CRM197 conjugate vaccines containing the meningococcal p1.16 OMP epitopes VR1 and VR2.

| DOSE | ELISA TITERS 4 WEEKS AFTER SECONDARY BOOST[1] | | | | | |
|---|---|---|---|---|---|---|
| μg | OMC | P1.16 | M21-BSA | M20-BSA | FLAGELLIN | CRM |
| MIXTURE OF M20 AND M21 CONJUGATES | | | | | | |
| 1 | 50 | 100 | 40,000 | 187 | ND | 37.32 |
| 10 | 50 | 227 | 15,539 | 132 | ND | 184.27 |
| OMP P1.16 | | | | | | |
| 1 | 12,630 | 17,714 | 100 | 764 | ND | ND |
| 10 | 23,178 | 67,565 | 162 | 3,276 | ND | ND |
| pCB1-4 in CFA | | | | | | |
| 10 | 1,665 | 10,606 | 19,945 | ND | 1,841,852 | ND |
| pCB2-W in CFA | | | | | | |
| 10 | 1,157 | 6,869 | ND | 17,749 | 1,217,063 | ND |

[1]All pre-bleed values at or below the lower limit of assay of 1/100 dilution.
[2]All vaccines were formulated with 1 mg/ml aluminum phosphate except as noted.

Alternatively, the various vaccines were evaluated for immunogenicity in 6–8 week old NIH outbred mice. The mice were immunized with 100 μg (total protein)/dose subcutaneously on week 0 and 4 with vaccine and sera was collected on week 6. The sera were evaluated in an ELISA assay and using antigens as described in Example 6. Bactericidal activity was measured as in Example 6. The results are found in Table 5.

TABLE 5

| Vaccine | ELISA (titer > 0.5 OD) OMC | Class 1 OMP | Synth. Peptide | Bactericidal Test |
|---|---|---|---|---|
| FLAGELLIN | | | | |
| p1650 | — | — | — | <1:64 |
| pCB12.10.6 | — | 1:900 | — | <1:64 |
| pCB2-W | — | 1:300 | 1:100 | <1:64 |
| pCB1-4 | 1:300 (.25) | 1:2700 | — | <1:64 |
| CRM197 | — | — | — | <1:64 |
| M20-CRM197 | 1:00 | 1:8100 | — | <1:64 |
| M21-CRM197 | 1:300 (.125) | 1:8100 | — | <1:64 |

The recombinant flagellins containing either a VR1, VR2 or a cassette of both VR1 and VR2 were effective in eliciting an antibody response which was cross-reactive to the purified P1.16 and to a lesser extent to OMC. Sera from animals immunized with 10 μg of either pCB1-4 or pCB2-w induced antibodies which bound to their respective peptide-BSA conjugates as well as cross reacted with the P1.16 and OMC. Similar results were obtained with the constructed pCB12-10-6 which contains both meningococcal epitopes. In addition, each construction induced significant anti-flagellin titers as well. In contrast, the control wildtype flagellin only induced an antibody response to flagellin itself. Sera collected prior to immunization showed no pre-existing response to the materials being evaluated.

The data also demonstrates the benefits of formulating the recombinant flagellins with alum or other adjuvants such as CFA. The construction pCB12-10-6 was formulated with and without the addition of aluminum phosphate. As shown in table 2, pCB12-10-6 alone was capable of inducing an antibody response which react to the peptide conjugates as well as to the purified P1.16 as well as to OMC. In comparison, the same construction when formulated with alum was able to elicit greater antibody response at an equivalent dose. Similarly, the recombinant flagellins pCB1-4 and pCB2-w were also formulated with CFA. Again, equivalent or higher antibody titers were observed in the presence of CFA.

The results of the immunogenicity studies with the meningococcal VR1 and VR2 conjugates are also shown in Table 4. Both the M20 and the M21-$CRM_{197}$ conjugates as well as a mixture containing equal amounts of both conjugates were capable of inducing an anti-$CRM_{197}$ response as well as an anti-Class 1 OMP response.

These preliminary data indicate a Class 1 OMP variable region epitopes either chemically conjugated to a carrier or genetically fused to a carrier elicit an immune response. New epitope-carrier conjugates can be made using standard techniques to enhance the immune response to the vaccine, for example, use of 1) larger epitopes, 2) peptides with multiple epitope repeats and/or 3) different carriers.

Example 14

Preparation of Meningoccal-Human Serum Albumin Glycoconjugate

GCM CPS was depolymerized by acid hydrolysis and GCM OS obtained were subsequently activated via $NaIO_4$ oxidation in aqueous buffer. The reactions were monitored by HPGPC in aqueous eluent, using UV and RI detection. The reactions were each followed by GPC desalting in water. GCM OS and human albumin (HA) were mixed and conjugated essentially as described in Example 10 for the miningococcal-flagellin glycoconjugate. The final preparation was stored in the cold, in the presence of thimerosal to prevent bacterial growth.

In preparation of the conjugate, the following experimental conditions were employed. Human albumin (HA; Sigma®, St. Louis, Mo.) was dissolved in 15% sucrose (10 mg/ml) and then stored at −20° C. GCM CPS (lot # 86 NM 01; 106 mg; final concentration: 10 mg/ml was hydrolyzed in 0.1 N HCl at 50° C. with agitation. Aliquots (25 μl) were withdrawn at regular intervals, the reaction stopped by addition of sodium hydroxide (NaOH) and analysis was performed by HPGPC as described. After 3 h 40 min., the reaction was stopped by addition of NaOH, and the GCM OS were desalted by GPC. Fractions were collected (1.2 ml) and analyzed as described before. Positive fractions were pooled and lyophilized. Desalted GCM OS (89 mg) were then stored at −20° C. Activated OS were prepared by oxidation of GCM OS (11.8 mg; final concentration: 5 mg/ml) with 2 mM $NaIO_4$ in 0.05 M sodium phosphate buffer (pH 6.2–6.5) at RT, in the dark, with agitation. The reaction was stopped after 30 min by addition of ethylene glycol. HPGPC analyzes showed no degradation of the molecular weight of the OS during activation. Desalting and calorimetric anaylzes were then performed as described above. The resulting activated GCM OS (8.8 mg) were dissolved in water (10 mg/ml) and frozen at −20° C.

Both GCM OS and HA solutions were analyzed by HPGPC (UV at 206 and 280 nm respectively) before being frozen, and prior to the conjugation. No degradation occurred during storage, as ascertained by the exact similarity of the elution profiles.

GCM OS (6 mg; final concentration: 2.5 mg/ml) and HA (12 mg; final concentration: 5 mg/ml) were mixed in a polypropylene tube in 0.4 M sodium phosphate buffer (pH 7.0), and $NaBH_3CN$ was added (60 μmoles) to initiate the conjugation (Anderson, U.S. Pat. No. 4,762,713, 1988; U.S. Pat. No. 4,673,574, 1987; U.S. Pat. No. 4,761,283, 1988). The reaction mixture was left one day at RT, then 4 days 15 35° C., without agitation. The reaction was monitored by HPGPC (UV at 280 nm) at different stages, and finally stopped by dialysis/concentration on microconcentrators. The final preparation was analyzed for NANA (Barry et al., *J. Gen. Microbiol.* 29P335–51, 1962) (2.07 mg at 0.86 mg/ml) and protein (Lowry et al., *J. Biol. Chem.* 193265–75, 1951) (9.51 mg at 3.96 mg/ml) content. It was then stored at 4° C. in the presence of thimerosal (0.01%, w/v) to prevent bacterial growth.

The conjugate preparation was also checked by SDS-PAGE (silver nitrate stain) and Western blot analyzes. A diffuse band appeared on the gel which covered a significantly wider molecular weight range than the pure HA. Western blot analyzes showed that this band was reactive with the antiserum used (anti-GCM), proving covalency of the conjugate bonds.

Example 15

Immunogenicity of Meningococcal Oligosaccharide-Recombinant Flagellin Vaccines

A meningococcal oligosaccharide-recombinant flagellin vaccine was prepared as described above and formulated at 100 μg protein/ml. Vaccine compositions were also prepared which contained aluminum phosphate (1 mg/ml) or complete Freund's adjuvant in addition to the glycoconjugate.

To evaluate the immunogenicity, outbred Swiss Webster mice were immunized intramuscularly with 10 μg protein at week 0 and 2. Sera were collected at weeks 0, 2 and then weekly intervals thereafter to 6 weeks. After collection, pooled sera samples were assayed for antibody activity by ELISA to meningococcal C oligosaccharide conjugate to human serum albumin, OMC, P1.16, CB1 and CB2-BSA conjugates and flagellin.

The MenC-CB12-10-6 glycoconjugate was effective at eliciting an immune response which was reactive with both the oligosaccharide and the meningococcal B OMP epitopes expressed in the recombinant flagellin. As shown in Table 5B, as little as three weeks into the study, mice immunized with 1 μg of MenC-CB12-10-6 conjugate in complete Freund's adjuvant had detectable antibody to MenC-HSA, OMP and to both the CB1 and CB2 epitopes. Further, all of the MenC-CB12-10-6 preparations, regardless of adjuvant, elicited antibody response to MenC-HSA which were greater than the response observed following immunization with MenC-CRM197.

TABLE 5B

Immunogenicity of Meningococcal C-recombinant flagellin vaccine one week after secondary immunization.

| IMMUNOGEN | | Dose | ELISA TITERS[1] MenC-HSA | OMP | CB1-BSA | CB2-BSA | FLAGELLIN |
|---|---|---|---|---|---|---|---|
| MenC-CB12-10-6 | CFA | 10 | 24,530 | 608 | 5,240 | 432 | 541,467 |
| | | 1 | 5,069 | 5,614 | 5,375 | 12,685 | 526,593 |
| | alum[2] | 10 | 11,845 | 253 | 835 | 673 | 472,766 |
| | | 1 | 4,415 | 136 | 242 | 244 | 214,263 |
| | None | 10 | 11,497 | 920 | 626 | 2,382 | 233,307 |
| | | 1 | 4,920 | 483 | 1,123 | 1,210 | 135,625 |
| MenC-CRM197 | alum | 10 | 4,905 | ND | ND | ND | ND |
| | | 1 | 8,505 | ND | ND | ND | ND |
| OMP (P1.16) | alum | 10 | ND | 12,907 | <100 | <100 | ND |
| | | 1 | ND | 10,405 | <100 | 3,377 | ND |

[1]Titers for initial prebleed samples (week 0) samples were <100.
[2]Aluminum phosphate was used as adjuvant at 1 mg/ml.

Example 16

T-Cell Epitopes of Class 1 OMP and Their Identification

An effective vaccine must contain one or more T-cell epitopes. T-cell epitopes within a protein can be predicted as described by Margalit et al., *J. Immunol.* 138:2213, (1987) or Rothbard and Taylor, *EMBO J.* 7:93, (1988). These predictive methods were applied to the amino acid sequence of the Class 1 OMP of *N. meningitidis* strains P1.7,16, P1.16 and P1.15. The segments of the sequence containing potential T cell epitopes identified by these methods are shown in Tables 6 and 7. The predicted peptides were synthesized by standard FMOC procedures, purified by standard methods and were identified as shown in Table 8.

To determine which of the predicted peptides actually contain T cell epitopes, their capacity to stimulate human peripheral blood lymphocytes (PBL) was tested by lymphocyte proliferative assay. Briefly, peripheral blood was collected from HLA typed normal volunteers or from volunteers who were previously immunized with MPC-2 (Poolman, J. T. et al., *Antonie van Leeuwenhoek,* 53:413–419, 1987) which contained P1.16, 15, Class 4 OMP and Group C polysaccharide. Lymphocytes were isolated from the peripheral blood by isolation on FICOLLHYPAQUE (Pharmacia Fine Chemicals AB, Uppsala, Sweden) and cultured at $1\times10^5$ cells/well in supplemented RPMI 1640 medium (Gibco Laboratories, Paisly, Scotland) containing 10% heat-inactivated pooled human AB serum. Cultures were challenged with various concentrations of the predicted T cell epitopes (0.05–10 μg/ml). After in vitro challenge, the cultures were incubated for six days and then pulsed (18 hours) with 0.5 μCi of -thymidine. Cultures were then harvested and counted by liquid scintillation. Data are expressed as stimulation indices which were calculated as a ratio of the CPM obtained in the presence of antigen to the CPM obtained in the absence of antigen.

As shown in Table 9, 10 of the 16 predicted peptides showed some capacity to stimulate T-cells. These include the peptides identified at 16–34, 47–59, 78–90, 103–121, 124–137, 151–158, 176–185, 223–245, 276–291 and 304–322. In some instance, peptides stimulated a response in both immunized as well as non-immune individuals. The response in the non-immune individuals may be attributed to a previous asymptomatic infection.

In the case of the T cell epitope identified as region 176–185, enhancement of the T cell response was observed following addition of the monoclonal antibody MN5C11G (P1.16). Briefly, PBL were challenged in vitro with a synthetic peptide containing the region 175–185 or with this peptide mixed with varying dilutions of MN5C11G. As shown in Table 10, enhancement of the T cell response was observed following addition of MN5C11G indicating that monoclonal antibody recognized a B cell epitope within the region 176–185 and facilitates the presentation of the peptide to the immune system. Thus, it was established that the T and B cell epitopes either coincide or are found on contiguous sequences within the Class 1 OMP.

In several cases, T cell lines and clones were established from individuals responding to various peptides. Briefly, T cell lines were obtained by culturing isolated lymphocytes in 24 well plates at $1\times10^6$ cells/ml. The culture medium, supplemented RPMI-1640 with 10% human serum, also contained 12 U/ml recombinant IL-2 (Boehringer). In addition, $5\times10^4$ homologous, irradiated (3,000 R) antigen presenting cells (APC) were also added to each well. In some cases, APC were obtained from HLA compatible donors. From the lines, T cell clones were isolated by limiting dilution at a frequency of 0.5 cells/well. Clones were maintained by bi-weekly stimulation with antigen in the presence of irradiated APC and IL-2 (2 U/ml). Clones were tested by lymphocyte proliferation assay essentially as described above except that clones were cultured at $1\times10^4$ cells/well in the presence of irradiated APC.

Clones obtained as described were challenged in vitro with OMP from 7 different strains of meningococci. As shown in Table 11, the clones recognized a T cell epitope or epitopes common to the seven OMPs examined. Although the reactivity of these clones to the various peptides remains to be determined, the data, nevertheless, does indicate the commonality of T cell epitopes among the various strains. Now that these clones have been established and identified their peptide reactivity will indicate T-cell epitopes for vaccine use.

TABLE 6

ANALYSIS OF THE SEQUENCE OF *N. MENINGITIDIS* P1.16 OMP FOR THE PRESENCE OF AMPHIPATHIC α-HELICIES ACCORDING TO THE METHOD OF MARGALIT ET AL. (J. IMMUNOL. 138:2213, 1987)

| | | | MID POINTS OF BLOCKS | ANGLES | AS |
|---|---|---|---|---|---|
| | | P | 47–50 | 85–105 | 9.4 |
| | | | 69–74 | 105–135 | 16.0 |
| | K | | 79–88 | 90–120 | 23.0 |
| | | | 127–135 | 100–120 | 22.4 |
| * | | | 199–202 | 90–120 | 8.4 |
| | | P | 208–211 | 85–95 | 8.7 |
| | | | 260–263 | 90–125 | 8.8 |
| | | P | 265–269 | 90–120 | 11.3 |
| | | | 274–277 | 105–120 | 9.8 |
| | | | 297–300 | 100–135 | 9.1 |
| | | P | 320–324 | 80–100 | 10.9 |
| * | | | 338–342 | 105–135 | 12.3 |
| * | | | 346–351 | 80–115 | 11.9 |
| * | | | 376–379 | 85–120 | 9.5 |

TABLE 7

PRESENCE OF MOTIFS (UNDERLINED REGIONS) REPRESENTING POTENTIAL T CELL EPITOPES WITHIN THE SEQUENCES OF *N. MENINGITIDIS* P1.16 OMP (SEQ ID NO: 191) AS DETECTED BY THE METHOD OF ROTHBARD AND TAYLOR (EMBO J 7:93, 1988).

M R K K L T A L V L S A L P L A A V A D V S L Y G E I K A G V E G R N I (SEQ ID NO:5)

Q A Q L T E Q P Q V T N G V Q G N Q V K V T K A K S R I R T K I S D F G

S F I G F K G S E D L G E G L K A V W Q L E Q D V S V A G G G A S Q W G

N R E S F I G L A G E F G T L R A G R V A N Q F D D A S Q A I N P W D S

N N D V A S Q L G I F K R H D D M P V S V R Y D S P E F S G F S G S V Q

F V P A Q N S K S A Y K P A Y Y T K D T N N N L T L V P A V V G K P G S

D V Y Y A G L N Y K N G G F A G N Y A F K Y A R H A N V G R N A F E L F

TABLE 7-continued

PRESENCE OF MOTIFS (UNDERLINED REGIONS) REPRESENTING POTENTIAL T CELL EPITOPES WITHIN THE SEQUENCES OF *N. MENINGITIDIS* P1.16 OMP (SEQ ID NO: 191) AS DETECTED BY THE METHOD OF ROTHBARD AND TAYLOR (EMBO J 7:93, 1988).

L I G S A T S D E A K G T D P L K N H Q V H R L T G G Y E E G G L N L A

L A A Q L D L S E N G D K A K T K N S T T E I A A T A S Y R F G N A V P

R I S Y A H G F D L I E R G K K G E N T S Y D Q I I A G V D Y D F S K R

T S A I V S G A W L K R N T G I G N Y T Q I N A A S V G L R H K F

TABLE 8

SUMMARY OF PREDICITED T CELL EPITOPES SYNTHESIZED.

| | RESIDUE NO. | SEQUENCE |
|---|---|---|
| 1. | 16–34 | NIQAQLTEQPQVTNGVQGN (SEQ ID NO:41) |
| 2. | 47–59 | TKISDFGSFIGFK (SEQ ID NO:42) |
| 3. | 57–71 | GFKGSEDLGEGLKAV (SEQ ID NO:43) |
| 4. | 78–90 | VSVAGGGASQWGN (SEQ ID NO:44) |
| 5. | 103–121 | TLRAGRVANQFDDASQAIN (SEQ ID NO:45) |
| 6. | 124–137 | DSNNDVASQLGIFK (SEQ ID NO:46) |
| 7. | 151–158 | GGFSGFSG (SEQ ID NO:47) |
| 8. | 176–185 | YYTKDTNNNL (SEQ ID NO:47) |
| 9. | 190–202 | AVVGKPGSDVYYA (SEQ ID NO:48) |
| 10. | 215–228 | YAFKYARNAHVGRN (SEQ ID NO:49) |

TABLE 8-continued

SUMMARY OF PREDICITED T CELL EPITOPES SYNTHESIZED.

| | RESIDUE NO. | SEQUENCE |
|---|---|---|
| 11. | 223–245 | ANVGRNAFELFLIGSATSDEAKG (SEQ ID NO:50) |
| 12. | 241–261 | DEAKGTDPLKNHQVHRLTGGY (SEQ ID NO:51) |
| 13. | 276–291 | LSENGDKAKTKNSTTE (SEQ ID NO:52) |
| 14. | 304–322 | VPRISYAHGFDLIERGKKG (SEQ ID NO:53) |
| 15. | 317–329 | ERGKKGENTSYDQ (SEQ ID NO:54) |
| 16. | 352–366 | KRNTGIGNYTQINAA (SEQ ID NO:55) |

TABLE 9

SUMMARY OF LYMPHOCYTE RESPONSES TO MENINGOCOCCAL SYNTHETIC PEPTIDES IN HLA TYPED VOLUNTEERS.

| | RESPONSE TO SYNTHETIC PEPTIDE | | | | | | | | | | | | | | | |
|---|---|---|---|---|---|---|---|---|---|---|---|---|---|---|---|---|
| VOLUNTEER/HLA TYPE | 1 | 2 | 3 | 4 | 5 | 6 | 7 | 8 | 9 | 10 | 11 | 12 | 13 | 14 | 15 | 16 |
| IMMUNIZED VOLUNTEERS | | | | | | | | | | | | | | | | |
| 1. DR4,W10,W53 | | − | − | | | | | + | − | − | | − | | − | | − |
| 2. DR3,W52 | | | | | − | + | | + | − | | + | | | | | |
| 3. DR3,7,W52,W53 | | − | − | | − | | − | + | − | − | − | − | − | + | | − |
| 4. DR2,W6,W13,W15,W52 | | + | − | | − | | + | | − | − | | | | | | − |
| 5. DR5,W11,7,W52,W53 | + | | − | | | | − | + | − | − | + | − | | + | | ± |
| 6. DR5,W11,W10,W52 | | | | | | | | | | | | | | | | |
| NON-IMMUNIZED CONTROL VOLUNTEERS | | | | | | | | | | | | | | | | |
| 7. NOT TYPED | − | − | − | + | − | + | − | ± | − | − | ± | − | ± | − | − | − |
| 8. DRW13,W6,W52 | − | − | − | − | − | − | − | − | − | − | − | − | − | − | − | − |
| 9. DR2,W15,4,W53 | | − | | | − | | − | − | − | − | ± | − | | − | − | − |
| 10. NOT TYPED | − | − | − | − | − | − | − | − | − | − | − | − | − | − | − | − |
| 11. NOT TYPED | | | − | | − | | − | + | − | − | | − | | − | | − |
| 12. DR2,W15,3,W52 | − | + | − | | − | − | − | − | − | − | + | − | − | − | − | − |
| 13. DR5,W11,W52 | − | − | − | | − | − | | + | − | − | − | − | − | − | − | − |
| 14. DR3,7,W52,W53 | − | − | − | | − | | | + | − | − | − | − | − | + | − | − |
| 15. DR3,4,W52,W53 | − | − | − | | − | + | − | − | − | − | − | − | − | − | − | − |
| 16. DR3,W12,5,W52 | | | | | | | | | | | | | | | | |
| 17. DR2,W15,7,W53 | | | | | | | | | | | | | + | | | |
| 18. DR1,3,W52 | | | | | | | | | | | | | | | | |
| 19. DR3,4,W52,W53 | | | | | | | | + | | | | | | | | |
| 20. DR1,7,W53 | | | | | | | | | | | ± | | | | | |
| 21. DR4,W8,W52,W53 | | | | | | | | | | | | | | | | |
| 22. DR1,W13,W6,W52 | | | | | | | | | | | | | | | | |
| 23. DR2,W16,5,W11,W52 | | | | | ± | | | + | | | + | | + | | | |
| 24. DR5,W11,W6,W13,W52 | | | | | | | | ± | | | ± | | | | | |
| 25. DR1,3 W52 | | | | | | | | ± | | | | | | | | |
| 26. DR1,W6,W13,W52 | | + | | + | | | | | | | | | | | | |

TABLE 9-continued

SUMMARY OF LYMPHOCYTE RESPONSES TO MENINGOCOCCAL SYNTHETIC PEPTIDES IN HLA TYPED VOLUNTEERS.

| | RESPONSE TO SYNTHETIC PEPTIDE | | | | | | | | | | | | | | | |
|---|---|---|---|---|---|---|---|---|---|---|---|---|---|---|---|---|
| VOLUNTEER/HLA TYPE | 1 | 2 | 3 | 4 | 5 | 6 | 7 | 8 | 9 | 10 | 11 | 12 | 13 | 14 | 15 | 16 |
| 27. DRW6,W13,W52 | | | | | | | | | | | | | | | | |
| 28. DRW6,W13,W52 | | | | | | | | + | | | | | | | | |

The responses were scored as follows −, SI < 2; ±, 2 < SI < 3 and +, SI > 3.

TABLE 10

PRESENTATION OF A SYNTHETIC PEPTIDE TO PERIPHERAL BLOOD LYMPHOCYTES IS ENHANCED BY A MONOCLONAL ANTIBODY RECOGNIZING REGION 179–184 OF MENINGOCOCCAL CLASS 1 OMP.

| IN VITRO CHALLENGE | CPM |
|---|---|
| GGYYTKDTNNNL (SEQ ID NO:56) | 3,017 |
| GGYYTKDTNNNL * SEQ ID NO:56 + MN5C11G (1:200) | 22,836 |
| GGYYTKDTNNNL SEQ ID NO:56 + MN5C11G (1:1000) | 12,608 |
| MEDIA | 330 |

*Underline region indicates sequence recognized by monoclonal antibody MN5C11G.

TABLE 11

RECOGNITION OF OMP FROM DIFFERENT MENINGOCOCCAL STRAINS BY HUMAN T-CELL CLONES

| | SUB- | RESPONSE OF HUMAN T CELL CLONES (CPM × $10^{-3}$) | | | | | | |
|---|---|---|---|---|---|---|---|---|
| STRAIN | TYPE | 5-5 | 5-7 | 5-9 | 5-12 | 5-13 | 5-14 | 5-15 |
| H44-76 | P1.16 | 6.0 | 1.2 | 6.8 | 2.6 | 2.3 | 9.5 | 1.5 |
| SWISS | P1.15 | 4.9 | 1.0 | 10.1 | 6.9 | 3.6 | 10.5 | 1.4 |
| 395 | P1.9 | 5.2 | 1.5 | 4.8 | 1.5 | 6.1 | 13.1 | 1.4 |
| 2996 | P1.2 | 5.4 | 1.0 | 3.7 | 2.3 | 3.4 | 11.8 | 1.0 |
| M990 | P1.6 | 3.6 | 0.4 | 3.5 | 2.5 | 0.9 | 4.7 | 0.6 |
| 187 | P1.1 | 4.4 | 0.7 | 4.5 | 3.1 | 1.6 | 6.2 | 1.4 |
| 6557 | P1.17 | 3.7 | 2.0 | 8.2 | 4.2 | 1.7 | 6.2 | 0.8 |
| MEDIA | — | <0.1 | <0.1 | <0.1 | <0.1 | <0.1 | <0.1 | <0.1 |

Example 17

Construction of Protein Model for Membrane Topology of Class 1 OMP and Comparison to Other Pathogenic Gram Negative Porin Proteins for Vaccine Development A model was constructed using the principles recognized for the structure of several *Escherichia coli* outer membrane Proteins (Vogel, H. et al. (1986) supra Ferenci, T. et al. (1988) supra; and Tommassen, J. (1988) supra). The central assumption is that protein segments spanning the outer membrane form beta-sheets. Specifically, in the case of Class 1 protein, the division in exposed and transmembrane segments was arrived at in the following way:

1. A comparison of the amino acid sequence of Class 1 protein (subtype P1.16) with those of the gonococcal PIA and PIB proteins (Carbonetti, N. H. et al. (1987) *PNAS* 84:9084; Carbonetti, N. H. et al. (1988) *PNAS* 85:6841; and Gotschlich, E. C. et al. (1987) *PNAS* 84:8135) reveals 34% identity. In the model, the variable sequences form the surface-exposed parts, whereas the conserved regions are placed mostly in the outer membrane and periplasm. Thus, the latter two areas consist for 58% of residues that are conserved among all proteins,
2. The hydrophilic maxima observed in a hydropathy profile (Kyte, J. et al. (1982) *J. Mol. Biol.* 157:105) to correspond to exposed regions.
3. The transmembrane segments should preferentially be able to form amphipathic beta-stands of 9–12 residues, with at least one side consisting entirely of hydrophobic residues. These conditions are met in 12 of the 16 membrane-spanning segments.
4. The number of residues at the periplasmic side is minimized.

Figure 11:
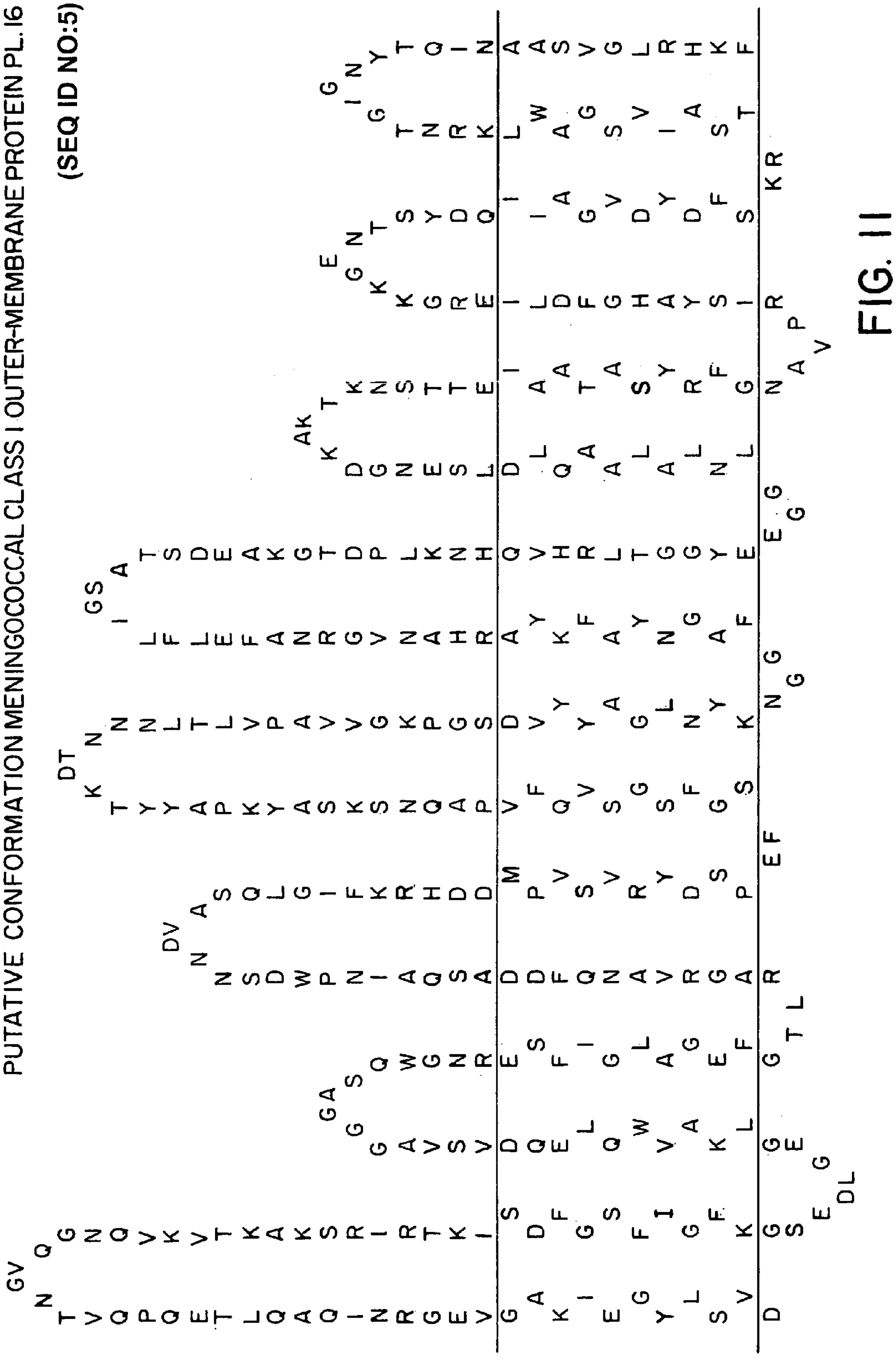
FIG. 11 (see also SEQ ID NO:5). Putative conformation of *N. Meningitidis* Class 1 OMP subtype P1.16.

FIG. 11 shows the model for the folding of Class 1 protein in the outer membrane. The sequence shown is for subtype P1.16. The top part of the figure shows the surface-exposed regions, whereas the central part indicates the presumed transmembrane segments, whose length is set at ten. Amino acid are shown alternating where they can form an amphipathic beta-strand. This model contains eight surface loops, whereby the first and the fourth loop contain the type-specific and protective variable region epitopes. These epitopes, as has been shown when formulated into a vaccine, can elicit a protective immune response. Loop 5 is constant and has been shown to elicit cross-reactive antibodies to other OMPs and is useful for vaccine formulation.

The one or two variable epitope regions of the individual proteins are located on so called surface loops of these membrane proteins. Such porin outer-membrane proteins contain more than two surface loops. This implicates that there are surface loops which have near identical amino acid sequence in the different Class 1 outer-membrane proteins as well. This opens the way to use of common peptides of the Class 1 outer-membrane protein for vaccine objectives as well. More especially a schematic two-dimensional model of the meningococci Class 1 outer-membrane protein P1,16 is illustrated in FIG. 11 (see also SEQ ID NO:5). This model contains eight surface loops, whereby the first and the fourth loop contain the type specific epitopes as shown on the basis of strain subtyping results. The fifth surface loop represents the constant region described above. Antibody to the constant region of loop 5 appears to react with *N. meningitidis* OMP complex. The amino sequence of Class 1 OMP, as derived, was compared to the Class 2 OMP of *N. meningitidis* (Murakami, K. et al., (1989), *Infect. Immun.,* 57:2318) and the porin PIA and PIB proteins of *N. gonorrhoeae*. With similar principle as used for the Class 1 OMP modeling, the sequences were aligned as follows:

```
                                  LOOP 1
Class  1 (SEQ ID NO:57) DVSLYGEIKAG
                        ** *** ****
Class IB (SEQ ID NO:58) DVTLYGAIKAG
                        ** *** ****
Class IA (SEQ ID NO:59) DVTLYGTIKAG
                        ** *** ****
Class  2 (SEQ ID NO:60) DVTLYGTIKAGV
                        ** *** *****

      VEGRNIQAQLTEQPQVTNGVQGNQVKVTKAKSRIRTKI
      *                                    *
      V-------------QTYRSVEHTDGKVSKVET--GSEI
      *                                    *
      VEGRNIQAQLTEQPETSRSVAHHGAQADRVKT--ATEI
      *                                    *
      EGRNIQAQLTEQPEVSRVKDAGTYKAQGGKSKTATQ
                                    SDFGSTIGFKGSEDLGEGL
                                      * ** ***** **** **
                                    ADFGSKIGFKGQEDLGNGL
                                      ** ***** ** * **
                                    ADLGSKIGFKGQEDLGNGL
                                      * ** ***** ** * **
                                    IADFGSKIGFKGQEDLGNGL
                                    * * ** ***** ** * **

                    LOOP 2
        KAVWQLEQD VSVAGGGASQWGN RESFIGLAGEFG
        ** *****       *    ***  ** ** * **
        KAVWQLEQG ASVAGTNTG-WGN KQSFVGLKGGFG
        ** *****       *    ***  ** ** * **
        KAIWQLEQK AYVSGTDTG-WGN RQSFIGLKGGFG
        ** *****       *    ***   ** ** * **
        KAIWQLEQ  KASIAGTNSG-WGNRQSFIGLKGGFG
        ** *****       *    ***  ** ** * **

LOOP 3
TLRAGRVANQFDD ASQAINPWDSNNDVASQLQI-
  * *
TIRAGSLNSPLKN TGANVNAWESGKFTGNVLEIS
  * *
KVRVGRLNSYLKD TGGFNPWEGKSYYLPLSNIAQ
  * *
TVRAGNLNTVLKDSGDNVNAWESGSNTEDVLGLG
  * *

                                         LOOP 4
      -FKRHDD MPV SVRYDSPEFSGFSGSVQFV PAQNS
                  *******    **     *  *  **
      GMAQREH RYL SVRYDSPEFAGFSGSVQYA PKDNS
                  *******    **     *  *  **
      PEERHV-- -- SVRYDSPEFAGFRAV-QYV PNDNS
                  *******    **     *  *  **
      TIGRVESREI  SVRYDSPVFAGFSGSVQ  YVPRDNA
                  *******    **    *   *  **

              KSAYKPAYYTKDTNNNLTLVPAVVGRPGS DVYYA
                                              *
              GS--------------------------NG ESYHV
                                              *
              GK-------------------------NHS ESYHA
                                              *
              ND----------------VDKYKHTKSSR ESYHA
                                              *

            LOOP 5
GLNYKNGGFAGNYAFKYA RHANVGRNAFELFLIG
* ** * * *   **
GLNYQNSGFFAQYAGLFQ RYGEGTKK------IE
* ** * * *   **
GFNYKNSGFFVQYAGFYK  RHSYTTEKHFELFL--
* ** * * *   **
GLKYENAGFFGQYA GSFAKYADLNTD------AE
* ** * * *   **

                            N
             SATSDEAKGTDPLKH QVHRLTGGYEEGGLNLALA
                             ***** ***     *    *
             DDGTYSIPSLFVEKL QVHRLVGGYDNNALYVSVA
                             ***** ***     *    *
             --------------L QVHRLVGGYDHDALYASVA
                             ***** ***     *    *
             RVAVNTANAHPVKDY QVHRVVAGYDANDLYVSVA
                             ***** ***     *    *
```

-continued

```
           LOOP 6
    AQLD LSE--NGDKAKTKNSTTE IAATASYRFGNA
     *                  *    **** *****
    AQQQ DAKLYGAMSGNSHNSQTE VAATAAYRFGNV
     *                  *    **** *****
    VQQQ DAKLTWRND-NSHNSQTE VAATAAYRFGNV
     *                  *  *  **** ****
    GQ  YEAAKNNEVGSTKGKKHQTQ VAATAAYRFGNV
     *                  E *  **** *****

                  LOOP 7
    VPRISYAHGFDLI ERGKKGENTSYDQ IIAGVDYD
     ** ******          *   * *       **
    TPRVSYAHGFKGT VDSANHDNT-YDQ VVVGAEYD
    ** ******           *   * *       **
    TPRVSYAHGFKGS VYDADNDNT-YDQ VVVGAEYD
    ** ******           *   * *       **
    TPRVSYAHGF  KAKVNGVKDANYQQDQ VIVGADYD
    ** ******               *  *    *  **

                      LOOP 8
  FSKRTSAIVSGAWL KRNTGIGNYTQIN AASVGLRHKF
  ******* **  **   *               * *****
  FSKRTSALVSAGWL QGGKGADKIV-ST ASAVVLRHKF
  ******* **  **   *               * *****
  FSKRTSALVSAGWL QRGKGTEKFV-AT VGGVGLRHKF
  ******* **  **   *               * *****
  FSKRTSALVSAGWL  KQGKGTGKVEQ-TASM VGLRHKF
  ******* **  **   *               * *****
```

Structural similarities are indicated with transmembrane and surface loop regions. With the information now available for Class 1 OMP and information based on surface loop size, location, intraspecies amino acid homology or heterology of the loop regions of the particular porin protein, predictions of epitopes for incorporation into vaccines for other pathogenic gram negative bacteria including *N. gonorrhoeae* are possible. Using the same methods employed for Class 1 OMP, these epitopes can be evaluated for vaccine purposes.

DEPOSIT OF MICROORGANISMS

The *N. meningitidis* strain H4476 (B:15:P1.7,16) was deposited on Dec. 11, 1989 in the Centraal Bureau voor Schimmelculturen (CBS), Baarn, The Netherlands and has deposit number CBS 635.89. The *N. meningitidis* Class 2/3 OMP deficient mutant HIII-5 was deposited on Dec. 11, 1989 in the CBS, Baarn, The Netherlands and has deposit number CBS 636.89.

*Neisseria meningitidis* strain HIII-5 was deposited in accordance with the provisions of the Budapest Treaty at the American Type Culture Collection (ATCC), 10801 University Boulevard, Manassass Va. 20110-2209, USA, on Jan. 23, 2003, and assigned ATCC Accession Number PTA-4953.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A vaccine comprising purified *Neisseria meningitidis* Class 1 outer-membrane proteins of more than one subtype, in a pharmaceutically acceptable vehicle.

2. The vaccine of claim 1 wherein at least one of said Class 1 outer-membrane proteins consists of an amino acid sequence selected from the group consisting of: SEQ ID NO:5, SEQ ID NO:6, SEQ ID NO:7, and SEQ ID NO:8.

3. The vaccine of claim 1, wherein the Class 1 outer-membrane proteins are from serogroup A, B or C.

4. The vaccine of claim 1 wherein at least one of the Class 1 outer-membrane proteins is subtype P1.16, P1.15, or P1.7,16.

5. The vaccine of claim 1 further comprising a lipid or a detergent.

6. A vaccine comprising purified meningococcal Class 1 outer-membrane proteins of more than one subtype, in a pharmaceutically acceptable vehicle, wherein the vaccine elicits antibodies against said meningococcal Class 1 outer-membrane proteins in a mammal.

7. The vaccine of claim 6 further comprising a lipid or a detergent.

8. An antigenic composition comprising a conjugate of a surface loop peptide of *Neisseria meningitidis* Class 1 outer-membrane protein linked to a carrier protein.

9. The composition of claim 8 wherein the carrier protein is tetanus toxoid.

* * * * *

SEQUENCE LISTING

<160> NUMBER OF SEQ ID NOS: 193

<210> SEQ ID NO 1
<211> LENGTH: 30
<212> TYPE: PRT
<213> ORGANISM: Neisseria meningitidis
<220> FEATURE:
<221> NAME/KEY: VARIANT
<222> LOCATION: 26
<223> OTHER INFORMATION: Xaa = Any Amino Acid

<400> SEQUENCE: 1

```
Asp Val Ser Leu Tyr Gly Glu Ile Lys Ala Gly Val Glu Asp Arg Asn
 1               5                  10                  15

Tyr Gln Leu Gln Leu Thr Glu Ala Gln Xaa Ala Ala Gly Asn
            20                  25                  30
```

<210> SEQ ID NO 2
<211> LENGTH: 42
<212> TYPE: PRT
<213> ORGANISM: Neisseria meningitidis
<220> FEATURE:
<221> NAME/KEY: VARIANT
<222> LOCATION: 24
<223> OTHER INFORMATION: Xaa = Any Amino Acid

<400> SEQUENCE: 2

```
Pro Val Ser Val Arg Tyr Asp Ser Pro Glu Phe Ser Gly Phe Ser Gly
 1               5                  10                  15

Ser Val Gln Phe Val Pro Ile Xaa Asn Ser Lys Ser Ala Tyr Thr Pro
            20                  25                  30

Ala Tyr Tyr Thr Lys Asp Thr Asn Asn Asn
        35                  40
```

<210> SEQ ID NO 3
<211> LENGTH: 30
<212> TYPE: PRT
<213> ORGANISM: Neisseria meningitidis

<400> SEQUENCE: 3

```
Phe Ser Gly Phe Ser Gly Ser Val Gln Phe Val Pro Ile Gln Asn Ser
 1               5                  10                  15

Lys Ser Ala Tyr Thr Pro Ala Tyr Tyr Thr Lys Asp Thr Asn
            20                  25                  30
```

<210> SEQ ID NO 4
<211> LENGTH: 37
<212> TYPE: PRT
<213> ORGANISM: Neisseria meningitidis

<400> SEQUENCE: 4

```
Pro Val Ser Val Arg Tyr Asp Ser Pro Glu Phe Ser Gly Phe Ser Gly
 1               5                  10                  15

Ser Val Gln Phe Val Pro Ile Gln Asn Ser Lys Ser Ala Tyr Thr Pro
            20                  25                  30

Ala Tyr Tyr Thr Lys
        35
```

<210> SEQ ID NO 5
<211> LENGTH: 374
<212> TYPE: PRT
<213> ORGANISM: Neisseria meningitidis -continued

<400> SEQUENCE: 5

```
Asp Val Ser Leu Tyr Gly Glu Ile Lys Ala Gly Val Glu Gly Arg Asn
 1               5                  10                  15

Ile Gln Ala Gln Leu Thr Glu Gln Pro Gln Val Thr Asn Gly Val Gln
            20                  25                  30

Gly Asn Gln Val Lys Val Thr Lys Ala Lys Ser Arg Ile Arg Thr Lys
        35                  40                  45

Ile Ser Asp Phe Gly Ser Phe Ile Gly Phe Lys Gly Ser Glu Asp Leu
    50                  55                  60

Gly Glu Gly Leu Lys Ala Val Trp Gln Leu Glu Gln Asp Val Ser Val
65                  70                  75                  80

Ala Gly Gly Gly Ala Ser Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asn Pro Trp Asp Ser Asn Asn Asp
        115                 120                 125

Val Ala Ser Gln Leu Gly Ile Phe Lys Arg His Asp Asp Met Pro Val
    130                 135                 140

Ser Val Arg Tyr Asp Ser Pro Glu Phe Ser Gly Phe Ser Gly Ser Val
145                 150                 155                 160

Gln Phe Val Pro Ala Gln Asn Ser Lys Ser Ala Tyr Lys Pro Ala Tyr
                165                 170                 175

Tyr Thr Lys Asp Thr Asn Asn Asn Leu Thr Leu Val Pro Ala Val Val
            180                 185                 190

Gly Lys Pro Gly Ser Asp Val Tyr Tyr Ala Gly Leu Asn Tyr Lys Asn
        195                 200                 205

Gly Gly Phe Ala Gly Asn Tyr Ala Phe Lys Tyr Ala Arg His Ala Asn
    210                 215                 220

Val Gly Arg Asn Ala Phe Glu Leu Phe Leu Ile Gly Ser Ala Thr Ser
225                 230                 235                 240

Asp Glu Ala Lys Gly Thr Asp Pro Leu Lys Asn His Gln Val His Arg
                245                 250                 255

Leu Thr Gly Gly Tyr Glu Glu Gly Gly Leu Asn Leu Ala Leu Ala Ala
            260                 265                 270

Gln Leu Asp Leu Ser Glu Asn Gly Asp Lys Ala Lys Thr Lys Asn Ser
        275                 280                 285

Thr Thr Glu Ile Ala Ala Thr Ala Ser Tyr Arg Phe Gly Asn Ala Val
    290                 295                 300

Pro Arg Ile Ser Tyr Ala His Gly Phe Asp Leu Ile Glu Arg Gly Lys
305                 310                 315                 320

Lys Gly Glu Asn Thr Ser Tyr Asp Gln Ile Ile Ala Gly Val Asp Tyr
                325                 330                 335

Asp Phe Ser Lys Arg Thr Ser Ala Ile Val Ser Gly Ala Trp Leu Lys
            340                 345                 350

Arg Asn Thr Gly Ile Gly Asn Tyr Thr Gln Ile Asn Ala Ala Ser Val
        355                 360                 365

Gly Leu Arg His Lys Phe
    370
```

<210> SEQ ID NO 6
<211> LENGTH: 368
<212> TYPE: PRT
<213> ORGANISM: Neisseria meningitidis -continued

<400> SEQUENCE: 6

```
Asp Val Ser Leu Tyr Gly Glu Ile Lys Ala Gly Val Glu Gly Arg Asn
 1               5                  10                  15

Phe Gln Leu Gln Leu Thr Glu Pro Pro Ser Lys Ser Gln Pro Gln Val
            20                  25                  30

Lys Val Thr Lys Ala Lys Ser Arg Ile Arg Thr Lys Ile Ser Asp Phe
        35                  40                  45

Gly Ser Phe Ile Gly Phe Lys Gly Ser Glu Asp Leu Gly Glu Gly Leu
    50                  55                  60

Lys Ala Val Trp Gln Leu Glu Gln Asp Val Ser Val Ala Gly Gly Gly
65                  70                  75                  80

Ala Thr Gln Trp Gly Asn Arg Glu Ser Phe Val Gly Leu Ala Gly Glu
                85                  90                  95

Phe Gly Thr Leu Arg Ala Gly Arg Val Ala Asn Gln Phe Asp Asp Ala
            100                 105                 110

Ser Gln Ala Ile Asp Pro Trp Asp Ser Asn Asn Asp Val Ala Ser Gln
        115                 120                 125

Leu Gly Ile Phe Lys Arg His Asp Asp Met Pro Val Ser Val Arg Tyr
    130                 135                 140

Asp Ser Pro Asp Phe Ser Gly Phe Ser Gly Ser Val Gln Phe Val Pro
145                 150                 155                 160

Ile Gln Asn Ser Lys Ser Ala Tyr Thr Pro Ala His Tyr Thr Arg Gln
                165                 170                 175

Asn Asn Thr Asp Val Phe Val Pro Ala Val Val Gly Lys Pro Gly Ser
            180                 185                 190

Asp Val Tyr Tyr Ala Gly Leu Asn Tyr Lys Asn Gly Gly Phe Ala Gly
        195                 200                 205

Ser Tyr Ala Phe Lys Tyr Ala Arg His Ala Asn Val Gly Arg Asp Ala
    210                 215                 220

Phe Glu Leu Phe Leu Leu Gly Ser Thr Ser Asp Glu Ala Lys Gly Thr
225                 230                 235                 240

Asp Pro Leu Lys Asn His Gln Val His Arg Leu Thr Gly Gly Tyr Glu
                245                 250                 255

Glu Gly Gly Leu Asn Leu Ala Leu Ala Ala Gln Leu Asp Leu Ser Glu
            260                 265                 270

Asn Gly Asp Lys Ala Lys Thr Lys Asn Ser Thr Thr Glu Ile Ala Ala
        275                 280                 285

Thr Ala Ser Tyr Arg Phe Gly Asn Ala Val Pro Arg Ile Ser Tyr Ala
    290                 295                 300

His Gly Phe Asp Leu Ile Glu Arg Gly Lys Lys Gly Glu Asn Thr Ser
305                 310                 315                 320

Tyr Asp Gln Ile Ile Ala Gly Val Asp Tyr Asp Phe Ser Lys Arg Thr
                325                 330                 335

Ser Ala Ile Val Ser Gly Ala Trp Leu Lys Arg Asn Thr Gly Ile Gly
            340                 345                 350

Asn Tyr Thr Gln Ile Asn Ala Ala Ser Val Gly Leu Arg His Lys Phe
        355                 360                 365
```

<210> SEQ ID NO 7
<211> LENGTH: 373
<212> TYPE: PRT
<213> ORGANISM: Neisseria meningitidis -continued

<400> SEQUENCE: 7

```
Asp Val Ser Leu Tyr Gly Glu Ile Lys Ala Gly Val Glu Gly Arg Asn
 1               5                  10                  15

Tyr Gln Leu Gln Leu Thr Glu Ala Gln Ala Ala Asn Gly Gly Ala Ser
            20                  25                  30

Gly Gln Val Lys Val Thr Lys Val Thr Lys Ala Lys Ser Arg Ile Arg
        35                  40                  45

Thr Lys Ile Ser Asp Phe Gly Ser Phe Ile Gly Phe Lys Gly Ser Glu
    50                  55                  60

Asp Leu Gly Asp Gly Leu Lys Ala Val Trp Gln Leu Glu Gln Asp Val
65                  70                  75                  80

Ser Val Ala Gly Gly Gly Ala Thr Gln Trp Gly Asn Arg Glu Ser Phe
                85                  90                  95

Ile Gly Leu Ala Gly Glu Phe Gly Thr Leu Arg Ala Gly Arg Val Ala
            100                 105                 110

Asn Gln Phe Asp Asp Ala Ser Gln Ala Ile Asp Pro Trp Asp Ser Asn
        115                 120                 125

Asn Asp Val Ala Ser Gln Leu Gly Ile Phe Lys Arg His Asp Asp Met
    130                 135                 140

Pro Val Ser Val Arg Tyr Asp Ser Pro Glu Phe Ser Gly Phe Ser Gly
145                 150                 155                 160

Ser Val Gln Phe Val Pro Ile Gln Asn Ser Lys Ser Ala Tyr Thr Pro
                165                 170                 175

Ala Tyr Tyr Thr Lys Asn Thr Asn Asn Asn Leu Thr Leu Val Pro Ala
            180                 185                 190

Val Val Gly Lys Pro Gly Ser Asp Val Tyr Tyr Ala Gly Leu Asn Tyr
        195                 200                 205

Lys Asn Gly Gly Phe Ala Gly Asn Tyr Ala Phe Lys Tyr Ala Arg His
    210                 215                 220

Ala Asn Val Gly Arg Asn Ala Phe Glu Leu Phe Leu Ile Gly Ser Gly
225                 230                 235                 240

Ser Asp Gln Ala Lys Gly Thr Asp Pro Leu Lys Asn His Gln Val His
                245                 250                 255

Arg Leu Thr Gly Gly Tyr Glu Glu Gly Gly Leu Asn Leu Ala Leu Ala
            260                 265                 270

Ala Gln Leu Asp Leu Ser Glu Asn Gly Asp Lys Thr Lys Asn Ser Thr
        275                 280                 285

Thr Glu Ile Ala Ala Thr Ala Ser Tyr Arg Phe Gly Asn Ala Val Pro
    290                 295                 300

Arg Ile Ser Tyr Ala His Gly Phe Asp Phe Ile Glu Arg Gly Lys Lys
305                 310                 315                 320

Gly Glu Asn Thr Ser Tyr Asp Gln Ile Ile Ala Gly Val Asp Tyr Asp
                325                 330                 335

Phe Ser Lys Arg Thr Ser Ala Ile Val Ser Gly Ala Trp Leu Lys Arg
            340                 345                 350

Asn Thr Gly Ile Gly Asn Tyr Thr Gln Ile Asn Ala Ala Ser Val Gly
        355                 360                 365

Leu Arg His Lys Phe
    370
```

<210> SEQ ID NO 8
<211> LENGTH: 367
<212> TYPE: PRT
<213> ORGANISM: Neisseria meningitidis -continued

<400> SEQUENCE: 8

```
Asp Val Ser Leu Tyr Gly Glu Ile Lys Ala Gly Val Glu Gly Arg Asn
 1               5                  10                  15

Ile Gln Leu Gln Leu Thr Glu Pro Leu Gln Asn Ile Gln Gln Pro Gln
            20                  25                  30

Val Thr Lys Ala Lys Ser Arg Ile Arg Thr Lys Ile Ser Asp Phe Gly
        35                  40                  45

Ser Phe Ile Gly Phe Lys Gly Ser Glu Asp Leu Gly Glu Gly Leu Lys
    50                  55                  60

Ala Val Trp Gln Leu Glu Gln Asp Val Ser Val Ala Gly Gly Gly Ala
65                  70                  75                  80

Thr Arg Trp Gly Asn Arg Glu Ser Phe Val Gly Leu Ala Gly Glu Phe
                85                  90                  95

Gly Thr Leu Arg Ala Gly Arg Val Ala Asn Gln Phe Asp Asp Ala Ser
            100                 105                 110

Lys Ala Ile Asp Pro Trp Asp Ser Asn Asn Val Val Ala Ser Gln Leu
        115                 120                 125

Gly Ile Phe Lys Arg Met Asp Asp Met Pro Val Ser Val Arg Tyr Asp
    130                 135                 140

Ser Pro Glu Phe Ser Gly Phe Ser Gly Ser Val Gln Phe Val Pro Ala
145                 150                 155                 160

Gln Asn Ser Lys Ser Ala Tyr Thr Pro Ala His Phe Val Gln Gln Thr
                165                 170                 175

Pro Gln Gln Pro Thr Leu Val Pro Ser Ala Val Val Gly Lys Pro Gly
            180                 185                 190

Ser Asp Val Tyr Tyr Ala Gly Leu Asn Tyr Lys Asn Gly Gly Phe Ala
        195                 200                 205

Gly Asn Tyr Ala Phe Lys Tyr Ala Lys His Ala Asn Val Gly Arg Asp
    210                 215                 220

Ala Phe Glu Leu Phe Leu Leu Gly Ser Gly Ser Asp Glu Ala Lys Gly
225                 230                 235                 240

Thr Asp Pro Leu Lys Asn His Gln Val His Arg Leu Thr Gly Gly Tyr
                245                 250                 255

Glu Glu Gly Gly Leu Asn Leu Ala Leu Ala Ala Gln Leu Asp Leu Ser
            260                 265                 270

Glu Asn Ala Asp Lys Thr Lys Asn Ser Thr Thr Glu Ile Ala Ala Thr
        275                 280                 285

Ala Ser Tyr Arg Phe Gly Asn Ala Val Pro Arg Ile Ser Tyr Ala His
    290                 295                 300

Gly Phe Asp Phe Ile Glu Arg Gly Lys Lys Gly Glu Asn Thr Ser Tyr
305                 310                 315                 320

Asp Gln Ile Ile Ala Gly Val Asp Tyr Asp Phe Ser Lys Arg Thr Ser
                325                 330                 335

Ala Ile Val Ser Gly Ala Trp Leu Lys Arg Asn Thr Gly Ile Gly Asn
            340                 345                 350

Tyr Thr Gln Ile Asn Ala Ala Ser Val Gly Leu Arg His Lys Phe
        355                 360                 365
```

<210> SEQ ID NO 9
<211> LENGTH: 41
<212> TYPE: DNA
<213> ORGANISM: Artificial Sequence
<220> FEATURE:
<223> OTHER INFORMATION: PCR primer -continued

<400> SEQUENCE: 9
tgtaaaacga cggccagttt gaagacgtat cgggrgtttg c 41

<210> SEQ ID NO 10
<211> LENGTH: 42
<212> TYPE: DNA
<213> ORGANISM: Artificial Sequence
<220> FEATURE:
<223> OTHER INFORMATION: PCR primer

<400> SEQUENCE: 10
tgtaaaacga cggccagtgg cgaattcggt acgctgcgcg cc 42

<210> SEQ ID NO 11
<211> LENGTH: 42
<212> TYPE: DNA
<213> ORGANISM: Artificial Sequence
<220> FEATURE:
<223> OTHER INFORMATION: PCR primer

<400> SEQUENCE: 11
tgtaaaacga cggccagtca tcaggtacac cgcctgacgg gc 42

<210> SEQ ID NO 12
<211> LENGTH: 40
<212> TYPE: DNA
<213> ORGANISM: Artificial Sequence
<220> FEATURE:
<223> OTHER INFORMATION: PCR primer

<400> SEQUENCE: 12
tgtaaaacga cggccagtgc agattggcag tcagattgca 40

<210> SEQ ID NO 13
<211> LENGTH: 40
<212> TYPE: DNA
<213> ORGANISM: Artificial Sequence
<220> FEATURE:
<223> OTHER INFORMATION: PCR primer

<400> SEQUENCE: 13
tgtaaaacga cggccagtgg gatcggtacc tttggcttga 40

<210> SEQ ID NO 14
<211> LENGTH: 40
<212> TYPE: DNA
<213> ORGANISM: Artificial Sequence
<220> FEATURE:
<223> OTHER INFORMATION: PCR primer

<400> SEQUENCE: 14
tgtaaaacga cggccagtaa ctgattcgca acgcgaccgg 40

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
ttgaaggacg tatcgggtgt ttcg 24

-continued

```
<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16

gcagattggc agtcagattg ctt                                            23


<210> SEQ ID NO 17
<211> LENGTH: 10
<212> TYPE: PRT
<213> ORGANISM: Neisseria meningitidis

<400> SEQUENCE: 17

Tyr Tyr Thr Lys Asp Thr Asn Asn Asn Leu
 1               5                  10


<210> SEQ ID NO 18
<211> LENGTH: 10
<212> TYPE: PRT
<213> ORGANISM: Neisseria meningitidis

<400> SEQUENCE: 18

Tyr Tyr Thr Lys Asn Thr Asn Asn Asn Leu
 1               5                  10


<210> SEQ ID NO 19
<211> LENGTH: 11
<212> TYPE: PRT
<213> ORGANISM: Neisseria meningitidis

<400> SEQUENCE: 19

His Tyr Thr Arg Gln Asn Asn Thr Asp Val Phe
 1               5                  10


<210> SEQ ID NO 20
<211> LENGTH: 10
<212> TYPE: PRT
<213> ORGANISM: Neisseria meningitidis

<400> SEQUENCE: 20

Ala Gln Ala Ala Asn Gly Gly Ala Ser Gly
 1               5                  10


<210> SEQ ID NO 21
<211> LENGTH: 11
<212> TYPE: PRT
<213> ORGANISM: Neisseria meningitidis

<400> SEQUENCE: 21

His Phe Val Gln Gln Thr Pro Gln Ser Gln Pro
 1               5                  10


<210> SEQ ID NO 22
<211> LENGTH: 11
<212> TYPE: PRT
<213> ORGANISM: Neisseria meningitidis

<400> SEQUENCE: 22

Gln Pro Gln Val Thr Asn Gly Val Gln Gly Asn
 1               5                  10
```

<210> SEQ ID NO 23
<211> LENGTH: 7
<212> TYPE: PRT
<213> ORGANISM: Neisseria meningitidis

<400> SEQUENCE: 23

Pro Pro Ser Lys Ser Gln Pro
 1               5

<210> SEQ ID NO 24
<211> LENGTH: 13
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 24

Xaa Gly Gly Tyr Tyr Thr Lys Asp Thr Asn Asn Asn Leu
 1               5                   10

<210> SEQ ID NO 25
<211> LENGTH: 13
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 25

Xaa Gly Gly Ala Gln Ala Ala Asn Gly Gly Ala Ser Gly
 1               5                   10

<210> SEQ ID NO 26
<211> LENGTH: 19
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 26

Xaa Gly Gly Leu Ser Glu Asn Gly Asp Lys Ala Lys Thr Lys Asn Ser
 1               5                   10                  15

Thr Thr Glu

<210> SEQ ID NO 27
<211> LENGTH: 21
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 27

Xaa Gly Gly Asn Ala Phe Glu Leu Phe Leu Ile Gly Ser Ala Thr Ser
 1               5                   10                  15

Asp Glu Ala Lys Gly
            20

-continued

<210> SEQ ID NO 28
<211> LENGTH: 24
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 28

```
Xaa Ala Asn Val Gly Arg Asn Ala Phe Glu Leu Phe Leu Ile Gly Ser
 1               5                  10                  15

Ala Thr Ser Asp Glu Ala Lys Gly
            20
```

<210> SEQ ID NO 29
<211> LENGTH: 17
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 29

```
Xaa Gly Gly Asp Ser Asn Asn Asp Val Ala Ser Gln Leu Gln Ile Phe
 1               5                  10                  15

Lys
```

<210> SEQ ID NO 30
<211> LENGTH: 21
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 30

```
Xaa Ala Asp Leu Asn Thr Asp Ala Glu Arg Val Ala Val Asn Thr Ala
 1               5                  10                  15

Asn Ala His Pro Val
            20
```

<210> SEQ ID NO 31
<211> LENGTH: 14
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 31

```
Xaa Gly Gly Gly Lys Lys Gly Glu Asn Thr Ser Tyr Asp Gln
 1               5                  10
```

<210> SEQ ID NO 32
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid -continued

<400> SEQUENCE: 32

Xaa Gly Gly Glu Arg Gly Lys Lys Gly Glu Asn Thr Ser Tyr Asp Gln
 1               5                   10                  15

<210> SEQ ID NO 33
<211> LENGTH: 22
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 33

Xaa Gly Gly Val Lys Asp Ala Gly Thr Tyr Lys Ala Gln Gly Gly Lys
 1               5                   10                  15

Ser Lys Thr Ala Thr Gln
            20

<210> SEQ ID NO 34
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 34

Xaa Gly Gly Trp Ser Val Ala Glu Gly Gly Ala Ser Gln Val Gly Asn
 1               5                   10                  15

<210> SEQ ID NO 35
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 35

Xaa Lys Arg Asn Thr Gly Ile Gly Asn Tyr Thr Gln Ile Asn Ala Ala
 1               5                   10                  15

<210> SEQ ID NO 36
<211> LENGTH: 22
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 36

Xaa Gly Gly Asn Ile Gln Ala Gln Leu Thr Glu Gln Pro Gln Val Thr
 1               5                   10                  15

Asn Gly Val Gln Gly Asn
            20

<210> SEQ ID NO 37
<211> LENGTH: 15
<212> TYPE: DNA
<213> ORGANISM: Artificial Sequence
<220> FEATURE:
<223> OTHER INFORMATION: linker insertion -continued

<400> SEQUENCE: 37
atgatcgatg gattc 15

<210> SEQ ID NO 38
<211> LENGTH: 21
<212> TYPE: DNA
<213> ORGANISM: Artificial Sequence
<220> FEATURE:
<223> OTHER INFORMATION: linker insertion

<400> SEQUENCE: 38
gatatcatcg atggattcat c 21

<210> SEQ ID NO 39
<211> LENGTH: 18
<212> TYPE: PRT
<213> ORGANISM: Neisseria meningitidis

<400> SEQUENCE: 39

Tyr Tyr Thr Lys Asp Thr Asn Asn Asn Leu Thr Leu Val Pro Ala Gly
1 5 10 15

Ala Cys

<210> SEQ ID NO 40
<211> LENGTH: 17
<212> TYPE: PRT
<213> ORGANISM: Neisseria meningitidis

<400> SEQUENCE: 40

Ala Gln Ala Ala Asn Gly Gly Ala Ser Gly Gln Val Lys Ala Gly Ala
1 5 10 15

Cys

<210> SEQ ID NO 41
<211> LENGTH: 19
<212> TYPE: PRT
<213> ORGANISM: Neisseria meningitidis

<400> SEQUENCE: 41

Asn Ile Gln Ala Gln Leu Thr Glu Gln Pro Gln Val Thr Asn Gly Val
1 5 10 15

Gln Gly Asn

<210> SEQ ID NO 42
<211> LENGTH: 13
<212> TYPE: PRT
<213> ORGANISM: Neisseria meningitidis

<400> SEQUENCE: 42

Thr Lys Ile Ser Asp Phe Gly Ser Phe Ile Gly Phe Lys
1 5 10

<210> SEQ ID NO 43
<211> LENGTH: 15
<212> TYPE: PRT
<213> ORGANISM: Neisseria meningitidis

<400> SEQUENCE: 43

Gly Phe Lys Gly Ser Glu Asp Leu Gly Glu Gly Leu Lys Ala Val
1 5 10 15

-continued

<210> SEQ ID NO 44
<211> LENGTH: 13
<212> TYPE: PRT
<213> ORGANISM: Neisseria meningitidis

<400> SEQUENCE: 44

Val Ser Val Ala Gly Gly Gly Ala Ser Gln Trp Gly Asn
1 5 10

<210> SEQ ID NO 45
<211> LENGTH: 19
<212> TYPE: PRT
<213> ORGANISM: Neisseria meningitidis

<400> SEQUENCE: 45

Thr Leu Arg Ala Gly Arg Val Ala Asn Gln Phe Asp Asp Ala Ser Gln
1 5 10 15

Ala Ile Asn

<210> SEQ ID NO 46
<211> LENGTH: 14
<212> TYPE: PRT
<213> ORGANISM: Neisseria meningitidis

<400> SEQUENCE: 46

Asp Ser Asn Asn Asp Val Ala Ser Gln Leu Gly Ile Phe Lys
1 5 10

<210> SEQ ID NO 47
<211> LENGTH: 8
<212> TYPE: PRT
<213> ORGANISM: Neisseria meningitidis

<400> SEQUENCE: 47

Gly Gly Phe Ser Gly Phe Ser Gly
1 5

<210> SEQ ID NO 48
<211> LENGTH: 13
<212> TYPE: PRT
<213> ORGANISM: Neisseria meningitidis

<400> SEQUENCE: 48

Ala Val Val Gly Lys Pro Gly Ser Asp Val Tyr Tyr Ala
1 5 10

<210> SEQ ID NO 49
<211> LENGTH: 14
<212> TYPE: PRT
<213> ORGANISM: Neisseria meningitidis

<400> SEQUENCE: 49

Tyr Ala Phe Lys Tyr Ala Arg Asn Ala His Val Gly Arg Asn
1 5 10

<210> SEQ ID NO 50
<211> LENGTH: 23
<212> TYPE: PRT
<213> ORGANISM: Neisseria meningitidis -continued

<400> SEQUENCE: 50

```
Ala Asn Val Gly Arg Asn Ala Phe Glu Leu Phe Leu Ile Gly Ser Ala
 1               5                   10                  15

Thr Ser Asp Glu Ala Lys Gly
            20
```

<210> SEQ ID NO 51
<211> LENGTH: 21
<212> TYPE: PRT
<213> ORGANISM: Neisseria meningitidis

<400> SEQUENCE: 51

```
Asp Glu Ala Lys Gly Thr Asp Pro Leu Lys Asn His Gln Val His Arg
 1               5                   10                  15

Leu Thr Gly Gly Tyr
            20
```

<210> SEQ ID NO 52
<211> LENGTH: 16
<212> TYPE: PRT
<213> ORGANISM: Neisseria meningitidis

<400> SEQUENCE: 52

```
Leu Ser Glu Asn Gly Asp Lys Ala Lys Thr Lys Asn Ser Thr Thr Glu
 1               5                   10                  15
```

<210> SEQ ID NO 53
<211> LENGTH: 19
<212> TYPE: PRT
<213> ORGANISM: Neisseria meningitidis

<400> SEQUENCE: 53

```
Val Pro Arg Ile Ser Tyr Ala His Gly Phe Asp Leu Ile Glu Arg Gly
 1               5                   10                  15

Lys Lys Gly
```

<210> SEQ ID NO 54
<211> LENGTH: 13
<212> TYPE: PRT
<213> ORGANISM: Neisseria meningitidis

<400> SEQUENCE: 54

```
Glu Arg Gly Lys Lys Gly Glu Asn Thr Ser Tyr Asp Gln
 1               5                   10
```

<210> SEQ ID NO 55
<211> LENGTH: 15
<212> TYPE: PRT
<213> ORGANISM: Neisseria meningitidis

<400> SEQUENCE: 55

```
Lys Arg Asn Thr Gly Ile Gly Asn Tyr Thr Gln Ile Asn Ala Ala
 1               5                   10                  15
```

<210> SEQ ID NO 56
<211> LENGTH: 12
<212> TYPE: PRT
<213> ORGANISM: Artificial Sequence
<220> FEATURE:
<223> OTHER INFORMATION: Synthetic peptide -continued

<400> SEQUENCE: 56

Gly Gly Tyr Tyr Thr Lys Asp Thr Asn Asn Asn Leu
1 5 10

<210> SEQ ID NO 57
<211> LENGTH: 373
<212> TYPE: PRT
<213> ORGANISM: Neisseria meningitidis

<400> SEQUENCE: 57

Asp Val Ser Leu Tyr Gly Glu Ile Lys Ala Gly Val Glu Gly Arg Asn
1 5 10 15

Ile Gln Ala Gln Leu Thr Glu Gln Pro Gln Val Thr Asn Gly Val Gln
20 25 30

Gly Asn Gln Val Lys Val Thr Lys Ala Lys Ser Arg Ile Arg Thr Lys
35 40 45

Ile Ser Asp Phe Gly Ser Thr Ile Gly Phe Lys Gly Ser Glu Asp Leu
50 55 60

Gly Glu Gly Leu Lys Ala Val Trp Gln Leu Glu Gln Asp Val Ser Val
65 70 75 80

Ala Gly Gly Gly Ala Ser Gln Trp Gly Asn Arg Glu Ser Phe Ile Gly
85 90 95

Leu Ala Gly Glu Phe Gly Thr Leu Arg Ala Gly Arg Val Ala Asn Gln
100 105 110

Phe Asp Asp Ala Ser Gln Ala Ile Asn Pro Trp Asp Ser Asn Asn Asp
115 120 125

Val Ala Ser Gln Leu Gln Ile Phe Lys Arg His Asp Asp Met Pro Val
130 135 140

Ser Val Arg Tyr Asp Ser Pro Glu Phe Ser Gly Phe Ser Gly Ser Val
145 150 155 160

Gln Phe Val Pro Ala Gln Asn Ser Lys Ser Ala Tyr Lys Pro Ala Tyr
165 170 175

Tyr Thr Lys Asp Thr Asn Asn Asn Leu Thr Leu Val Pro Ala Val Val
180 185 190

Gly Lys Pro Gly Ser Asp Val Tyr Tyr Ala Gly Leu Asn Tyr Lys Asn
195 200 205

Gly Gly Phe Ala Gly Asn Tyr Ala Phe Lys Tyr Ala Arg His Ala Asn
210 215 220

Val Gly Arg Asn Ala Phe Glu Leu Phe Leu Ile Gly Ser Ala Thr Ser
225 230 235 240

Asp Glu Ala Lys Gly Thr Asp Pro Leu Lys His Gln Val His Arg Leu
245 250 255

Thr Gly Gly Tyr Glu Glu Gly Gly Leu Asn Leu Ala Leu Ala Ala Gln
260 265 270

Leu Asp Leu Ser Glu Asn Gly Asp Lys Ala Lys Thr Lys Asn Ser Thr
275 280 285

Thr Glu Ile Ala Ala Thr Ala Ser Tyr Arg Phe Gly Asn Ala Val Pro
290 295 300

Arg Ile Ser Tyr Ala His Gly Phe Asp Leu Ile Glu Arg Gly Lys Lys
305 310 315 320

Gly Glu Asn Thr Ser Tyr Asp Gln Ile Ile Ala Gly Val Asp Tyr Asp
325 330 335

Phe Ser Lys Arg Thr Ser Ala Ile Val Ser Gly Ala Trp Leu Lys Arg
340 345 350

-continued

```
Asn Thr Gly Ile Gly Asn Tyr Thr Gln Ile Asn Ala Ala Ser Val Gly
        355                 360                 365

Leu Arg His Lys Phe
    370


<210> SEQ ID NO 58
<211> LENGTH: 328
<212> TYPE: PRT
<213> ORGANISM: Neisseria meningitidis

<400> SEQUENCE: 58

Asp Val Thr Leu Tyr Gly Ala Ile Lys Ala Gly Val Gln Thr Tyr Arg
 1               5                  10                  15

Ser Val Glu His Thr Asp Gly Lys Val Ser Lys Val Glu Thr Gly Ser
            20                  25                  30

Glu Ile Ala Asp Phe Gly Ser Lys Ile Gly Phe Lys Gly Gln Glu Asp
        35                  40                  45

Leu Gly Asn Gly Leu Lys Ala Val Trp Gln Leu Glu Gln Gly Ala Ser
    50                  55                  60

Val Ala Gly Thr Asn Thr Gly Trp Gly Asn Lys Gln Ser Phe Val Gly
65                  70                  75                  80

Leu Lys Gly Gly Phe Gly Thr Ile Arg Ala Gly Ser Leu Asn Ser Pro
                85                  90                  95

Leu Lys Asn Thr Gly Ala Asn Val Asn Ala Trp Glu Ser Gly Lys Phe
            100                 105                 110

Thr Gly Asn Val Leu Glu Ile Ser Gly Met Ala Gln Arg Glu His Arg
        115                 120                 125

Tyr Leu Ser Val Arg Tyr Asp Ser Pro Glu Phe Ala Gly Phe Ser Gly
    130                 135                 140

Ser Val Gln Tyr Ala Pro Lys Asp Asn Ser Gly Ser Asn Gly Glu Ser
145                 150                 155                 160

Tyr His Val Gly Leu Asn Tyr Gln Asn Ser Gly Phe Phe Ala Gln Tyr
                165                 170                 175

Ala Gly Leu Phe Gln Arg Tyr Gly Glu Gly Thr Lys Lys Ile Glu Asp
            180                 185                 190

Asp Gln Thr Tyr Ser Ile Pro Ser Leu Phe Val Glu Lys Leu Gln Val
        195                 200                 205

His Arg Leu Val Gly Gly Tyr Asp Asn Asn Ala Leu Tyr Val Ser Val
    210                 215                 220

Ala Ala Gln Gln Gln Asp Ala Lys Leu Tyr Gly Ala Met Ser Gly Asn
225                 230                 235                 240

Ser His Asn Ser Gln Thr Glu Val Ala Ala Thr Ala Ala Tyr Arg Phe
                245                 250                 255

Gly Asn Val Thr Pro Arg Val Ser Tyr Ala His Gly Phe Lys Gly Thr
            260                 265                 270

Val Asp Ser Ala Asn His Asp Asn Thr Tyr Asp Gln Val Val Val Gly
        275                 280                 285

Ala Glu Tyr Asp Phe Ser Lys Arg Thr Ser Ala Leu Val Ser Ala Gly
    290                 295                 300

Trp Leu Gln Gly Gly Lys Gly Ala Asp Lys Ile Val Ser Thr Ala Ser
305                 310                 315                 320

Ala Val Val Leu Arg His Lys Phe
                325
```

-continued

<210> SEQ ID NO 59
<211> LENGTH: 326
<212> TYPE: PRT
<213> ORGANISM: Neisseria meningitidis

<400> SEQUENCE: 59

```
Asp Val Thr Leu Tyr Gly Thr Ile Lys Ala Gly Val Glu Gly Arg Asn
 1               5                  10                  15

Ile Gln Ala Gln Leu Thr Glu Gln Pro Glu Thr Ser Arg Ser Val Ala
            20                  25                  30

His His Gly Ala Gln Ala Asp Arg Val Lys Thr Ala Thr Glu Ile Ala
        35                  40                  45

Asp Leu Gly Ser Lys Ile Gly Phe Lys Gly Gln Glu Asp Leu Gly Asn
    50                  55                  60

Gly Leu Lys Ala Ile Trp Gln Leu Glu Gln Lys Ala Tyr Val Ser Gly
65                  70                  75                  80

Thr Asp Thr Gly Trp Gly Asn Arg Gln Ser Phe Ile Gly Leu Lys Gly
                85                  90                  95

Gly Phe Gly Lys Val Arg Val Gly Arg Leu Asn Ser Tyr Leu Lys Asp
            100                 105                 110

Thr Gly Gly Phe Asn Pro Trp Glu Gly Lys Ser Tyr Tyr Leu Pro Leu
        115                 120                 125

Ser Asn Ile Ala Gln Pro Glu Glu Arg His Val Ser Val Arg Tyr Asp
    130                 135                 140

Ser Pro Glu Phe Ala Gly Phe Arg Ala Val Gln Tyr Val Pro Asn Asp
145                 150                 155                 160

Asn Ser Gly Lys Asn His Ser Glu Ser Tyr His Ala Gly Phe Asn Tyr
                165                 170                 175

Lys Asn Ser Gly Phe Phe Val Gln Tyr Ala Gly Phe Tyr Lys Arg His
            180                 185                 190

Ser Tyr Thr Thr Glu Lys His Phe Glu Leu Phe Leu Leu Gln Val His
        195                 200                 205

Arg Leu Val Gly Gly Tyr Asp His Asp Ala Leu Tyr Ala Ser Val Ala
    210                 215                 220

Val Gln Gln Gln Asp Ala Lys Leu Thr Trp Arg Asn Asp Asn Ser His
225                 230                 235                 240

Asn Ser Gln Thr Glu Val Ala Ala Thr Ala Ala Tyr Arg Phe Gly Asn
                245                 250                 255

Val Thr Pro Arg Val Ser Tyr Ala His Gly Phe Lys Gly Ser Val Tyr
            260                 265                 270

Asp Ala Asp Asn Asp Asn Thr Tyr Asp Gln Val Val Val Gly Ala Glu
        275                 280                 285

Tyr Asp Phe Ser Lys Arg Thr Ser Ala Leu Val Ser Ala Gly Trp Leu
    290                 295                 300

Gln Arg Gly Lys Gly Thr Glu Lys Phe Val Ala Thr Val Gly Gly Val
305                 310                 315                 320

Gly Leu Arg His Lys Phe
                325
```

<210> SEQ ID NO 60
<211> LENGTH: 353
<212> TYPE: PRT
<213> ORGANISM: Neisseria meningitidis -continued

<400> SEQUENCE: 60

```
Asp Val Thr Leu Tyr Gly Thr Ile Lys Ala Gly Val Glu Gly Arg Asn
 1               5                  10                  15

Ile Gln Ala Gln Leu Thr Glu Gln Pro Glu Val Ser Arg Val Lys Asp
            20                  25                  30

Ala Gly Thr Tyr Lys Ala Gln Gly Gly Lys Ser Lys Thr Ala Thr Gln
        35                  40                  45

Ile Ala Asp Phe Gly Ser Lys Ile Gly Phe Lys Gly Gln Glu Asp Leu
    50                  55                  60

Gly Asn Gly Leu Lys Ala Ile Trp Gln Leu Glu Gln Lys Ala Ser Ile
65                  70                  75                  80

Ala Gly Thr Asn Ser Gly Trp Gly Asn Arg Gln Ser Phe Ile Gly Leu
                85                  90                  95

Lys Gly Gly Phe Gly Thr Val Arg Ala Gly Asn Leu Asn Thr Val Leu
            100                 105                 110

Lys Asp Ser Gly Asp Asn Val Asn Ala Trp Glu Ser Gly Ser Asn Thr
        115                 120                 125

Glu Asp Val Leu Gly Leu Gly Thr Ile Gly Arg Val Glu Ser Arg Glu
    130                 135                 140

Ile Ser Val Arg Tyr Asp Ser Pro Val Phe Ala Gly Phe Ser Gly Ser
145                 150                 155                 160

Val Gln Tyr Val Pro Arg Asp Asn Ala Asn Asp Val Asp Lys Tyr Lys
                165                 170                 175

His Thr Lys Ser Ser Arg Glu Ser Tyr His Ala Gly Leu Lys Tyr Glu
            180                 185                 190

Asn Ala Gly Phe Phe Gly Gln Tyr Ala Gly Ser Phe Ala Lys Tyr Ala
        195                 200                 205

Asp Leu Asn Thr Asp Ala Glu Arg Val Ala Val Asn Thr Ala Asn Ala
    210                 215                 220

His Pro Val Lys Asp Tyr Gln Val His Arg Val Val Ala Gly Tyr Asp
225                 230                 235                 240

Ala Asn Asp Leu Tyr Val Ser Val Ala Gly Gln Tyr Glu Ala Ala Lys
                245                 250                 255

Asn Asn Glu Val Gly Ser Thr Lys Gly Lys Lys His Gln Thr Gln Val
            260                 265                 270

Ala Ala Thr Ala Ala Tyr Arg Phe Gly Asn Val Thr Pro Arg Val Ser
        275                 280                 285

Tyr Ala His Gly Phe Lys Ala Lys Val Asn Gly Val Lys Asp Ala Asn
    290                 295                 300

Tyr Gln Gln Asp Gln Val Ile Val Gly Ala Asp Tyr Asp Phe Ser Lys
305                 310                 315                 320

Arg Thr Ser Ala Leu Val Ser Ala Gly Trp Leu Lys Gln Gly Lys Gly
                325                 330                 335

Thr Gly Lys Val Glu Gln Thr Ala Ser Met Val Gly Leu Arg His Lys
            340                 345                 350

Phe
```

<210> SEQ ID NO 61
<211> LENGTH: 38
<212> TYPE: PRT
<213> ORGANISM: Neisseria meningitidis -continued

<400> SEQUENCE: 61

```
Gly Arg Asn Tyr Gln Leu Gln Leu Thr Glu Ala Gln Ala Ala Asn Gly
 1               5                  10                  15

Gly Ala Gly Gln Val Lys Val Thr Lys Val Thr Lys Ala Lys Ser Arg
            20                  25                  30

Ile Arg Thr Lys Ile Ser
        35
```

<210> SEQ ID NO 62
<211> LENGTH: 116
<212> TYPE: DNA
<213> ORGANISM: Neisseria meningitidis

<400> SEQUENCE: 62

```
ggcaggaact accagctgca attgactgaa gcacaagccg ctaacggtgg agcgagggtc      60

aggtaaaagt tactaaagtt actaaggcca aaagccgcat caggacgaaa atcagt         116
```

<210> SEQ ID NO 63
<211> LENGTH: 36
<212> TYPE: PRT
<213> ORGANISM: Neisseria meningitidis

<400> SEQUENCE: 63

```
Ala Gln Leu Thr Glu Gln Pro Gln Ala Thr Asn Gly Val Gln Gly Gly
 1               5                  10                  15

Arg Gln Gly Asn Gln Val Thr Val Thr Lys Val Lys Ser Arg Ile Arg
            20                  25                  30

Thr Glu Ile Ser
        35
```

<210> SEQ ID NO 64
<211> LENGTH: 122
<212> TYPE: DNA
<213> ORGANISM: Neisseria meningitidis

<400> SEQUENCE: 64

```
ggc agg aac atc tag gcg caa ttg acc gag cag ccc caa gca act aac       48

ggt gtg caa ggg gtc ggc aag gca atc agg taa cag tta cta agg tca       96

aaa gcc gca tca gga cgg aaa tca gc                                   122
```

<210> SEQ ID NO 65
<211> LENGTH: 33
<212> TYPE: PRT
<213> ORGANISM: Neisseria meningitidis

<400> SEQUENCE: 65

```
Gly Arg Asn Phe Gln Leu Gln Leu Thr Glu Pro Pro Ser Lys Ser Gln
 1               5                  10                  15

Pro Gln Val Lys Val Thr Lys Ala Lys Ser Arg Ile Arg Thr Lys Ile
            20                  25                  30

Ser
```

<210> SEQ ID NO 66
<211> LENGTH: 99
<212> TYPE: DNA
<213> ORGANISM: Neisseria meningitidis
<220> FEATURE:
<221> NAME/KEY: CDS
<222> LOCATION: (1)...(99)

-continued

<400> SEQUENCE: 66

```
ggc agg aac ttc cag ctg cag ttg acc gaa ccg ccc tca aag agt caa       48
Gly Arg Asn Phe Gln Leu Gln Leu Thr Glu Pro Pro Ser Lys Ser Gln
 1               5                  10                  15

cct cag gta aaa gtt act aag gcc aaa agc cgc atc agg acg aaa atc       96
Pro Gln Val Lys Val Thr Lys Ala Lys Ser Arg Ile Arg Thr Lys Ile
             20                  25                  30

agt                                                                   99
Ser
```

<210> SEQ ID NO 67
<211> LENGTH: 33
<212> TYPE: PRT
<213> ORGANISM: Neisseria meningitidis

<400> SEQUENCE: 67

```
Gly Asn Asn Ile Gln Leu Gln Leu Thr Glu Pro Pro Ser Lys Gly Gln
 1               5                  10                  15

Thr Gly Asn Lys Val Thr Lys Ala Lys Ser Arg Ile Arg Thr Lys Ile
             20                  25                  30

Ser
```

<210> SEQ ID NO 68
<211> LENGTH: 99
<212> TYPE: DNA
<213> ORGANISM: Neisseria meningitidis
<220> FEATURE:
<221> NAME/KEY: CDS
<222> LOCATION: (1)...(99)

<400> SEQUENCE: 68

```
ggc aac aac att cag ctg caa ttg acc gaa cca ccc tca aaa ggt cag       48
Gly Asn Asn Ile Gln Leu Gln Leu Thr Glu Pro Pro Ser Lys Gly Gln
 1               5                  10                  15

acg ggc aat aaa gtt act aag gcc aaa agc cgc atc agg acg aaa atc       96
Thr Gly Asn Lys Val Thr Lys Ala Lys Ser Arg Ile Arg Thr Lys Ile
             20                  25                  30

agt                                                                   99
Ser
```

<210> SEQ ID NO 69
<211> LENGTH: 36
<212> TYPE: PRT
<213> ORGANISM: Neisseria meningitidis

<400> SEQUENCE: 69

```
Gly Arg Asn Tyr Gln Leu Gln Leu Thr Glu Gln Pro Ser Arg Thr Gln
 1               5                  10                  15

Gly Gln Thr Asn Gln Val Lys Val Thr Lys Ala Lys Ser Arg Ile Arg
             20                  25                  30

Thr Lys Ile Ser
        35
```

<210> SEQ ID NO 70
<211> LENGTH: 110
<212> TYPE: DNA
<213> ORGANISM: Neisseria meningitidis

<400> SEQUENCE: 70

```
ggcaggaact accagctgca attgactgaa caaccctcaa gaactcaagg tcaaacgaga     60

atcaggtaaa agttactaag gccaaaagcc gcatcaggac gaaaatcagt               110
```

-continued

<210> SEQ ID NO 71
<211> LENGTH: 31
<212> TYPE: PRT
<213> ORGANISM: Neisseria meningitidis

<400> SEQUENCE: 71

```
Gly Arg Asn Ile Gln Leu Gln Leu Thr Glu Pro Leu Pro Asn Ile Gln
 1               5                  10                  15

Pro Gln Val Thr Lys Arg Lys Ser Arg Ile Arg Thr Lys Ile Ser
            20                  25                  30
```

<210> SEQ ID NO 72
<211> LENGTH: 93
<212> TYPE: DNA
<213> ORGANISM: Neisseria meningitidis
<220> FEATURE:
<221> NAME/KEY: CDS
<222> LOCATION: (1)...(93)

<400> SEQUENCE: 72

```
ggc agg aac atc cag ctg cag ttg acc gaa ccg ctc cca aat att caa       48
Gly Arg Asn Ile Gln Leu Gln Leu Thr Glu Pro Leu Pro Asn Ile Gln
 1               5                  10                  15

cct cag gtt act aag cgc aaa agc cgc atc agg acg aaa atc agc           93
Pro Gln Val Thr Lys Arg Lys Ser Arg Ile Arg Thr Lys Ile Ser
            20                  25                  30
```

<210> SEQ ID NO 73
<211> LENGTH: 31
<212> TYPE: PRT
<213> ORGANISM: Neisseria meningitidis

<400> SEQUENCE: 73

```
Gly Arg Asn Ile Gln Leu Gln Leu Thr Glu Pro Leu Pro Asn Ile Gln
 1               5                  10                  15

Pro Gln Val Thr Lys Arg Lys Ser Arg Ile Arg Thr Lys Ile Ser
            20                  25                  30
```

<210> SEQ ID NO 74
<211> LENGTH: 93
<212> TYPE: DNA
<213> ORGANISM: Neisseria meningitidis
<220> FEATURE:
<221> NAME/KEY: CDS
<222> LOCATION: (1)...(93)

<400> SEQUENCE: 74

```
ggc agg aac atc cag ctg cag ttg acc gaa ccg ctc cca aat att caa       48
Gly Arg Asn Ile Gln Leu Gln Leu Thr Glu Pro Leu Pro Asn Ile Gln
 1               5                  10                  15

cct cag gtt act aag cgc aaa agc cgc atc agg acg aaa atc agc           93
Pro Gln Val Thr Lys Arg Lys Ser Arg Ile Arg Thr Lys Ile Ser
            20                  25                  30
```

<210> SEQ ID NO 75
<211> LENGTH: 131
<212> TYPE: PRT
<213> ORGANISM: Neisseria meningitidis

<400> SEQUENCE: 75

```
Thr Leu Arg Ala Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30
```

-continued

```
Ile Phe Lys Arg His Asp Asp Met Pro Val Ser Val Arg Tyr Asp Ser
        35                  40                  45

Pro Glu Phe Ser Gly Phe Ser Gly Ser Val Gln Phe Val Pro Ile Gln
    50                  55                  60

Asn Ser Lys Ser Ala Tyr Thr Pro Ala Tyr Tyr Thr Lys Asp Thr Asn
65                  70                  75                  80

Asn Asn Leu Thr Leu Val Pro Ala Val Val Gly Lys Pro Gly Ser Asp
                85                  90                  95

Val Tyr Tyr Ala Gly Leu Asn Tyr Lys Asn Gly Gly Phe Ala Gly Asn
            100                 105                 110

Tyr Ala Phe Lys Tyr Ala Arg His Ala Asn Val Gly Arg Asn Ala Phe
        115                 120                 125

Glu Leu Phe
    130


<210> SEQ ID NO 76
<211> LENGTH: 393
<212> TYPE: DNA
<213> ORGANISM: Neisseria meningitidis
<220> FEATURE:
<221> NAME/KEY: CDS
<222> LOCATION: (1)...(393)

<400> SEQUENCE: 76

acg ctg cgc gcc ggt cgc gtt gcg aat cag ttt gac gat gcc agc caa       48
Thr Leu Arg Ala Gly Arg Val Ala Asn Gln Phe Asp Asp Ala Ser Gln
 1               5                  10                  15

gcc att gat cct tgg gac agc aat aat gat gtg gct tcg caa ttg ggt       96
Ala Ile Asp Pro Trp Asp Ser Asn Asn Asp Val Ala Ser Gln Leu Gly
            20                  25                  30

att ttc aaa cgc cac gac gac atg ccg gtt tct gta cgc tac gat tcc      144
Ile Phe Lys Arg His Asp Asp Met Pro Val Ser Val Arg Tyr Asp Ser
        35                  40                  45

ccc gaa ttt tcc ggt ttc agc ggc agc gtt caa ttc gtt ccg atc caa      192
Pro Glu Phe Ser Gly Phe Ser Gly Ser Val Gln Phe Val Pro Ile Gln
    50                  55                  60

aac agc aag tcc gcc tat acg ccg gct tat tat act aag gat aca aac      240
Asn Ser Lys Ser Ala Tyr Thr Pro Ala Tyr Tyr Thr Lys Asp Thr Asn
 65                  70                  75                  80

aat aat ctt act ctc gtt ccg gct gtt gtc ggc aag ccc gga tcg gat      288
Asn Asn Leu Thr Leu Val Pro Ala Val Val Gly Lys Pro Gly Ser Asp
                85                  90                  95

gtg tat tat gcc ggt ctg aat tac aaa aat ggc ggt ttt gcc ggg aac      336
Val Tyr Tyr Ala Gly Leu Asn Tyr Lys Asn Gly Gly Phe Ala Gly Asn
            100                 105                 110

tat gcc ttt aaa tat gcg aga cac gcc aat gtc gga cgt aat gct ttt      384
Tyr Ala Phe Lys Tyr Ala Arg His Ala Asn Val Gly Arg Asn Ala Phe
        115                 120                 125

gag ttg ttc                                                           393
Glu Leu Phe
    130


<210> SEQ ID NO 77
<211> LENGTH: 130
<212> TYPE: PRT
<213> ORGANISM: Neisseria meningitidis
```

-continued

<400> SEQUENCE: 77

```
Thr Leu Arg Thr Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30

Ile Phe Lys Arg His Asp Asp Met Pro Val Ser Val Arg Tyr Asp Ser
        35                  40                  45

Pro Asp Phe Ser Gly Phe Ser Gly Ser Val Gln Phe Val Pro Ala Gln
    50                  55                  60

Asn Ser Lys Ser Ala Tyr Thr Pro Ala Tyr Val Ala Val Glu Asn Gly
65                  70                  75                  80

Val Ala Lys Lys Val Ala Ala Val Val Gly Lys Pro Gly Ser Asp Val
                85                  90                  95

Tyr Tyr Ala Gly Leu Asn Tyr Lys Asn Gly Gly Phe Ala Gly Asn Tyr
            100                 105                 110

Ala Phe Lys Tyr Ala Lys His Ala Asn Val Gly Arg Asp Ala Phe Glu
        115                 120                 125

Leu Phe
    130
```

<210> SEQ ID NO 78
<211> LENGTH: 390
<212> TYPE: DNA
<213> ORGANISM: Neisseria meningitidis
<220> FEATURE:
<221> NAME/KEY: CDS
<222> LOCATION: (1)...(390)

<400> SEQUENCE: 78

```
acg ctg cgc acc ggt cgc gtt gcg aat cag ttt gac gat gcc agc caa       48
Thr Leu Arg Thr Gly Arg Val Ala Asn Gln Phe Asp Asp Ala Ser Gln
 1               5                  10                  15

gcc att gat cct tgg gac agc aat aat gat gtg gct tcg caa ttg ggt       96
Ala Ile Asp Pro Trp Asp Ser Asn Asn Asp Val Ala Ser Gln Leu Gly
            20                  25                  30

att ttc aaa cgc cac gac gat atg ccg gtt tct gta cgc tac gac tct      144
Ile Phe Lys Arg His Asp Asp Met Pro Val Ser Val Arg Tyr Asp Ser
        35                  40                  45

ccg gac ttt tcc ggt ttc agc ggc agc gtc caa ttc gtt ccg gct caa      192
Pro Asp Phe Ser Gly Phe Ser Gly Ser Val Gln Phe Val Pro Ala Gln
    50                  55                  60

aac agc aag tcc gcc tat acg ccg gct tat gtg gcg gtg gaa aat ggc      240
Asn Ser Lys Ser Ala Tyr Thr Pro Ala Tyr Val Ala Val Glu Asn Gly
 65                  70                  75                  80

gta gct aaa aaa gtt gcg gct gtt gtc ggc aag ccc gga tcg gat gtg      288
Val Ala Lys Lys Val Ala Ala Val Val Gly Lys Pro Gly Ser Asp Val
                85                  90                  95

tat tat gcc ggt ctg aat tat aag aat ggc ggt ttt gcc ggg aac tat      336
Tyr Tyr Ala Gly Leu Asn Tyr Lys Asn Gly Gly Phe Ala Gly Asn Tyr
            100                 105                 110

gcc ttt aaa tat gcg aaa cac gcc aat gtc gga cgt gat gct ttt gag      384
Ala Phe Lys Tyr Ala Lys His Ala Asn Val Gly Arg Asp Ala Phe Glu
        115                 120                 125

ttg ttc                                                              390
Leu Phe
    130
```

-continued

```
<210> SEQ ID NO 79
<211> LENGTH: 130
<212> TYPE: PRT
<213> ORGANISM: Neisseria meningitidis
<220> FEATURE:
<221> NAME/KEY: VARIANT
<222> LOCATION: 3
<223> OTHER INFORMATION: Xaa = Leu, Pro, His, Gln or Arg
<220> FEATURE:
<221> NAME/KEY: VARIANT
<222> LOCATION: 4
<223> OTHER INFORMATION: Xaa = Any Amino Acid

<400> SEQUENCE: 79

Thr Leu Xaa Xaa Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30

Ile Phe Lys Arg His Asp Asp Met Pro Val Ser Val Arg Tyr Asp Ser
        35                  40                  45

Pro Asp Phe Ser Gly Phe Ser Gly Ser Val Gln Phe Val Pro Ile Gln
    50                  55                  60

Asn Ser Lys Ser Ala Tyr Thr Pro Ala His Asn Thr Arg Gln Asn Asn
65                  70                  75                  80

Ala Asp Val Phe Val Pro Ala Val Val Gly Lys Pro Gly Ser Asp Val
                85                  90                  95

Tyr Tyr Ala Gly Leu Asn Tyr Lys Asn Gly Gly Phe Ala Gly Arg Tyr
            100                 105                 110

Ala Phe Lys Tyr Ala Arg His Ala Asn Val Gly Arg Asp Ala Phe Glu
        115                 120                 125

Leu Phe
    130


<210> SEQ ID NO 80
<211> LENGTH: 390
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G
<220> FEATURE:
<221> NAME/KEY: CDS
<222> LOCATION: (1)...(390)

<400> SEQUENCE: 80

acg ctg cnn nnn ggt cgc gtc gcg aat cag ttt gac gat gcc agc caa       48
Thr Leu Xaa Xaa Gly Arg Val Ala Asn Gln Phe Asp Asp Ala Ser Gln
 1               5                  10                  15

gcc att gat cct tgg gac agc aac aat gat gtg gct tcg caa ttg ggt       96
Ala Ile Asp Pro Trp Asp Ser Asn Asn Asp Val Ala Ser Gln Leu Gly
            20                  25                  30

att ttc aaa cgc cac gac gat atg ccg gtt tct gta cgc tac gac tct      144
Ile Phe Lys Arg His Asp Asp Met Pro Val Ser Val Arg Tyr Asp Ser
        35                  40                  45

ccg gac ttt tcc ggt ttc agc ggc agc gtc caa ttc gtt ccg atc caa      192
Pro Asp Phe Ser Gly Phe Ser Gly Ser Val Gln Phe Val Pro Ile Gln
    50                  55                  60

aac agc aag tcc gcc tat acg ccg gct cat aat act agg cag aac aat      240
Asn Ser Lys Ser Ala Tyr Thr Pro Ala His Asn Thr Arg Gln Asn Asn
65                  70                  75                  80
```

-continued

```
gct gat gtt ttc gtt ccg gct gtt gtc ggc aag ccc gga tcg gat gtg      288
Ala Asp Val Phe Val Pro Ala Val Val Gly Lys Pro Gly Ser Asp Val
                85                  90                  95

tat tat gcc ggt ctg aat tac aaa aat ggc ggt ttt gcc ggg cgc tat      336
Tyr Tyr Ala Gly Leu Asn Tyr Lys Asn Gly Gly Phe Ala Gly Arg Tyr
            100                 105                 110

gcc ttt aaa tat gcg aga cac gcc aat gtc gga cgt gat gct ttt gag      384
Ala Phe Lys Tyr Ala Arg His Ala Asn Val Gly Arg Asp Ala Phe Glu
        115                 120                 125

ttg ttc                                                              390
Leu Phe
    130


<210> SEQ ID NO 81
<211> LENGTH: 132
<212> TYPE: PRT
<213> ORGANISM: Neisseria meningitidis

<400> SEQUENCE: 81

Thr Leu Arg Thr Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30

Ile Phe Lys Arg His Asp Asp Met Ser Val Ser Val Arg Tyr Asp Ser
        35                  40                  45

Pro Glu Phe Ser Gly Phe Ser Gly Ser Val Gln Phe Val Pro Ala Gln
    50                  55                  60

Asn Ser Lys Ser Ala Tyr Thr Pro Ala His Phe Val Gln Asn Lys Gln
65                  70                  75                  80

Asn Gln Arg Pro Thr Leu Val Pro Ala Val Val Gly Lys Pro Gly Ser
                85                  90                  95

Asp Val Tyr Tyr Ala Gly Leu Asn Tyr Lys Asn Gly Gly Phe Ala Gly
            100                 105                 110

Asn Tyr Ala Phe Lys Tyr Ala Lys His Ala Asn Val Gly Arg Asp Ala
        115                 120                 125

Phe Glu Leu Phe
    130


<210> SEQ ID NO 82
<211> LENGTH: 396
<212> TYPE: DNA
<213> ORGANISM: Neisseria meningitidis
<220> FEATURE:
<221> NAME/KEY: CDS
<222> LOCATION: (1)...(396)

<400> SEQUENCE: 82

acg ctg cgc acc ggt cgc gtt gca aat cag ttt gac gat gcc agc caa       48
Thr Leu Arg Thr Gly Arg Val Ala Asn Gln Phe Asp Asp Ala Ser Gln
 1               5                  10                  15

gcc att gat cct tgg gac agc aat aat gat gtg gct tcg caa ttg ggt       96
Ala Ile Asp Pro Trp Asp Ser Asn Asn Asp Val Ala Ser Gln Leu Gly
            20                  25                  30

att ttc aaa cgc cac gac gat atg tcg gtt tct gta cgc tac gat tcc      144
Ile Phe Lys Arg His Asp Asp Met Ser Val Ser Val Arg Tyr Asp Ser
        35                  40                  45

ccc gaa ttt tcc ggt ttt agc ggc agc gtc caa ttc gtt ccg gcc caa      192
Pro Glu Phe Ser Gly Phe Ser Gly Ser Val Gln Phe Val Pro Ala Gln
    50                  55                  60
```

-continued

```
aac agc aag tcc gcc tat acg ccg gct cat ttt gtt cag aat aag caa      240
Asn Ser Lys Ser Ala Tyr Thr Pro Ala His Phe Val Gln Asn Lys Gln
 65                 70                  75                  80

aat cag cgg cct act ctc gtt ccg gct gtt gtc ggc aag ccg ggg tcg      288
Asn Gln Arg Pro Thr Leu Val Pro Ala Val Val Gly Lys Pro Gly Ser
                85                  90                  95

gat gtg tat tat gcc ggt ctg aat tac aaa aat ggc ggt ttt gcc ggg      336
Asp Val Tyr Tyr Ala Gly Leu Asn Tyr Lys Asn Gly Gly Phe Ala Gly
            100                 105                 110

aac tat gcc ttt aaa tac gcg aaa cac gcc aat gtg ggc cgt gat gct      384
Asn Tyr Ala Phe Lys Tyr Ala Lys His Ala Asn Val Gly Arg Asp Ala
        115                 120                 125

ttt gag ttg ttc                                                      396
Phe Glu Leu Phe
    130
```

<210> SEQ ID NO 83
<211> LENGTH: 132
<212> TYPE: PRT
<213> ORGANISM: Neisseria meningitidis

<400> SEQUENCE: 83

```
Thr Leu Arg Thr Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30

Ile Phe Lys Arg His Asp Asp Met Ser Val Ser Val Arg Tyr Asp Ser
        35                  40                  45

Pro Glu Phe Ser Gly Phe Ser Gly Ser Val Gln Phe Val Pro Ala Gln
    50                  55                  60

Asn Ser Lys Ser Ala Tyr Thr Pro Ala His Phe Val Gln Asn Lys Gln
65                  70                  75                  80

Asn Gln Arg Pro Thr Leu Val Pro Ala Val Val Gly Lys Pro Gly Ser
                85                  90                  95

Asp Val Tyr Tyr Ala Gly Leu Asn Tyr Lys Asn Gly Gly Phe Ala Gly
            100                 105                 110

Asn Tyr Ala Phe Lys Tyr Ala Lys His Ala Asn Val Gly Arg Asp Ala
        115                 120                 125

Phe Glu Leu Phe
    130
```

<210> SEQ ID NO 84
<211> LENGTH: 396
<212> TYPE: DNA
<213> ORGANISM: Neisseria meningitidis
<220> FEATURE:
<221> NAME/KEY: CDS
<222> LOCATION: (1)...(396)

<400> SEQUENCE: 84

```
acg ctg cgc acc ggt cgc gtt gca aat cag ttt gac gat gcc agc caa       48
Thr Leu Arg Thr Gly Arg Val Ala Asn Gln Phe Asp Asp Ala Ser Gln
 1               5                  10                  15

gcc att gat cct tgg gac agc aat aat gat gtg gct tcg caa ttg ggt       96
Ala Ile Asp Pro Trp Asp Ser Asn Asn Asp Val Ala Ser Gln Leu Gly
            20                  25                  30

att ttc aaa cgc cac gac gat atg tcg gtt tct gta cgc tac gat tcc      144
Ile Phe Lys Arg His Asp Asp Met Ser Val Ser Val Arg Tyr Asp Ser
        35                  40                  45
```

-continued

```
ccc gaa ttt tcc ggt ttt agc ggc agc gtc caa ttc gtt ccg gcc caa      192
Pro Glu Phe Ser Gly Phe Ser Gly Ser Val Gln Phe Val Pro Ala Gln
     50                  55                  60

aac agc aag tcc gcc tat acg ccg gct cat ttt gtt cag aat aag caa      240
Asn Ser Lys Ser Ala Tyr Thr Pro Ala His Phe Val Gln Asn Lys Gln
 65                  70                  75                  80

aat cag cgg cct act ctc gtt ccg gct gtt gtc ggc aag ccg ggg tcg      288
Asn Gln Arg Pro Thr Leu Val Pro Ala Val Val Gly Lys Pro Gly Ser
                 85                  90                  95

gat gtg tat tat gcc ggt ctg aat tac aaa aat ggc ggt ttt gcc ggg      336
Asp Val Tyr Tyr Ala Gly Leu Asn Tyr Lys Asn Gly Gly Phe Ala Gly
            100                 105                 110

aac tat gcc ttt aaa tac gcg aaa cac gcc aat gtg ggc cgt gat gct      384
Asn Tyr Ala Phe Lys Tyr Ala Lys His Ala Asn Val Gly Arg Asp Ala
        115                 120                 125

ttt gag ttg ttc                                                      396
Phe Glu Leu Phe
    130
```

<210> SEQ ID NO 85
<211> LENGTH: 87
<212> TYPE: PRT
<213> ORGANISM: Neisseria meningitidis

<400> SEQUENCE: 85

```
Arg Tyr Asp Ser Pro Asp Phe Ser Gly Phe Ser Gly Ser Val Gln Phe
 1               5                  10                  15

Val Pro Ala Gln Asn Ser Lys Ser Ala Tyr Thr Pro Ala Thr Tyr Thr
            20                  25                  30

Val Asp Ser Ser Gly Val Val Thr Pro Val Pro Ala Val Val Gly Lys
        35                  40                  45

Pro Gly Ser Asp Val Tyr Tyr Ala Gly Leu Asn Tyr Lys Asn Gly Gly
    50                  55                  60

Phe Ala Gly Asn Tyr Ala Phe Lys Tyr Ala Lys His Ala Asn Val Gly
65                  70                  75                  80

Arg Asp Ala Phe Asn Leu Phe
                85
```

<210> SEQ ID NO 86
<211> LENGTH: 261
<212> TYPE: DNA
<213> ORGANISM: Neisseria meningitidis
<220> FEATURE:
<221> NAME/KEY: CDS
<222> LOCATION: (1)...(261)

<400> SEQUENCE: 86

```
cgc tac gac tct ccg gac ttt tcc ggt ttc agc ggc agc gtc caa ttc       48
Arg Tyr Asp Ser Pro Asp Phe Ser Gly Phe Ser Gly Ser Val Gln Phe
 1               5                  10                  15

gtt ccg gcc caa aac agc aaa tcc gcc tat acg ccg gct act tat act       96
Val Pro Ala Gln Asn Ser Lys Ser Ala Tyr Thr Pro Ala Thr Tyr Thr
             20                  25                  30

gtg gat agt agt ggt gtt gtt act ccc gtt cct gct gtt gtc ggc aag      144
Val Asp Ser Ser Gly Val Val Thr Pro Val Pro Ala Val Val Gly Lys
         35                  40                  45

ccc gga tcg gat gtg tat tat gcc ggt ctg aat tac aaa aat ggc ggt      192
Pro Gly Ser Asp Val Tyr Tyr Ala Gly Leu Asn Tyr Lys Asn Gly Gly
     50                  55                  60
```

-continued

```
ttt gcc ggg aac tat gcc ttt aaa tac gcg aaa cac gcc aat gtg ggc      240
Phe Ala Gly Asn Tyr Ala Phe Lys Tyr Ala Lys His Ala Asn Val Gly
 65                  70                  75                  80

cgt gat gct ttt aat ttg ttc                                          261
Arg Asp Ala Phe Asn Leu Phe
                 85
```

<210> SEQ ID NO 87
<211> LENGTH: 83
<212> TYPE: PRT
<213> ORGANISM: Neisseria meningitidis

<400> SEQUENCE: 87

```
Arg Tyr Asp Ser Pro Asp Phe Ser Gly Phe Ser Gly Ser Val Gln Phe
 1               5                  10                  15

Val Pro Ala Gln Asn Ser Lys Ser Ala Tyr Lys Pro Ala Tyr Val Asp
            20                  25                  30

Glu Lys Lys Met Val His Ala Ala Val Val Gly Lys Pro Gly Ser Asp
        35                  40                  45

Val Tyr Tyr Ala Gly Leu Asn Tyr Lys Asn Gly Gly Phe Ala Gly Asn
    50                  55                  60

Tyr Ala Phe Lys Tyr Ala Lys His Ala Asn Val Gly Arg Asp Ala Phe
65                  70                  75                  80

Asn Leu Phe
```

<210> SEQ ID NO 88
<211> LENGTH: 249
<212> TYPE: DNA
<213> ORGANISM: Neisseria meningitidis
<220> FEATURE:
<221> NAME/KEY: CDS
<222> LOCATION: (1)...(249)

<400> SEQUENCE: 88

```
cgc tac gac tct ccg gac ttt tcc ggt ttc agc ggc agc gtc caa ttc       48
Arg Tyr Asp Ser Pro Asp Phe Ser Gly Phe Ser Gly Ser Val Gln Phe
 1               5                  10                  15

gtt ccg gct caa aac agc aag tcc gcc tat aag ccg gct tat gtg gat       96
Val Pro Ala Gln Asn Ser Lys Ser Ala Tyr Lys Pro Ala Tyr Val Asp
            20                  25                  30

gag aag aaa atg gtt cat gcg gct gtt gtc ggc aag ccc gga tcg gat      144
Glu Lys Lys Met Val His Ala Ala Val Val Gly Lys Pro Gly Ser Asp
        35                  40                  45

gtg tat tat gcc ggt ctg aat tac aaa aat ggc ggt ttt gcc ggg aac      192
Val Tyr Tyr Ala Gly Leu Asn Tyr Lys Asn Gly Gly Phe Ala Gly Asn
    50                  55                  60

tat gcc ttt aaa tat gcg aaa cac gcc aat gtg ggc cgt gat gct ttt      240
Tyr Ala Phe Lys Tyr Ala Lys His Ala Asn Val Gly Arg Asp Ala Phe
 65                  70                  75                  80

aat ttg ttc                                                          249
Asn Leu Phe
```

<210> SEQ ID NO 89
<211> LENGTH: 10
<212> TYPE: PRT
<213> ORGANISM: Neisseria meningitidis

<400> SEQUENCE: 89

```
Thr Glu Gln Pro Gln Val Thr Asn Gly Val
 1               5                  10
```

-continued

<210> SEQ ID NO 90
<211> LENGTH: 10
<212> TYPE: PRT
<213> ORGANISM: Neisseria meningitidis

<400> SEQUENCE: 90

Glu Gln Pro Gln Val Thr Asn Gly Val Gln
1 5 10

<210> SEQ ID NO 91
<211> LENGTH: 10
<212> TYPE: PRT
<213> ORGANISM: Neisseria meningitidis

<400> SEQUENCE: 91

Gln Pro Gln Val Thr Asn Gly Val Gln Gly
1 5 10

<210> SEQ ID NO 92
<211> LENGTH: 10
<212> TYPE: PRT
<213> ORGANISM: Neisseria meningitidis

<400> SEQUENCE: 92

Pro Gln Val Thr Asn Gly Val Gln Gly Asn
1 5 10

<210> SEQ ID NO 93
<211> LENGTH: 10
<212> TYPE: PRT
<213> ORGANISM: Neisseria meningitidis

<400> SEQUENCE: 93

Gln Val Thr Asn Gly Val Gln Gly Asn Gln
1 5 10

<210> SEQ ID NO 94
<211> LENGTH: 10
<212> TYPE: PRT
<213> ORGANISM: Neisseria meningitidis

<400> SEQUENCE: 94

Val Thr Asn Gly Val Gln Gly Asn Gln Val
1 5 10

<210> SEQ ID NO 95
<211> LENGTH: 10
<212> TYPE: PRT
<213> ORGANISM: Neisseria meningitidis

<400> SEQUENCE: 95

Thr Asn Gly Val Gln Gly Asn Gln Val Lys
1 5 10

<210> SEQ ID NO 96
<211> LENGTH: 10
<212> TYPE: PRT
<213> ORGANISM: Neisseria meningitidis

<400> SEQUENCE: 96

Asn Gly Val Gln Gly Asn Gln Val Lys Val
1 5 10

-continued

<210> SEQ ID NO 97
<211> LENGTH: 10
<212> TYPE: PRT
<213> ORGANISM: Neisseria meningitidis

<400> SEQUENCE: 97

Gly Val Gln Gly Asn Gln Val Lys Val Thr
1 5 10

<210> SEQ ID NO 98
<211> LENGTH: 10
<212> TYPE: PRT
<213> ORGANISM: Neisseria meningitidis

<400> SEQUENCE: 98

Val Gln Gly Asn Gln Val Lys Val Thr Lys
1 5 10

<210> SEQ ID NO 99
<211> LENGTH: 10
<212> TYPE: PRT
<213> ORGANISM: Neisseria meningitidis

<400> SEQUENCE: 99

Gln Gly Asn Gln Val Lys Val Thr Lys Ala
1 5 10

<210> SEQ ID NO 100
<211> LENGTH: 10
<212> TYPE: PRT
<213> ORGANISM: Neisseria meningitidis

<400> SEQUENCE: 100

Gly Asn Gln Val Lys Val Thr Lys Ala Lys
1 5 10

<210> SEQ ID NO 101
<211> LENGTH: 10
<212> TYPE: PRT
<213> ORGANISM: Neisseria meningitidis

<400> SEQUENCE: 101

Asn Gln Val Lys Val Thr Lys Ala Lys Ser
1 5 10

<210> SEQ ID NO 102
<211> LENGTH: 10
<212> TYPE: PRT
<213> ORGANISM: Neisseria meningitidis

<400> SEQUENCE: 102

Tyr Lys Pro Ala Tyr Tyr Thr Lys Asp Thr
1 5 10

<210> SEQ ID NO 103
<211> LENGTH: 10
<212> TYPE: PRT
<213> ORGANISM: Neisseria meningitidis

<400> SEQUENCE: 103

Lys Pro Ala Tyr Tyr Thr Lys Asp Thr Asn
1 5 10

-continued

<210> SEQ ID NO 104
<211> LENGTH: 10
<212> TYPE: PRT
<213> ORGANISM: Neisseria meningitidis

<400> SEQUENCE: 104

Pro Ala Tyr Tyr Thr Lys Asp Thr Asn Asn
1 5 10

<210> SEQ ID NO 105
<211> LENGTH: 10
<212> TYPE: PRT
<213> ORGANISM: Neisseria meningitidis

<400> SEQUENCE: 105

Ala Tyr Tyr Thr Lys Asp Thr Asn Asn Asn
1 5 10

<210> SEQ ID NO 106
<211> LENGTH: 10
<212> TYPE: PRT
<213> ORGANISM: Neisseria meningitidis

<400> SEQUENCE: 106

Tyr Tyr Thr Lys Asp Thr Asn Asn Asn Leu
1 5 10

<210> SEQ ID NO 107
<211> LENGTH: 10
<212> TYPE: PRT
<213> ORGANISM: Neisseria meningitidis

<400> SEQUENCE: 107

Tyr Thr Lys Asp Thr Asn Asn Asn Leu Thr
1 5 10

<210> SEQ ID NO 108
<211> LENGTH: 10
<212> TYPE: PRT
<213> ORGANISM: Neisseria meningitidis

<400> SEQUENCE: 108

Thr Lys Asp Thr Asn Asn Asn Leu Thr Leu
1 5 10

<210> SEQ ID NO 109
<211> LENGTH: 10
<212> TYPE: PRT
<213> ORGANISM: Neisseria meningitidis

<400> SEQUENCE: 109

Lys Asp Thr Asn Asn Asn Leu Thr Leu Val
1 5 10

<210> SEQ ID NO 110
<211> LENGTH: 10
<212> TYPE: PRT
<213> ORGANISM: Neisseria meningitidis

<400> SEQUENCE: 110

Asp Thr Asn Asn Asn Leu Thr Leu Val Pro
1 5 10

-continued

<210> SEQ ID NO 111
<211> LENGTH: 10
<212> TYPE: PRT
<213> ORGANISM: Neisseria meningitidis

<400> SEQUENCE: 111

Thr Asn Asn Asn Leu Thr Leu Val Pro Ala
1 5 10

<210> SEQ ID NO 112
<211> LENGTH: 10
<212> TYPE: PRT
<213> ORGANISM: Neisseria meningitidis

<400> SEQUENCE: 112

Asn Asn Asn Leu Thr Leu Val Pro Ala Val
1 5 10

<210> SEQ ID NO 113
<211> LENGTH: 10
<212> TYPE: PRT
<213> ORGANISM: Neisseria meningitidis

<400> SEQUENCE: 113

Asn Asn Leu Thr Leu Val Pro Ala Val Val
1 5 10

<210> SEQ ID NO 114
<211> LENGTH: 10
<212> TYPE: PRT
<213> ORGANISM: Neisseria meningitidis

<400> SEQUENCE: 114

Asn Leu Thr Leu Val Pro Ala Val Val Gly
1 5 10

<210> SEQ ID NO 115
<211> LENGTH: 10
<212> TYPE: PRT
<213> ORGANISM: Neisseria meningitidis

<400> SEQUENCE: 115

Leu Thr Leu Val Pro Ala Val Val Gly Lys
1 5 10

<210> SEQ ID NO 116
<211> LENGTH: 10
<212> TYPE: PRT
<213> ORGANISM: Neisseria meningitidis

<400> SEQUENCE: 116

Thr Glu Ala Gln Ala Ala Asn Gly Gly Ala
1 5 10

<210> SEQ ID NO 117
<211> LENGTH: 10
<212> TYPE: PRT
<213> ORGANISM: Neisseria meningitidis

<400> SEQUENCE: 117

Glu Ala Gln Ala Ala Asn Gly Gly Ala Ser
1 5 10

-continued

<210> SEQ ID NO 118
<211> LENGTH: 10
<212> TYPE: PRT
<213> ORGANISM: Neisseria meningitidis

<400> SEQUENCE: 118

Ala Gln Ala Ala Asn Gly Gly Ala Ser Gly
1 5 10

<210> SEQ ID NO 119
<211> LENGTH: 10
<212> TYPE: PRT
<213> ORGANISM: Neisseria meningitidis

<400> SEQUENCE: 119

Gln Ala Ala Asn Gly Gly Ala Ser Gly Gln
1 5 10

<210> SEQ ID NO 120
<211> LENGTH: 10
<212> TYPE: PRT
<213> ORGANISM: Neisseria meningitidis

<400> SEQUENCE: 120

Ala Ala Asn Gly Gly Ala Ser Gly Gln Val
1 5 10

<210> SEQ ID NO 121
<211> LENGTH: 10
<212> TYPE: PRT
<213> ORGANISM: Neisseria meningitidis

<400> SEQUENCE: 121

Ala Asn Gly Gly Ala Ser Gly Gln Val Lys
1 5 10

<210> SEQ ID NO 122
<211> LENGTH: 10
<212> TYPE: PRT
<213> ORGANISM: Neisseria meningitidis

<400> SEQUENCE: 122

Asn Gly Gly Ala Ser Gly Gln Val Lys Val
1 5 10

<210> SEQ ID NO 123
<211> LENGTH: 10
<212> TYPE: PRT
<213> ORGANISM: Neisseria meningitidis

<400> SEQUENCE: 123

Gly Gly Ala Ser Gly Gln Val Lys Val Thr
1 5 10

<210> SEQ ID NO 124
<211> LENGTH: 10
<212> TYPE: PRT
<213> ORGANISM: Neisseria meningitidis

<400> SEQUENCE: 124

Gly Ala Ser Gly Gln Val Lys Val Thr Lys
1 5 10

-continued

<210> SEQ ID NO 125
<211> LENGTH: 10
<212> TYPE: PRT
<213> ORGANISM: Neisseria meningitidis

<400> SEQUENCE: 125

Ala Ser Gly Gln Val Lys Val Thr Lys Val
1 5 10

<210> SEQ ID NO 126
<211> LENGTH: 10
<212> TYPE: PRT
<213> ORGANISM: Neisseria meningitidis

<400> SEQUENCE: 126

Ser Gly Gln Val Lys Val Thr Lys Val Thr
1 5 10

<210> SEQ ID NO 127
<211> LENGTH: 10
<212> TYPE: PRT
<213> ORGANISM: Neisseria meningitidis

<400> SEQUENCE: 127

Gly Gln Val Lys Val Thr Lys Val Thr Lys
1 5 10

<210> SEQ ID NO 128
<211> LENGTH: 10
<212> TYPE: PRT
<213> ORGANISM: Neisseria meningitidis

<400> SEQUENCE: 128

Gln Val Lys Val Thr Lys Val Thr Lys Ala
1 5 10

<210> SEQ ID NO 129
<211> LENGTH: 10
<212> TYPE: PRT
<213> ORGANISM: Neisseria meningitidis

<400> SEQUENCE: 129

Val Lys Val Thr Lys Val Thr Lys Ala Lys
1 5 10

<210> SEQ ID NO 130
<211> LENGTH: 10
<212> TYPE: PRT
<213> ORGANISM: Neisseria meningitidis

<400> SEQUENCE: 130

Lys Val Thr Lys Val Thr Lys Ala Lys Ser
1 5 10

<210> SEQ ID NO 131
<211> LENGTH: 10
<212> TYPE: PRT
<213> ORGANISM: Neisseria meningitidis

<400> SEQUENCE: 131

Val Thr Lys Val Thr Lys Ala Lys Ser Arg
1 5 10

-continued

<210> SEQ ID NO 132
<211> LENGTH: 10
<212> TYPE: PRT
<213> ORGANISM: Neisseria meningitidis

<400> SEQUENCE: 132

Thr Lys Val Thr Lys Ala Lys Ser Arg Ile
1 5 10

<210> SEQ ID NO 133
<211> LENGTH: 10
<212> TYPE: PRT
<213> ORGANISM: Neisseria meningitidis

<400> SEQUENCE: 133

Lys Val Thr Lys Ala Lys Ser Arg Ile Arg
1 5 10

<210> SEQ ID NO 134
<211> LENGTH: 10
<212> TYPE: PRT
<213> ORGANISM: Neisseria meningitidis

<400> SEQUENCE: 134

Ser Ala Tyr Thr Pro Ala Tyr Tyr Thr Lys
1 5 10

<210> SEQ ID NO 135
<211> LENGTH: 10
<212> TYPE: PRT
<213> ORGANISM: Neisseria meningitidis

<400> SEQUENCE: 135

Ala Tyr Thr Pro Ala Tyr Tyr Thr Lys Asp
1 5 10

<210> SEQ ID NO 136
<211> LENGTH: 10
<212> TYPE: PRT
<213> ORGANISM: Neisseria meningitidis

<400> SEQUENCE: 136

Tyr Thr Pro Ala Tyr Tyr Thr Lys Asp Thr
1 5 10

<210> SEQ ID NO 137
<211> LENGTH: 10
<212> TYPE: PRT
<213> ORGANISM: Neisseria meningitidis

<400> SEQUENCE: 137

Thr Pro Ala Tyr Tyr Thr Lys Asp Thr Asn
1 5 10

<210> SEQ ID NO 138
<211> LENGTH: 10
<212> TYPE: PRT
<213> ORGANISM: Neisseria meningitidis

<400> SEQUENCE: 138

Pro Ala Tyr Tyr Thr Lys Asp Thr Asn Asn
1 5 10

-continued

<210> SEQ ID NO 139
<211> LENGTH: 10
<212> TYPE: PRT
<213> ORGANISM: Neisseria meningitidis

<400> SEQUENCE: 139

Ala Tyr Tyr Thr Lys Asp Thr Asn Asn Asn
1 5 10

<210> SEQ ID NO 140
<211> LENGTH: 10
<212> TYPE: PRT
<213> ORGANISM: Neisseria meningitidis

<400> SEQUENCE: 140

Tyr Tyr Thr Lys Asp Thr Asn Asn Asn Leu
1 5 10

<210> SEQ ID NO 141
<211> LENGTH: 10
<212> TYPE: PRT
<213> ORGANISM: Neisseria meningitidis

<400> SEQUENCE: 141

Tyr Thr Lys Asp Thr Asn Asn Asn Leu Thr
1 5 10

<210> SEQ ID NO 142
<211> LENGTH: 10
<212> TYPE: PRT
<213> ORGANISM: Neisseria meningitidis

<400> SEQUENCE: 142

Thr Lys Asp Thr Asn Asn Asn Leu Thr Leu
1 5 10

<210> SEQ ID NO 143
<211> LENGTH: 10
<212> TYPE: PRT
<213> ORGANISM: Neisseria meningitidis

<400> SEQUENCE: 143

Lys Asp Thr Asn Asn Asn Leu Thr Leu Val
1 5 10

<210> SEQ ID NO 144
<211> LENGTH: 10
<212> TYPE: PRT
<213> ORGANISM: Neisseria meningitidis

<400> SEQUENCE: 144

Asp Thr Asn Asn Asn Leu Thr Leu Val Pro
1 5 10

<210> SEQ ID NO 145
<211> LENGTH: 10
<212> TYPE: PRT
<213> ORGANISM: Neisseria meningitidis

<400> SEQUENCE: 145

Thr Asn Asn Asn Leu Thr Leu Val Pro Ala
1 5 10

-continued

<210> SEQ ID NO 146
<211> LENGTH: 10
<212> TYPE: PRT
<213> ORGANISM: Neisseria meningitidis

<400> SEQUENCE: 146

Asn Asn Asn Leu Thr Leu Val Pro Ala Val
1 5 10

<210> SEQ ID NO 147
<211> LENGTH: 10
<212> TYPE: PRT
<213> ORGANISM: Neisseria meningitidis

<400> SEQUENCE: 147

Asn Asn Leu Thr Leu Val Pro Ala Val Val
1 5 10

<210> SEQ ID NO 148
<211> LENGTH: 10
<212> TYPE: PRT
<213> ORGANISM: Neisseria meningitidis

<400> SEQUENCE: 148

Asn Leu Thr Leu Val Pro Ala Val Val Gly
1 5 10

<210> SEQ ID NO 149
<211> LENGTH: 10
<212> TYPE: PRT
<213> ORGANISM: Neisseria meningitidis

<400> SEQUENCE: 149

Leu Thr Leu Val Pro Ala Val Val Gly Lys
1 5 10

<210> SEQ ID NO 150
<211> LENGTH: 10
<212> TYPE: PRT
<213> ORGANISM: Neisseria meningitidis

<400> SEQUENCE: 150

Thr Glu Pro Pro Ser Lys Ser Gln Pro Gln
1 5 10

<210> SEQ ID NO 151
<211> LENGTH: 10
<212> TYPE: PRT
<213> ORGANISM: Neisseria meningitidis

<400> SEQUENCE: 151

Glu Pro Pro Ser Lys Ser Gln Pro Gln Val
1 5 10

<210> SEQ ID NO 152
<211> LENGTH: 10
<212> TYPE: PRT
<213> ORGANISM: Neisseria meningitidis

<400> SEQUENCE: 152

Pro Pro Ser Lys Ser Gln Pro Gln Val Lys
1 5 10

-continued

<210> SEQ ID NO 153
<211> LENGTH: 10
<212> TYPE: PRT
<213> ORGANISM: Neisseria meningitidis

<400> SEQUENCE: 153

Pro Ser Lys Ser Gln Pro Gln Val Lys Val
1 5 10

<210> SEQ ID NO 154
<211> LENGTH: 10
<212> TYPE: PRT
<213> ORGANISM: Neisseria meningitidis

<400> SEQUENCE: 154

Ser Lys Ser Gln Pro Gln Val Lys Val Thr
1 5 10

<210> SEQ ID NO 155
<211> LENGTH: 10
<212> TYPE: PRT
<213> ORGANISM: Neisseria meningitidis

<400> SEQUENCE: 155

Lys Ser Gln Pro Gln Val Lys Val Thr Lys
1 5 10

<210> SEQ ID NO 156
<211> LENGTH: 10
<212> TYPE: PRT
<213> ORGANISM: Neisseria meningitidis

<400> SEQUENCE: 156

Ser Gln Pro Gln Val Lys Val Thr Lys Ala
1 5 10

<210> SEQ ID NO 157
<211> LENGTH: 10
<212> TYPE: PRT
<213> ORGANISM: Neisseria meningitidis

<400> SEQUENCE: 157

Gln Pro Gln Val Lys Val Thr Lys Ala Lys
1 5 10

<210> SEQ ID NO 158
<211> LENGTH: 10
<212> TYPE: PRT
<213> ORGANISM: Neisseria meningitidis

<400> SEQUENCE: 158

Pro Gln Val Lys Val Thr Lys Ala Lys Ser
1 5 10

<210> SEQ ID NO 159
<211> LENGTH: 10
<212> TYPE: PRT
<213> ORGANISM: Neisseria meningitidis

<400> SEQUENCE: 159

Gln Val Lys Val Thr Lys Ala Lys Ser Arg
1 5 10

-continued

<210> SEQ ID NO 160
<211> LENGTH: 10
<212> TYPE: PRT
<213> ORGANISM: Neisseria meningitidis

<400> SEQUENCE: 160

Val Lys Val Thr Lys Ala Lys Ser Arg Ile
1 5 10

<210> SEQ ID NO 161
<211> LENGTH: 10
<212> TYPE: PRT
<213> ORGANISM: Neisseria meningitidis

<400> SEQUENCE: 161

Lys Val Thr Lys Ala Lys Ser Arg Ile Arg
1 5 10

<210> SEQ ID NO 162
<211> LENGTH: 10
<212> TYPE: PRT
<213> ORGANISM: Neisseria meningitidis

<400> SEQUENCE: 162

Asn Ser Lys Ser Ala Tyr Thr Pro Ala His
1 5 10

<210> SEQ ID NO 163
<211> LENGTH: 10
<212> TYPE: PRT
<213> ORGANISM: Neisseria meningitidis

<400> SEQUENCE: 163

Ser Lys Ser Ala Tyr Thr Pro Ala His Tyr
1 5 10

<210> SEQ ID NO 164
<211> LENGTH: 10
<212> TYPE: PRT
<213> ORGANISM: Neisseria meningitidis

<400> SEQUENCE: 164

Lys Ser Ala Tyr Thr Pro Ala His Tyr Thr
1 5 10

<210> SEQ ID NO 165
<211> LENGTH: 10
<212> TYPE: PRT
<213> ORGANISM: Neisseria meningitidis

<400> SEQUENCE: 165

Ser Ala Tyr Thr Pro Ala His Tyr Thr Arg
1 5 10

<210> SEQ ID NO 166
<211> LENGTH: 10
<212> TYPE: PRT
<213> ORGANISM: Neisseria meningitidis

<400> SEQUENCE: 166

Ala Tyr Thr Pro Ala His Tyr Thr Arg Gln
1 5 10

-continued

<210> SEQ ID NO 167
<211> LENGTH: 10
<212> TYPE: PRT
<213> ORGANISM: Neisseria meningitidis

<400> SEQUENCE: 167

Tyr Thr Pro Ala His Tyr Thr Arg Gln Asn
1 5 10

<210> SEQ ID NO 168
<211> LENGTH: 10
<212> TYPE: PRT
<213> ORGANISM: Neisseria meningitidis

<400> SEQUENCE: 168

Thr Pro Ala His Tyr Thr Arg Gln Asn Asn
1 5 10

<210> SEQ ID NO 169
<211> LENGTH: 10
<212> TYPE: PRT
<213> ORGANISM: Neisseria meningitidis

<400> SEQUENCE: 169

Pro Ala His Tyr Thr Arg Gln Asn Asn Thr
1 5 10

<210> SEQ ID NO 170
<211> LENGTH: 10
<212> TYPE: PRT
<213> ORGANISM: Neisseria meningitidis

<400> SEQUENCE: 170

Ala His Tyr Thr Arg Gln Asn Asn Thr Asp
1 5 10

<210> SEQ ID NO 171
<211> LENGTH: 10
<212> TYPE: PRT
<213> ORGANISM: Neisseria meningitidis

<400> SEQUENCE: 171

His Tyr Thr Arg Gln Asn Asn Thr Asp Val
1 5 10

<210> SEQ ID NO 172
<211> LENGTH: 10
<212> TYPE: PRT
<213> ORGANISM: Neisseria meningitidis

<400> SEQUENCE: 172

Tyr Thr Arg Gln Asn Asn Thr Asp Val Phe
1 5 10

<210> SEQ ID NO 173
<211> LENGTH: 10
<212> TYPE: PRT
<213> ORGANISM: Neisseria meningitidis

<400> SEQUENCE: 173

Thr Arg Gln Asn Asn Thr Asp Val Phe Val
1 5 10

-continued

<210> SEQ ID NO 174
<211> LENGTH: 10
<212> TYPE: PRT
<213> ORGANISM: Neisseria meningitidis

<400> SEQUENCE: 174

Arg Gln Asn Asn Thr Asp Val Phe Val Pro
1 5 10

<210> SEQ ID NO 175
<211> LENGTH: 10
<212> TYPE: PRT
<213> ORGANISM: Neisseria meningitidis

<400> SEQUENCE: 175

Gln Asn Asn Thr Asp Val Phe Val Pro Ala
1 5 10

<210> SEQ ID NO 176
<211> LENGTH: 10
<212> TYPE: PRT
<213> ORGANISM: Neisseria meningitidis

<400> SEQUENCE: 176

Asn Asn Thr Asp Val Phe Val Pro Ala Val
1 5 10

<210> SEQ ID NO 177
<211> LENGTH: 10
<212> TYPE: PRT
<213> ORGANISM: Neisseria meningitidis

<400> SEQUENCE: 177

Asn Thr Asp Val Phe Val Pro Ala Val Val
1 5 10

<210> SEQ ID NO 178
<211> LENGTH: 10
<212> TYPE: PRT
<213> ORGANISM: Neisseria meningitidis

<400> SEQUENCE: 178

Thr Asp Val Phe Val Pro Ala Val Val Gly
1 5 10

<210> SEQ ID NO 179
<211> LENGTH: 10
<212> TYPE: PRT
<213> ORGANISM: Neisseria meningitidis

<400> SEQUENCE: 179

Asp Val Phe Val Pro Ala Val Val Gly Lys
1 5 10

<210> SEQ ID NO 180
<211> LENGTH: 10
<212> TYPE: PRT
<213> ORGANISM: Neisseria meningitidis

<400> SEQUENCE: 180

Val Phe Val Pro Ala Val Val Gly Lys Pro
1 5 10

-continued

<210> SEQ ID NO 181
<211> LENGTH: 10
<212> TYPE: PRT
<213> ORGANISM: Neisseria meningitidis

<400> SEQUENCE: 181

```
Phe Val Pro Ala Val Val Gly Lys Pro Gly
 1               5                  10
```

<210> SEQ ID NO 182
<211> LENGTH: 18
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (1)...(18)

<400> SEQUENCE: 182

```
gat atc atc gat gga ttc                                        18
Asp Ile Ile Asp Gly Phe
 1               5
```

<210> SEQ ID NO 183
<211> LENGTH: 36
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (3)...(35)

<400> SEQUENCE: 183

```
ga tca gct gct aac ggt ggt gct tca ggt cag gtt g               36
   Ser Ala Ala Asn Gly Gly Ala Ser Gly Gln Val
    1               5                  10
```

<210> SEQ ID NO 184
<211> LENGTH: 36
<212> TYPE: DNA
<213> ORGANISM: Artificial Sequence
<220> FEATURE:
<223> OTHER INFORMATION: linker insertion

<400> SEQUENCE: 184

```
gatccaacct gacctgaagc accaccgtta gcagct                        36
```

<210> SEQ ID NO 185
<211> LENGTH: 14
<212> TYPE: PRT
<213> ORGANISM: Artificial Sequence
<220> FEATURE:
<223> OTHER INFORMATION: peptide linker

<400> SEQUENCE: 185

```
Gly Ser Ala Ala Asn Gly Gly Ala Ser Gly Gln Val Gly Ser
 1               5                  10
```

<210> SEQ ID NO 186
<211> LENGTH: 36
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (3)...(35)

-continued

<400> SEQUENCE: 186

```
ga tca acc aaa gac acc aat aac aac ctc acc cta g                        36
   Ser Thr Lys Asp Thr Asn Asn Asn Leu Thr Leu
    1               5                   10
```

<210> SEQ ID NO 187
<211> LENGTH: 36
<212> TYPE: DNA
<213> ORGANISM: Artificial Sequence
<220> FEATURE:
<223> OTHER INFORMATION: linker insertion

<400> SEQUENCE: 187

```
gatcctaggg tgaggttgtt attggtgtct ttggtt                                 36
```

<210> SEQ ID NO 188
<211> LENGTH: 14
<212> TYPE: PRT
<213> ORGANISM: Artificial Sequence
<220> FEATURE:
<223> OTHER INFORMATION: peptide linker

<400> SEQUENCE: 188

```
Gly Ser Thr Lys Asp Thr Asn Asn Asn Leu Thr Leu Gly Ser
 1               5                  10
```

<210> SEQ ID NO 189
<211> LENGTH: 12
<212> TYPE: PRT
<213> ORGANISM: Neisseria meningitidis

<400> SEQUENCE: 189

```
Tyr Tyr Thr Lys Asp Thr Asn Asn Asn Leu Thr Leu
 1               5                  10
```

<210> SEQ ID NO 190
<211> LENGTH: 12
<212> TYPE: PRT
<213> ORGANISM: Neisseria meningitidis

<400> SEQUENCE: 190

```
Tyr Tyr Thr Lys Asn Thr Asn Asn Asn Leu Thr Leu
 1               5                  10
```

<210> SEQ ID NO 191
<211> LENGTH: 393
<212> TYPE: PRT
<213> ORGANISM: Neisseria meningitidis

<400> SEQUENCE: 191

```
Met Arg Lys Lys Leu Thr Ala Leu Val Leu Ser Ala Leu Pro Leu Ala
 1               5                  10                  15

Ala Val Ala Asp Val Ser Leu Tyr Gly Glu Ile Lys Ala Gly Val Glu
            20                  25                  30

Gly Arg Asn Ile Gln Ala Gln Leu Thr Glu Gln Pro Gln Val Thr Asn
        35                  40                  45

Gly Val Gln Gly Asn Gln Val Lys Val Thr Lys Ala Lys Ser Arg Ile
    50                  55                  60

Arg Thr Lys Ile Ser Asp Phe Gly Ser Phe Ile Gly Phe Lys Gly Ser
65                  70                  75                  80
```

-continued

```
Glu Asp Leu Gly Glu Gly Leu Lys Ala Val Trp Gln Leu Glu Gln Asp
                85                  90                  95

Val Ser Val Ala Gly Gly Gly Ala Ser Gln Trp Gly Asn Arg Glu Ser
            100                 105                 110

Phe Ile Gly Leu Ala Gly Glu Phe Gly Thr Leu Arg Ala Gly Arg Val
        115                 120                 125

Ala Asn Gln Phe Asp Asp Ala Ser Gln Ala Ile Asn Pro Trp Asp Ser
    130                 135                 140

Asn Asn Asp Val Ala Ser Gln Leu Gly Ile Phe Lys Arg His Asp Asp
145                 150                 155                 160

Met Pro Val Ser Val Arg Tyr Asp Ser Pro Glu Phe Ser Gly Phe Ser
                165                 170                 175

Gly Ser Val Gln Phe Val Pro Ala Gln Asn Ser Lys Ser Ala Tyr Lys
            180                 185                 190

Pro Ala Tyr Tyr Thr Lys Asp Thr Asn Asn Asn Leu Thr Leu Val Pro
        195                 200                 205

Ala Val Val Gly Lys Pro Gly Ser Asp Val Tyr Tyr Ala Gly Leu Asn
    210                 215                 220

Tyr Lys Asn Gly Gly Phe Ala Gly Asn Tyr Ala Phe Lys Tyr Ala Arg
225                 230                 235                 240

His Ala Asn Val Gly Arg Asn Ala Phe Glu Leu Phe Leu Ile Gly Ser
                245                 250                 255

Ala Thr Ser Asp Glu Ala Lys Gly Thr Asp Pro Leu Lys Asn His Gln
            260                 265                 270

Val His Arg Leu Thr Gly Gly Tyr Glu Glu Gly Gly Leu Asn Leu Ala
        275                 280                 285

Leu Ala Ala Gln Leu Asp Leu Ser Glu Asn Gly Asp Lys Ala Lys Thr
    290                 295                 300

Lys Asn Ser Thr Thr Glu Ile Ala Ala Thr Ala Ser Tyr Arg Phe Gly
305                 310                 315                 320

Asn Ala Val Pro Arg Ile Ser Tyr Ala His Gly Phe Asp Leu Ile Glu
                325                 330                 335

Arg Gly Lys Lys Gly Glu Asn Thr Ser Tyr Asp Gln Ile Ile Ala Gly
            340                 345                 350

Val Asp Tyr Asp Phe Ser Lys Arg Thr Ser Ala Ile Val Ser Gly Ala
        355                 360                 365

Trp Leu Lys Arg Asn Thr Gly Ile Gly Asn Tyr Thr Gln Ile Asn Ala
    370                 375                 380

Ala Ser Val Gly Leu Arg His Lys Phe
385                 390


<210> SEQ ID NO 192
<211> LENGTH: 6
<212> TYPE: PRT
<213> ORGANISM: Artificial Sequence
<220> FEATURE:
<223> OTHER INFORMATION: linker peptide

<400> SEQUENCE: 192

Asp Ile Ile Asp Gly Ser
 1               5
```

-continued

```
<210> SEQ ID NO 193
<211> LENGTH: 4
<212> TYPE: PRT
<213> ORGANISM: Neisseria meningitidis

<400> SEQUENCE: 193

Gly Arg Asn Ile
 1
```